US009914915B2

(12) United States Patent
Fischetti et al.

(10) Patent No.: US 9,914,915 B2
(45) Date of Patent: Mar. 13, 2018

(54) STREPTOCOCCUS BACTERIOPHAGE LYSINS FOR DETECTION AND TREATMENT OF GRAM POSITIVE BACTERIA

(71) Applicants: Vincent A. Fischetti, West Hempstead, NY (US); Jonathan Schmitz, New York, NY (US); Daniel Gilmer, New York, NY (US); Chad Euler, New York, NY (US)

(72) Inventors: Vincent A. Fischetti, West Hempstead, NY (US); Jonathan Schmitz, New York, NY (US); Daniel Gilmer, New York, NY (US); Chad Euler, New York, NY (US)

(73) Assignee: THE ROCKEFELLER UNIVERSITY, New York, NY (US)

(*) Notice: Subject to any disclaimer, the term of this patent is extended or adjusted under 35 U.S.C. 154(b) by 198 days.

(21) Appl. No.: 14/685,696

(22) Filed: Apr. 14, 2015

(65) Prior Publication Data
US 2015/0267185 A1 Sep. 24, 2015

Related U.S. Application Data

(63) Continuation of application No. 14/112,963, filed as application No. PCT/US2012/034456 on Apr. 20, 2012, now Pat. No. 9,034,322.

(60) Provisional application No. 61/477,836, filed on Apr. 21, 2011.

(51) Int. Cl.
A61K 38/00 (2006.01)
A61K 9/14 (2006.01)
A61K 9/06 (2006.01)
C12N 9/14 (2006.01)
C12N 9/36 (2006.01)
A61K 38/16 (2006.01)
A61K 38/50 (2006.01)
A61K 38/47 (2006.01)
A61K 45/06 (2006.01)

(52) U.S. Cl.
CPC .......... *C12N 9/2462* (2013.01); *A61K 38/162* (2013.01); *A61K 38/47* (2013.01); *A61K 38/50* (2013.01); *A61K 45/06* (2013.01); *C12Y 302/01017* (2013.01)

(58) Field of Classification Search
CPC ........ A61K 38/00; A61K 9/0014; A61K 9/06; C12N 9/14; G01N 2333/3156; G01N 2333/98
See application file for complete search history.

(56) References Cited

U.S. PATENT DOCUMENTS

| 5,604,109 | A | 2/1997 | Fischetti et al. |
| 5,985,271 | A | 11/1999 | Fischetti et al. |
| 6,017,528 | A | 1/2000 | Fischetti et al. |
| 6,056,955 | A | 5/2000 | Fischetti et al. |
| 6,248,324 | B1 | 6/2001 | Fischetti et al. |
| 6,254,866 | B1 | 7/2001 | Fischetti et al. |
| 6,264,945 | B1 | 7/2001 | Fischetti et al. |
| 7,402,309 | B2 | 7/2008 | Fischetti et al. |
| 7,569,223 | B2 | 8/2009 | Fischetti et al. |
| 7,582,291 | B2 | 9/2009 | Young et al. |
| 7,638,600 | B2 | 12/2009 | Fischetti et al. |
| 2006/0292135 | A1 | 12/2006 | Loomis et al. |
| 2007/0025978 | A1 | 2/2007 | Yoong et al. |
| 2008/0221035 | A1 | 9/2008 | Fischetti et al. |
| 2010/0004321 | A1 | 1/2010 | Ross et al. |
| 2010/0047222 | A1 | 2/2010 | Fischetti et al. |
| 2010/0172918 | A1 | 7/2010 | Yoon et al. |
| 2010/0310522 | A1 | 12/2010 | Gasson et al. |

FOREIGN PATENT DOCUMENTS

| WO | WO08018854 | 2/2008 |
| WO | WO10002959 | 1/2010 |
| WO | 2011091412 | 7/2011 |

OTHER PUBLICATIONS

Vollmer, W et al (2008) Peptidoglycan structure and architecture FEMS Microbial Rev 32(2):149-167.
Wang, IN et al (2000) Holins: the protein clocks of bacteriophage infections Annu Rev Microbiol 54:799-825.
Wang, Y et al (2009) Purified recombinant phage lysin LySMP: an extensive spectrum of lytic activity for swine streptococci Curr Microbial 58(6):609-615.
Wiegand, I et al (2008) Agar and broth dilution methods to determine the minimal inhibitory concentration (MIC) of antimicrobial substances Nat Protoc 3(2):163-175.
Wilson, P et al (2003) Linezolid resistance in clinical isolates of *Staphylococcus aureus* J Antimicrob Chemother 51 (1):186-188.
Witzenrath, M et al (2009) Systemic use of the endolysin Cpl-1 rescues mice with fatal pneumococcal pneumonia Cont Care Med 37(2):642-649.
Wylie, GP et al (2005) Prolylpeptide binding by the prokaryotic SH3-like domain of the diphtheria toxin repressor: a regulatory switch Biochemistry 44(1):40-51.
Xu, Q et al (2010) Structure of the gamma-D-glutamyl-L-diamino acid endopeptidase YkfC from *Bacillus cereus* in complex with L-Ala-gamma-D-Glu: insights into substrate recognition by NlpC/P60 cysteine peptidases Acta Crystallogr Sect F Struct Biol Cryst Commun 66(Pt 10):1354-1364.

(Continued)

Primary Examiner — Kagnew H Gebreyesus
(74) Attorney, Agent, or Firm — Klauber & Jackson LLC

(57) ABSTRACT

The present invention provides methods, compositions and articles of manufacture useful for the prophylactic and therapeutic amelioration and treatment of gram-positive bacteria, including *Streptococcus* and *Staphylococcus*, and related conditions. The invention provides compositions and methods incorporating and utilizing *Streptococcus suis* derived bacteriophage lysins, particularly PlySs2 and/or PlySs1 lytic enzymes and variants thereof, including truncations thereof. Methods for treatment of humans are provided.

16 Claims, 47 Drawing Sheets

(56) References Cited

OTHER PUBLICATIONS

Yoong, P et al (2004) Identification of a broadly active phage lytic enzyme with lethal activity against antibiotic-resistant *Enterococcus faecalis* and *Enterococcus faecium* J Bacterial 186(14):4808-4812.
Yoong, P et al (2006) PlyPH, a bacteriolytic enzyme with a broad pH range of activity and lytic action against *Bacillus anthracis* J Bacteriol 188(7):2711-2714.
Young, MH et al (2005) Necrotizing fasciitis: pathogenesis and treatment Expert Rev Anti Infect Ther 3(2):279-294.
Zimmer, M et al (2002) The murein hydrolase of the bacteriophage phi3626 dual lysis system is active against all tested *Clostridium perfringens* strains Appl Environ Microbial 68(11):5311-5317.
Fischetti VA (2010) Bacteriophage endolysins: a novel anti-infective to control Gram-positive pathogens Int J Med Microbiol 300(6):357-362.
Lucas S et al Uniprot:B9WWF8 (2009) XP055150805.
Baker, Jr et al (2006) Endopeptidase and glycosidase activities of the bacteriophage B30 lysin Appl Environ Microbiol 72(10):6825-6828.
Becker, SC et al (2009) LysK CHAP endopeptidase domain is required for lysis of live staphylococcal cells FEMS Microbial Lett 294(1):52-60.
Beres, SB et al (2007) Contribution of Exogenous Genetic Elements to the Group A *Streptococcus* Metagenome PLoS One 2(8):1-14.
Bessen, DE et al (2011) Whole-genome Association Study on Tissue Tropism Phenotypes in Group A *Streptococcus* J Bacterial 193(23):6651-6663.
Cantin, M et al (1992) Antimicrobial resistance patterns and plasmid profiles of *Streptococcus suis* isolates J Vet Diagn Invest 4(2):170-174.
Chen, C et al (2007) A glimpse of streptococcal toxic shock syndrome from comparative genomics of S. suis 2 Chinese isolates PLoS One 2(3):e315.
Cheng, Q et al (2005) Removal of group B *Streptococci* colonizing the vagina and oropharynx of mice with a bacteriophage lytic enzyme Antimicrob Agents Chemother 49(1):111-117.
Cole, JN et al (2011) Molecular insight into invasive group A *Streptococcal* disease Nat Rev Microbiol 9(10):724-736.
Daniel, A et al (2010) Synergism between a novel chimeric lysin and oxacillin protects against infection by methicillin-resistant *Staphylococcus aureus* Antimicrob Agents Chemother 54(4):1603-1612.
Donovan, DM et al (2008) LambdaSa2 prophage endolysin requires Cpl-7-binding domains and amidase-5 domain for antimicrobial lysis of *Streptococci* FEMS Microbial Lett 287(1):22-33.
Fischetti, VA (2005) Bacteriophage lytic enzymes: novel anti-infectives Trends Microbiol 13(10):491-496.
Fischetti, VA (2008) Bacteriophage lysins as effective antibacterials Curr Opin Microbiol 11(5):393-400.
Garcia, E et al (1988) Molecular evolution of lytic enzymes of *Streptococcus pneumoniae* and its bacteriophages Proc Natl Acad Sci USA 85(3):914-918.
Garcia, P et al (1990) Modular organization of the lytic enzymes of *Streptococcus pneumoniae* and its bacteriophages Gene 86(1):81-88.
Grandgirard, D et al (2008) Phage lytic enzyme Cpl-1 for antibacterial therapy in experimental pneumococcal meningitis J Infect Dis 197(11):1519-1522.
Harel, J et al (2003) Identification of an inducible bacteriophage in a virulent strain of *Streptococcus suis* serotype 2 Infect Immun 71(10):6104-6108.
Holden, MT et al (2009) Rapid evolution of virulence and drug resistance in the emerging zoonotic pathogen *Streptococcus suis* PLoS One 4(7):e6072 doi: 10.1371/journal.pone.0006072.
Hudson, IR (1994) The efficacy of intranasal mupirocin in the prevention of staphylococcal infections: a review of recent experience J Hosp Infect 27(2):81-98.
Jado, I et al (2003) Phage lytic enzymes as therapy for antibiotic-resistant *Streptococcus pneumoniae* infection in a murine sepsis model J Antimicrob Chemother 52(6):967-973.

Loeffler, JM et al (2001) Rapid killing of *Streptococcus pneumoniae* with a bacteriophage cell wall hydrolase Science 294(5549):2170-2172.
Loeffler, JM et al (2003) Phage lytic enzyme Cpl-1 as a novel antimicrobial for pneumococcal bacteremia Infect Immun 71(11):6199-6204.
Loessner, MJ et al (1995) Heterogeneous endolysins in *Listeria monocytogenes* bacteriophages: a new class of enzymes and evidence for conserved holin genes within the siphoviral lysis cassettes Mol Microbial 16(6):1231-1241.
Loessner, MJ et al (1997) Three *Bacillus cereus* bacteriophage endolysins are unrelated but reveal high homology to cell wall hydrolases from different bacilli J Bacterial 179(9):2845-2851.
Loessner MJ et al (1999) Evidence for a holin-like protein gene fully embedded out of frame in the endolysin gene of *Staphylococcus aureus* bacteriophage 187 Journal of Bacteriology 181(15):4452-4460.
Loessner, MJ et al (2002) C-terminal domains of *Listeria monocytogenes* bacteriophage murein hydrolases determine specific recognition and high-affinity binding to bacterial cell wall carbohydrates Mol Microbiol 44(2):335-349.
López et al (1992) Structural analysis and biological significance of the cell wall lytic enzymes of *Streptococcus pneumonia* and its bacteriophage FEMS Microbiol Lett 100:439-448.
López, R et al (1997) Evidence for a holin-like protein gene fully embedded out of frame in the endolysin gene of *Staphylococcus aureus* bacteriophage 187 Microbial Drug Resistance 3(2):199-211.
Ma, YL et al (2008) Isolation and identification of a bacteriophage capable of infecting *Streptococcus suis* type 2 strains Vet Microbial 132(3-4):340-347.
Nelson, D et al (2001) Prevention and elimination of upper respiratory colonization of mice by group A *Streptococci* by using a bacteriophage lytic enzyme Proc Natl Acad Sci USA 98(7):4107-4112.
Nelson, D et al (2006) PlyC: a multimeric bacteriophage lysin. Proc Natl Acad Sci USA 103(28):10765-10770.
O'Flaherty, S et al (2005) the recombinant phage lysin LysK has a broad spectrum of lytic activity against clinically relevant *Staphylococci*, including methicillin-resistant *Staphylococcus aureus* J Bacteriol 187(20):7161-7164.
O'Flaherty, S et al (2009) Bacteriophage and their lysins for elimination of infectious bacteria FEMS Microbial Rev 33 (4):801-819.
Pastagia, M et al (2011) A novel chimeric lysin shows superiority to mupirocin for skin decolonization of methicillin-resistant and -sensitive *Staphylococcus aureus* strains Antimicrob Agents Chemother 55(2):738-744.
Pohl, E et al (1999) Crystal structure of a cobalt-activated diphtheria toxin repressor-DNA complex reveals a metal-binding SH3-like domain J Mol Biol 292(3):653-667.
Pritchard, DG et al (2007) LambdaSa1 and LambdaSa2 prophage lysins of *Streptococcus agalactiae* Appl Environ Microbiol 73(22):7150-7154.
Rashel, M et al (2007) Efficient elimination of multidrug-resistant *Staphylococcus aureus* by cloned lysin derived from bacteriophage phi MR11 J Infect Dis 196(8):1237-1247.
Romero, A et al (1990) Sequence of the *Streptococcus pneumoniae* bacteriophage HB-3 amidase reveals high homology with the major host autolysin J Bacterial 172(9):5064-5070.
Ronda, C et al (1987) Biological role of the pneumococcal amidase. Cloning of the lytA gene in *Streptococcus pneumoniae* Eur J Biochem 164(3):621-624.
Rouse, MS et al (2005) In vitro and in vivo evaluations of the activities of lauric acid monoester formulations against *Staphylococcus aureus* Antimicrob Agents Chemother 49(8):3187-3191.
Sánchez-Puelles JM et al (1987) 3'-end modifications of the *Streptococcus pneumoniae* lytA gene: role of the carboxy terminus of the pneumococcal autolysin in the process of enzymatic activation (conversion) Gene 61(1):13-19.
Schleifer, KH et al (1972) Peptidoglycan types of bacterial cell walls and their taxonomic implications Bacterial Rev 36 (4):407-477.

(56) References Cited

OTHER PUBLICATIONS

Schmitz, JE et al (2010) Identifying active phage lysins through functional viral metagenomics Adv Environ Microbial 76(21):7181-7187.

Schuch, R et al (2002) A bacteriolytic agent that detects and kills *Bacillus anthracis* Nature 418(6900):884-889.

Sriskandan, S et al (2006) Invasive Disease and Toxic Shock due to Zoonotic *Streptococcus suis*: An Emerging Infection in the East? PLoS Medicine 3(5):595-587 e187.

Steer, AC et al (2009) Global emm type distribution of group A *Streptococci*: systematic review and implications for vaccine development Lancet Infect Dis 9(10):611-616.

FIGURE 1: Lytic cycle versus lysin treatment. Lysins recombinantly expressed and purified are able to lyse bacteria just as well as phage expressing lysins from within their host.

FIGURE 3A

PlySs1

•Full-length construct (that which was originally cloned from strain 7711):
1359 bp; 452 amino acids; 49.67 kDa; Theoretical pI = 6.87

•Truncated construct (that which was expressed, purified, and characterized):
765 bp; 254 amino acids; 28.09 kDa; Theoretical pI = 7.7

```
ATGACAATCA ATCTTGAAAC ATCCATTCGT TGGATGAGCG ACCGTGTCGG
CAAAGTCTCT TACTCAATGG ACTATCGTAA CGGTCCGAAT AGTTATGACT
GCTCTAGTGC TGTATATTAT GCGCTAATGG CGGGTGGTGC AATTTCTGCA
GGTTGGGCGG TTAACACTGA GTATATGCAT GACTGGTTGA TACGTAACGG
ATATGTTTTG GTAGCTGAAA ATAAACCATT TAACGCTCAA AGACATGACG
TTTGTATTTT GGGTAAACGT GGCTATTCGA GCGGAGCAGG TGGTCACGTC
GTTATCTTTG TGGATAATGT TAATGTGATA CATTGTAACT ATGCACGTAA
CGGAATTTCC ATTGATAATT ATAATCAAGT GCATCGTGGT ATGTATTACT
ATCTATATCG CCCAGCAAAT CAACCCAGCA TCAGCAACAA ATCACTGGAT
CAGCTTGTTA AGGAGACTTT GGCTGGGGTA CATGGCAACG GGGACACCCG
TAAGGCAAGT CTTGGCAGTC AATACGAGGC TGTCATGGCG GTTATCAATG
GCAAAGCTTC GGCAAGCGAG AAATCTGATG AGGAACTTGC TAGGGAAGTC
TTAGCAGGTA AGCACGGGGC TGGAGAGGAC CGAAAACGGT CATTAGGACC
ACGCTATGAG CCTGTTCAAG CCAAGGTCAA CGAATTGCTC AAGGCTAAGG
AAAAACCGTC TGAGACGGCC AAAAATGAAC CACAGACGGT GCAATTCAAG
GAGGACGGGG ACTTGTCTTT CAATGGTGCC ATTCTTAAGA AGTCTGTCCT
CGAAATTATC CTGAAAAAGT GTAAAGAACA TGACATCTTA CCAAGCTATG
CCCTAACTAT CCTACACTAT GAAGGGCTTT GGGGCACTTC TGCTGTCGGT
AAGGCCGACA ACAACTGGGG CGGTATGACC TGGACTGGCC AAGGCAACCG
TCCGAGCGGA GTAATTGTGA CTCAAGGTTT GGCTCGGCCA TCGAACGAGG
GAGGCCACTA CATGCACTAT GCCACCGTGG ATGATTTCCT GACGGACTGG
TTCTACCTGC TTCGCAAGGA CGGGTCTTAC AAGGTATCTG GTGCATTGAC
CTTCAGCGAG TCCATTAAGG GCATGTTCCA GGTTGGCGGA GCTAAATACG
ACTATGCAGC CGCCGGCTAC GATAGTTACC TGGTCGGCGC CACTAGCAGG
CTAAAAGCTA TCGAGTCCGA AAATGGCAGT CTGACACGGT TTGATGCCAC
ATCAAATAAT GTCCATTCGG TTGACCCTGA TAAAATCTCT GTTGATATTG
ACGGCATTGA AGTTACGATC AATGGTGTTG TCTACAAGCT GGAAAAGAAA
CCAGTCTAA
```

FIGURE 3B

- N-terminus: Experimentally shown to possess γ-D-glutaminyl-L-lysine endopeptidase activity

- Dual CPL-7 binding domain (Pfam accession #PF08230)

- C-terminus: Endo-beta-N-acetylglucosaminidase enzymatic domain (PF01832)

```
MTINLETSIR WMSDRVGKVS YSMDYRNGPN SYDCSSAVYY ALMAGGAISA
GWAVNTEYMH DWLIRNGYVL VAENKPFNAQ RHDVCILGKR GYSSGAGGHV
VIFVDNVNVI HCNYARNGIS IDNYNQVHRG MYYYLYRPAN QPSISNKSLD
QLVKETLAGV HGNGDTRKAS LGSQYEAVMA VINGKASASE KSDEELAREV
LAGKHGAGED RKRSLGPRYE PVQAKVNELL KAKEKPSETA KNEPQTVQFK
EDGDLSFNGA ILKKSVLEII LKKCKEHDIL PSYALTILHY EGLWGTSAVG
KADNNWGGMT WTGQGNRPSG VIVTQGLARP SNEGGHYMHY ATVDDFLTDW
FYLLRKDGSY KVSGALTFSE SIKGMFQVGG AKYDYAAAGY DSYLVGATSR
LKAIESENGS LTRFDATSNN VHSVDPDKIS VDIDGIEVTI NGVVYKLEKK PV
```

**NOTE: The full-length gene/protein shown here is what was cloned during the initial functional screen of the *S. suis* 7711 genome. For large-scale expression, purification, and functional analysis, a truncated construct was sub-cloned that omitted the C-terminal enzymatic domain. The residues included in this construct are underlined above.

↓ TRUNCATION POINT

FIGURE 4A

PlySS2

- GenBank Accession Number: ZP_03625529 (from *S. suis* strain 89/1591)

- 738 base pairs; 245 amino acids; 26.06 kDa; Theoretical pI = 9.0

```
ATGACAACAG TAAATGAAGC ATTAAATAAT GTAAGAGCTC AGGTTGGGTC
CGGTGTGTCT GTTGGCAACG GCGAATGCTA CGCTTTGGCT AGTTGGTACG
AGCGCATGAT TAGTCCGGAT GCAACTGTCG GACTTGGCGC TGGTGTGGGC
TGGGTCAGCG GTGCAATCGG CGATACAATC TCTGCCAAAA ACATCGGCTC
ATCATACAAC TGGCAAGCTA ACGGCTGGAC AGTTTCCACA TCTGGTCCAT
TTAAAGCAGG TCAGATTGTG ACGCTTGGGG CAACACCAGG AAACCCTTAC
GGACATGTGG TAATCGTCGA AGCAGTGGAC GGCGATAGAT TGACTATTTT
GGAGCAAAAC TACGGCGGGA AACGTTATCC CGTCCGTAAT TATTACAGCG
CTGCAAGCTA TCGTCAACAG GTCGTGCATT ACATCACACC GCCTGGCACG
GTCGCACAGT CAGCACCCAA CCTTGCAGGC TCTCGTTCCT ATCGCGAGAC
GGGCACTATG ACTGTCACGG TCGATGCTCT CAATGTTCGC AGGGCGCCAA
ATACTTCAGG CGAGATTGTA GCAGTATACA AGCGTGGTGA ATCATTTGAC
TATGATACTG TCATCATCGA TGTCAATGGC TATGTCTGGG TGTCTTACAT
AGGCGGCAGC GGCAAACGTA ACTACGTTGC GACGGGCGCT ACCAAAGACG
GTAAGCGTTT CGGCAATGCT TGGGGTACAT TTAAATAA
```

FIGURE 4B

- CHAP enzymatic domain (PF05257)

- SH3-Type 5 binding domain (PF08460)

```
MTTVNEALNN VRAQVGSGVS VGNGECYALA SWYERMISPD ATVGLGAGVG
WVSGAIGDTI SAKNIGSSYN WQANGWTVST SGPFKAGQIV TLGATPGNPY
GHVVIVEAVD GDRLTILEQN YGGKRYPVRN YYSAASYRQQ VVHYITPPGT
VAQSAPNLAG SRSYRETGTM TVTVDALNVR RAPNTSGEIV AVYKRGESFD
YDTVIIDVNG YVWVSYIGGS GKRNYVATGA TKDGKRFGNA WGTFK
```

Effect of PlySS2 against Staphylococcal Strains

7711:
Serotype 7
(encoding strain

S735
Serotype 2
(type strain)

7997
Serotype 9

FIGURE 27

| Species | Strain | MIC (visual) µg/ml | MIC (colorimetric) µg/ml |
|---|---|---|---|
| S. agalactiae | GBS 090R | 256-128 | 256-128 |
| | GBS type II | 512 | 512 |
| S. pyogenes | GrAS SF370 | 256-128 | 256-128 |
| | GrAS 5005 | 256-128 | 256-128 |
| S. aureus | 8325 | 16 | 16 |
| | MW2 | 16 | 32-16 |
| | LyrA | 64-32 | 64-32 |
| | VISA III | 32 | >1,024 |
| L. monocytogenes | HER1083 | 8 | 16-8 |
| | HER1184 | 8 | 16-8 |
| E. coli | Top10 | >1,024 | >1,024 |

Strain 223

Strain 245

Strain 932

Strain 926

FIGURE 30

```
PlySs2    TVNEALNNVRAQVGSGVSVGNGECYALASWYERMISPDATVGLGAGVGWVSGAIGDTISA
PlyC      ----NLANAQAQVG---KYIGDGQCYAWVGWWSARVCG-YSISYSTGDPMLP-LIGDMNA
          *   :.**** . :   * :***:**** .,::  ::  ::.::: *    :*. :.*

PlySs2    KNIGSSYNWQAN------GWTVSTSG-----PFKAGQIVTLGATPGNP------YGHVTVEAV
PlyC      HSIHLGWDWSIANTGIVNYPVGTVGRKEDLRVGAIWCATAFSGAPFYTGQYGHTGIIESW
          :.*  *::*:**      * ** ::*     * :.*:  *.*:* :        *** :.*:.

PlySs2    DGDRLTIEQNYGGKRYPVRNYISAASYRQVVHYI----
PlyC      SDTTVTVLEQNILG-SPVIRSTYDLNTFLSTLIGLITFK
          .  : *:*** *  :** *::  ::::.: *
```

STREPTOCOCCUS BACTERIOPHAGE LYSINS FOR DETECTION AND TREATMENT OF GRAM POSITIVE BACTERIA

CROSS REFERENCE TO RELATED APPLICATIONS

The present application is a Continuation of National Stage application Ser. No. 14/112,963, filed Nov. 19, 2013, which claims priority from PCT Application No. PCT/US2012/034456 filed Apr. 20, 2012, which in turn, claims priority from U.S. Provisional Application Ser. No. 61/477,836 filed Apr. 21, 2011. Applicants claim the benefits of 35 U.S.C. §120 as to the National Stage Application and the PCT Application and priority under 35 U.S.C. §119 as to the said U.S. Provisional application, and the entire disclosures of the applications are incorporated herein by reference in their entireties.

STATEMENT OF GOVERNMENT SUPPORT

This invention was made with government support under A111822 awarded by the NIH. The government has certain rights in the invention.

FIELD OF THE INVENTION

The present invention relates generally to methods, compositions and articles of manufacture useful for the prophylactic and therapeutic amelioration and treatment of gram-positive bacteria, including *Streptococcus* and *Staphylococcus* bacterial strains, including pathogenic and antibiotic-resistant bacteria, and related conditions. The invention relates to compositions and articles of manufacture incorporating isolated *Streptococcus suis* bacteriophage lysins including PlySs2 and/or PlySs1 lytic enzymes and variants thereof, including truncations thereof, and to methods utilizing the lysin polypeptides and compositions.

BACKGROUND OF THE INVENTION

A major problem in medicine has been the development of drug resistant bacteria as more antibiotics are used for a wide variety of illnesses and other conditions. Hospital infections are the 8$^{th}$ leading cause of death in the United States, due in large part to drug-resistant and newly-emerging pathogens. For example, there are over 500,000 cases of *Staphylococcus aureus* annually in the U.S. and over 65% of strains are multidrug resistant (MRSA). The use of more antibiotics and the number of bacteria showing resistance has prompted longer treatment times. Furthermore, broad, non-specific antibiotics, some of which have detrimental effects on the patient, are now being used more frequently. A related problem with this increased use is that many antibiotics do not penetrate mucus linings easily. Additionally, the number of people allergic to antibiotics appears to be increasing. Accordingly, there is a commercial need for new antibacterial approaches, especially those that operate via new modalities or provide new means to kill pathogenic bacteria.

Gram-positive bacteria are surrounded by a cell wall containing polypeptides and polysaccharide. The gram-positive cell wall appears as a broad, dense wall that is 20-80 nm thick and consists of numerous interconnecting layers of peptidoglycan. Between 60% and 90% of the gram-positive cell wall is peptidoglycan, providing cell shape, a rigid structure, and resistance to osmotic shock. The cell wall does not exclude the Gram stain crystal violet, allowing cells to be stained purple, and therefore "Gram-positive." Gram-positive bacteria include but are not limited to the genera *Actinomyces, Bacillus, Listeria, Lactococcus, Staphylococcus, Streptococcus, Enterococcus, Mycobacterium, Corynebacterium,* and *Clostridium*. Medically relevant species include *Streptococcus pyogenes, Streptococcus pneumoniae, Staphylococcus aureus,* and *Enterococcus faecalis. Bacillus* species, which are spore-forming, cause anthrax and gastroenteritis. Spore-forming *Clostridium* species are responsible for botulism, tetanus, gas gangrene and pseudomembranous colitis. *Corynebacterium* species cause diphtheria, and *Listeria* species cause meningitis.

Antibacterials that inhibit cell wall synthesis, such as penicillins and cephalosporins, interfere with the linking of the interpeptides of peptidoglycan and weaken the cell wall of both gram positive and gram negative bacteria. Because the peptidoglycans of gram-positive bacteria are exposed, gram-positive bacteria are more susceptible to these antibiotics. Advantageously, eukaryotic cells lack cell walls and are not susceptible to these drugs or other cell wall agents.

Attempts have been made to treat bacterial diseases through the use of bacteriophages. However, the direct introduction of bacteriophages into an animal to prevent or fight diseases has certain drawbacks. Specifically, both the bacteria and the phage have to be in the correct and synchronized growth cycles for the phage to attach. Additionally, there must be the right number of phages to attach to the bacteria; if there are too many or too few phages, there will be either no attachment or no production of the lysing enzyme. The phage must also be active enough. The phages are also inhibited by many things including bacterial debris from the organism it is going to attack. Further complicating the direct use of a bacteriophage to treat bacterial infections is the possibility of immunological reactions, rendering the phage non-functional.

Novel antimicrobial therapy approaches include enzyme-based antibiotics ("enzybiotics") such as bacteriophage lysins. Phages use these lysins to digest the cell wall of their bacterial hosts, releasing viral progeny through hypotonic lysis. A similar outcome results when purified, recombinant lysins are added externally to Gram-positive bacteria. The high lethal activity of lysins against Gram-positive pathogens makes them attractive candidates for development as therapeutics. Bacteriophage lysins were initially proposed for eradicating the nasopharyngeal carriage of pathogenic streptococci (Loeffler, J. M. et al (2001) Science 294:2170-2172; Nelson, D. et al (2001) Proc Natl Acad Sci USA 98:4107-4112). Lysins are part of the lytic mechanism used by double stranded DNA (dsDNA) phage to coordinate host lysis with completion of viral assembly (Wang, I. N. et al (2000) Annu Rev Microbiol 54:799-825). Phage encode both holins that open a pore in the bacterial membrane, and peptidoglycan hydrolases called lysins that break bonds in the bacterial wall [6]. Late in infection, lysin translocates into the cell wall matrix where it rapidly hydrolyzes covalent bonds essential for peptidoglycan integrity, causing bacterial lysis and concomitant progeny phage release.

Lysin family members exhibit a modular design in which a catalytic domain is fused to a specificity or binding domain (Lopez, R. et al (1997) Microb Drug Resist 3:199-211). Lysins can be cloned from viral prophage sequences within bacterial genomes and used for treatment (Beres, S. B. et al (2007) PLoS ONE 2(8):1-14). When added externally, lysins are able to access the bonds of a Gram-positive cell wall (FIG. 1) (Fischetti, V. A. (2008) Curr Opinion Microbiol 11:393-400). Lysins have been shown to demonstrate a high lethal activity against numerous Gram-positive pathogens (especially the bacterium from which they were cloned), raising the possibility of their development as therapeutics (Fischetti, V. A. (2008) Curr Opinion Microbiol 11:393-400; Nelson, D. L. et al (2001) Proc Natl Acad Sci USA 98:4107-4112).

Bacteriophage lytic enzymes have been established as useful in the assessment and specific treatment of various types of infection in subjects through various routes of administration. For example, U.S. Pat. No. 5,604,109 (Fischetti et al.) relates to the rapid detection of Group A streptococci in clinical specimens, through the enzymatic digestion by a semi-purified Group C streptococcal phage associated lysin enzyme. This enzyme work became the basis of additional research, leading to methods of treating diseases. Fischetti and Loomis patents (U.S. Pat. Nos. 5,985,271, 6,017,528 and 6,056,955) disclose the use of a lysin enzyme produced by group C streptococcal bacteria infected with a C1 bacteriophage. U.S. Pat. No. 6,248,324 (Fischetti and Loomis) discloses a composition for dermatological infections by the use of a lytic enzyme in a carrier suitable for topical application to dermal tissues. U.S. Pat. No. 6,254,866 (Fischetti and Loomis) discloses a method for treatment of bacterial infections of the digestive tract which comprises administering a lytic enzyme specific for the infecting bacteria. The carrier for delivering at least one lytic enzyme to the digestive tract is selected from the group consisting of suppository enemas, syrups, or enteric coated pills. U.S. Pat. No. 6,264,945 (Fischetti and Loomis) discloses a method and composition for the treatment of bacterial infections by the parenteral introduction (intramuscularly, subcutaneously, or intravenously) of at least one lytic enzyme produced by a bacteria infected with a bacteriophage specific for that bacteria and an appropriate carrier for delivering the lytic enzyme into a patient.

Phage associated lytic enzymes have been identified and cloned from various bacteriophages, each shown to be effective in killing specific bacterial strains. U.S. Pat. Nos. 7,402,309, 7,638,600 and published PCT Application WO2008/018854 provides distinct phage-associated lytic enzymes useful as antibacterial agents for treatment or reduction of *Bacillus anthracis* infections. U.S. Pat. No. 7,569,223 describes lytic enzymes for *Streptococcus pneumoniae*. Lysin useful for *Enterococcus* (*E. faecalis* and *E. faecium*, including vancomycin resistant strains) are described in U.S. Pat. No. 7,582,291. US 2008/0221035 describes mutant Ply GBS lysins highly effective in killing Group B streptococci. A chimeric lysin denoted ClyS, with activity against Staphylococci bacteria, including *Staphylococcus aureus*, is detailed in WO 2010/002959.

*Streptococcus suis* is a Gram-positive pathogen that infects pigs worldwide. Reports of zoonotic transmission from pigs to humans are increasing (Sriskandan S. et al (2006) PLoS Medicine 3(5):585-567). *S. suis* may develop a consistent presence in human populations in years to come. Humans and pigs have been treated with penicillin or gentamicin, but *S. suis* isolates resistant to these antibiotics exist (Cantin, M. et al (1992) J Vet Diagnostic Investig 4:170-174).

It is evident from the deficiencies and problems associated with current traditional antibacterial agents that there still exists a need in the art for additional specific bacterial agents and also for broader spectrum agents, particularly without high risks of acquired resistance. It is notable that to date, no lysin has been shown to demonstrate broad lytic activity against multiple distinct species of pathogenic and clinically relevant bacteria.

The citation of references herein shall not be construed as an admission that such is prior art to the present invention.

SUMMARY OF THE INVENTION

In its broadest aspect, the present invention provides a lysin having broad killing activity against multiple bacteria, particularly gram-positive bacteria, including *Staphylococcus, Streptococcus, Enterococcus* and *Listeria* bacterial strains. The invention provides a bacteriophage lysin capable of killing bacteria from distinct orders. In an aspect, a lysin polypeptide is provided capable of killing one or more bacteria from distinct orders of Bacilli, particularly order Bacilalles and order Lactobacillales. The present invention provides lysin polypeptide capable of and demonstrated to kill bacteria from two distinct orders, particularly Bacilalles and Lactobacillales, in vitro and in vivo. Lysin of the present invention is capable of killing Bacilalles and Lactobacillales bacteria in mixed culture and in mixed infections in vivo. The invention thus contemplates treatment, decolonization, and/or decontamination of bacteria, cultures or infections or in instances wherein more than one gram positive bacteria, particularly one or more of *Staphylococcus, Streptococcus, Enterococcus* and *Listeria* bacteria, is suspected or present. In particular, the invention contemplates treatment, decolonization, and/or decontamination of bacteria, cultures or infections or in instances wherein more than one type of Bacilalles bacteria, more than one type of Lactobacillales bacteria, or at least one type of Bacilalles and one type of Lactobacillales bacteria is suspected, present, or may be present.

In accordance with the present invention, bacteriophage lysins are provided which are derived from *Streptococcus suis* bacteria. Two exemplary distinct and unique lysins have been isolated and characterized, particularly PlySs1, including an active truncation thereof, and PlySs2. The lysin polypeptides of the present invention are unique in demonstrating broad killing activity against multiple bacteria, particularly gram-positive bacteria, including *Staphylococcus, Streptococcus, Enterococcus* and *Listeria* bacterial strains. In one such aspect, the PlySs2 lysin is capable of killing *Staphylococcus aureus* strains and bacteria in animal models, as demonstrated herein in mice. PlySs2 is effective against antibiotic-resistant *Staphylococcus aureus* such as methicillin-resistant *Staphylococcus aureus* (MRSA), vancomycin intermediate-sensitivity *Staphylococcus aureus* (VISA), and vancomycin resistant *Staphylococcus aureus* (VRSA). In a further such aspect, the PlySs1 lysin is capable of reducing growth of *Staphylococcus aureus* strains and bacteria, including antibiotic-resistant *Staphylococcus aureus* such as methicillin-resistant *Staphylococcus aureus* (MRSA), vancomycin intermediate-sensitivity *Staphylococcus aureus* (VISA), or vancomycin resistant *Staphylococcus aureus* (VRSA). The invention includes compositions and articles of manufacture comprising the lysin polypeptides and methods of prevention and treatment of bacterial growth, colonization and infections.

In an aspect of the invention, a method is provided of killing gram-positive bacteria comprising the step of contacting the bacteria with a composition comprising an amount of an isolated lysin polypeptide effective to kill gram-positive bacteria, the isolated lysin polypeptide comprising the PlySs2 lysin polypeptide or variants thereof effective to kill gram-positive bacteria.

Thus, a method is provided of killing gram-positive bacteria comprising the step of contacting the bacteria with a composition comprising an amount of an isolated lysin polypeptide effective to kill the gram-positive bacteria, the isolated lysin polypeptide comprising the amino acid sequence of SEQ ID NO:3 or variants thereof having at least 80% identity, 85% identity, 90% identity, 95% identity or 99% identity to the polypeptide of SEQ ID NO:3 and effective to kill the gram-positive bacteria.

In an additional aspect of the above method, the composition further comprises an effective amount of the isolated lysin polypeptide comprising the amino acid sequence of SEQ ID NO:1, the isolated lysin polypeptide comprising the amino acid sequence of SEQ ID NO:2, or variants thereof having at least 80% identity to the polypeptide of SEQ ID NO:1 or of SEQ ID NO:2 and effective to kill the gram-positive bacteria.

The invention provides a method of killing gram-positive bacteria comprising the step of contacting the bacteria with a composition comprising an amount of an isolated lysin polypeptide effective to kill gram-positive bacteria, the isolated lysin polypeptide comprising the PlySs1 lysin polypeptide or truncations or variants thereof effective to kill gram-positive bacteria. In an aspect of this method, the composition comprises an effective amount of the isolated lysin polypeptide comprising the amino acid sequence of SEQ ID NO:1, the isolated truncated lysin polypeptide comprising the amino acid sequence of SEQ ID NO:2, or variants thereof having at least 80% identity, 85% identity, 90% identity, 95% identity or 99% identity to the polypeptide of SEQ ID NO:1 or of SEQ ID NO:2 and effective to kill the gram-positive bacteria.

In an aspect of the above methods of killing gram positive bacteria, the methods are performed in vitro or ex vivo so as to sterilize or decontaminate a solution, material or device, particularly intended for use by or in a human.

The invention provides a method for reducing a population of gram-positive bacteria comprising the step of contacting the bacteria with a composition comprising an amount of an isolated polypeptide effective to kill at least a portion of the gram-positive bacteria, the isolated polypeptide comprising the amino acid sequence of SEQ ID NO:3 or variants thereof having at least 80% identity to the polypeptide of SEQ ID NO:3 and effective to kill the gram-positive bacteria. In an embodiment of this method, the composition further comprises an effective amount of the isolated lysin polypeptide comprising the amino acid sequence of SEQ ID NO:1, the isolated lysin polypeptide comprising the amino acid sequence of SEQ ID NO:2, or variants thereof having at least 80% identity to the polypeptide of SEQ ID NO:1 or of SEQ ID NO:2 and effective to kill the gram-positive bacteria.

The invention further provides a method for reducing a population of gram-positive bacteria comprising the step of contacting the bacteria with a composition comprising an amount of an isolated polypeptide effective to kill at least a portion of the gram-positive bacteria, the isolated polypeptide comprising the PlySs1 lysin polypeptide or truncations or variants thereof effective to kill gram-positive bacteria. In an aspect of this method, the composition comprises an effective amount of the isolated lysin polypeptide comprising the amino acid sequence of SEQ ID NO:1, the isolated lysin polypeptide comprising the amino acid sequence of SEQ ID NO:2, or variants thereof having at least 80% identity, 85% identity, 90% identity or 95% identity to the polypeptide of SEQ ID NO:1 or of SEQ ID NO:2 and effective to kill the gram-positive bacteria.

In an aspect of the above methods for reducing a population of gram positive bacteria, the methods are performed in vitro or ex vivo so as to sterilize or decontaminate a solution, material or device, particularly intended for use by or in a human.

The present invention further provides a method for treating an antibiotic-resistant *Staphylococcus aureus* infection in a human comprising the step of administering to a human having an antibiotic-resistant *Staphylococcus aureus* infection, an effective amount of a composition comprising an isolated polypeptide comprising the amino acid sequence of SEQ ID NO:3 or variants thereof having at least 80% identity, 85% identity, 90% identity or 95% identity to the polypeptide of SEQ ID NO:3 and effective to kill *Staphylococcus aureus*, whereby the number of *Staphylococcus aureus* in the human is reduced and the infection is controlled.

In an aspect of this method, the composition may alternatively or may further comprise an effective amount of the isolated lysin polypeptide comprising the amino acid sequence of SEQ ID NO:1, the isolated lysin polypeptide comprising the amino acid sequence of SEQ ID NO:2, or variants thereof having at least 80% identity, 85% identity, 90% identity or 95% identity to the polypeptide of SEQ ID NO:1 or of SEQ ID NO:2 and effective to kill *Staphylococcus aureus*.

A method of the invention also includes a method for treating gram-positive bacterial infection caused by one or more of *Staphylococcus, Streptococcus, Enterococcus* or *Listeria* bacteria in a human comprising the step of administering to a subject having a bacterial infection, an effective amount of a composition comprising an isolated polypeptide comprising the amino acid sequence of SEQ ID NO:3 or variants thereof having at least 80% identity, 85% identity, 90% identity or 95% identity to the polypeptide of SEQ ID NO:3 and effective to kill the gram-positive bacteria, whereby the number of gram-positive bacteria in the human is reduced and the infection is controlled.

The composition of use in the above method may alternatively or may further comprise an effective amount of the isolated lysin polypeptide comprising the amino acid sequence of SEQ ID NO:1, the isolated lysin polypeptide comprising the amino acid sequence of SEQ ID NO:2, or variants thereof having at least 80% identity, 85% identity, 90% identity or 95% identity to the polypeptide of SEQ ID NO:1 or of SEQ ID NO:2 and effective to kill the gram-positive bacteria.

The invention additionally includes a method for treating a human subject exposed to or at risk for exposure to a pathogenic gram-positive bacteria comprising the step of administering to the subject a composition comprising an amount of an isolated lysin polypeptide effective to kill the gram-positive bacteria, the isolated lysin polypeptide comprising the amino acid sequence of SEQ ID NO:3 or variants thereof having at least 80% identity, 85% identity, 90% identity or 95% identity to the polypeptide of SEQ ID NO:3 and effective to kill the gram-positive bacteria. In a particular aspect of this method, wherein the subject is exposed to or at risk of one of or one or more of *Staphylococcus* (such as *Staphylococcus aureus*), *Streptococcus* (such as *Streptococcus pyogenes*), *Listeria* (such as *L. monocytogenes*), or *Enterococcus* (such as *E. faecalis*) bacteria. The subject may be a human. The subject may be a human adult, child, infant or fetus.

Variants of a lysin polypeptide of use in the compositions and methods of the invention may be substantially identical to one or more of the lysin polypeptide(s) exemplified herein, including to SEQ ID NO: 1, 2 or 3. Variants of a lysin polypeptide of use in the compositions and methods of the invention may have at least 75% identity, at least 80% identity, at least 90% identity, at least 95% identity in amino acid sequence as compared to the lysin polypeptide(s) exemplified herein, including to SEQ ID NO: 1, 2 or 3.

In any such above method or methods, the susceptible, killed or treated bacteria may be selected from *Staphylococcus aureus, Listeria monocytogenes, Staphylococcus simulans, Streptococcus suis, Staphylococcus epidermidis, Streptococcus equi, Streptococcus equi zoo, Streptococcus agalactiae* (GBS), *Streptococcus pyogenes* (GAS), *Streptococcus sanguinis, Streptococcus gordonii, Streptococcus dysgalactiae*, Group G *Streptococcus*, Group E *Streptococcus, Enterococcus faecalis* and *Streptococcus pneumonia*.

In accordance with any of the methods of the invention, the susceptible bacteria or bacteria being treated or decolonized may be an antibiotic resistant bacteria. The bacteria may be methicillin-resistant *Staphylococcus aureus* (MRSA), vancomycin intermediate-sensitivity *Staphylococcus aureus* (VISA), or vancomycin resistant *Staphylococcus aureus* (VRSA). The susceptible bacteria may be a clinically relevant or pathogenic bacteria, particularly for humans. In an aspect of the method(s), the lysin polypeptide(s) is effective to kill *Staphylococcus, Streptococcus, Enterococcus* and *Listeria* bacterial strains.

In accordance with any of the methods of the invention, the composition thereof may further comprise a carrier, including a pharmaceutically acceptable carrier, additive or diluent. In accordance with any of the methods of the invention, the composition thereof may further comprise a suitable vehicle for delivery of the polypeptide to a site of infection. In accordance with any of the methods of the invention, the composition thereof may further comprise one or more antibiotic.

The invention provides compositions, including therapeutic and pharmaceutical compositions comprising one or more lysin polypeptide of the invention.

The invention thus provides a pharmaceutical composition for killing gram-positive bacteria comprising the isolated lysin polypeptide comprising the amino acid sequence of SEQ ID NO:3 or variants thereof having at least 80% identity to the polypeptide of SEQ ID NO:3 and effective to kill the gram-positive bacteria.

In an embodiment, the pharmaceutical composition may alternatively or may further comprise an effective amount of the isolated lysin polypeptide comprising the amino acid sequence of SEQ ID NO:1, the isolated lysin polypeptide comprising the amino acid sequence of SEQ ID NO:2, or variants thereof having at least 80% identity to the polypeptide of SEQ ID NO:1 or of SEQ ID NO:2 and effective to kill the gram-positive bacteria.

In an aspect of the invention, a pharmaceutical composition is provided for killing gram-positive bacteria comprising at least two isolated lysin polypeptides wherein the first isolated polypeptide comprises the amino acid sequence of SEQ ID NO:3 or variants thereof having at least 80% identity to the polypeptide of SEQ ID NO:3 and effective to kill the gram-positive bacteria, and the second isolated polypeptide comprises the amino acid sequence of SEQ ID NO:1, the isolated lysin polypeptide comprising the amino acid sequence of SEQ ID NO:2, or variants thereof having at least 80% identity to the polypeptide of SEQ ID NO:1 or of SEQ ID NO:2 and effective to kill the gram-positive bacteria.

In a further aspect thereof, a composition, including a therapeutic or pharmaceutical composition, may comprise a truncated lysin having the amino acid sequence of SEQ ID NO: 2 with a modification whereby the truncated lysin comprises only one catalytic domain selected from the group consisting of an endopeptidase domain and a glucosaminidase domain. In an additional aspect of the composition, the truncated lysin does not include the glucosaminidase domain of SEQ ID NO:1. The truncated lysin may particularly have the amino acid sequence of SEQ ID NO:2, or variants thereof having at least 80% identity to the polypeptide of SEQ ID NO:2 and effective to kill gram-positive bacteria.

The invention includes an article of manufacture comprising a vessel containing a composition comprising an isolated polypeptide comprising the amino acid sequence of SEQ ID NO:3, or variants thereof having at least 80% identity, 85% identity, 90% identity or 95% identity to the polypeptide of SEQ ID NO:3 and effective to kill gram-positive bacteria, and instructions for use of the composition in treatment of a patient exposed to or exhibiting symptoms consistent with exposure to *Staphylococcus, Streptococcus* or *Listeria* bacteria, where the instructions for use of the composition indicate a method for using the composition, the method comprising the steps of:

a) identifying the patient suspected of having been exposed to *Staphylococcus, Streptococcus* or *Listeria* bacteria; and b) administering an effective amount of the composition to the patient.

In one aspect of the article of the invention, the isolated polypeptide of the composition has the amino acid sequence of SEQ ID NO:3. In an additional aspect of the article of the invention, the composition alternatively or further comprises an isolated polypeptide comprising the amino acid sequence of SEQ ID NO:1, the amino acid sequence of SEQ ID NO:2, or variants thereof having at least 80% identity, 85% identity, 90% identity or 95% identity to the polypeptide of SEQ ID NO:1 or of SEQ ID NO:2 and effective to kill gram-positive bacteria.

The compositions of the invention may particularly demonstrate or have killing activity against one or more bacteria strains, particularly selected from the group consisting of *Staphylococcus aureus, Listeria monocytogenes, Staphylococcus simulans, Streptococcus suis, Staphylococcus epidermidis, Streptococcus equi, Streptococcus equi zoo, Streptococcus agalactiae* (GBS), *Streptococcus pyogenes* (GAS), *Streptococcus sanguinis, Streptococcus gordonii, Streptococcus dysgalactiae*, Group G *Streptococcus*, Group E *Streptococcus, Enterococcus faecalis* and *Streptococcus pneumonia*.

The present invention also provides nucleic acids encoding the lysin polypeptides of the invention. Thus, nucleic acids are provided encoding *S. suis* lysins PlySs1, truncated or whole lysin, and PlySs2. Exemplary nucleic acid sequences are provided in FIG. 3 and in FIG. 4. Nucleic acids capable of encoding a polypeptide of SEQ ID NO:1, SEQ ID NO:2 or SEQ ID NO:3, including variants thereof are provided herein.

The present invention also relates to a recombinant DNA molecule or cloned gene, or a degenerate variant thereof, which encodes an *S. suis* lysin or lysin polypeptide; preferably a nucleic acid molecule, in particular a recombinant DNA molecule or cloned gene, encoding the PlySs1 lysin polypeptide, truncated or whole lysin, and/or the PlySs2 lysin polypeptide, has a nucleotide sequence or is complementary to a DNA sequence shown in FIG. 3 and in FIG. 4.

In a further embodiment of the invention, the full DNA sequence of the recombinant DNA molecule, cloned gene, or nucleic acid sequence encoding a lysin polypeptide hereof may be operatively linked to an expression control sequence which may be introduced into an appropriate host. The invention accordingly extends to unicellular hosts, including bacterial hosts, transformed with the nucleic acid sequence, cloned gene or recombinant DNA molecule comprising a DNA sequence encoding the present lysin polypeptide(s), and more particularly, the complete DNA sequence determined from the sequences set forth above and in FIG. 3 and FIG. 4.

The present invention naturally contemplates several means for preparation of the lysin polypeptide(s), including as illustrated herein known recombinant techniques, and the invention is accordingly intended to cover such synthetic preparations within its scope. The isolation of the DNA and amino acid sequences disclosed herein facilitates the reproduction of the lysin polypeptide(s) by such recombinant techniques, and accordingly, the invention extends to expression vectors prepared from the disclosed DNA sequences for expression in host systems by recombinant DNA techniques, and to the resulting transformed hosts.

According to other preferred features of certain embodiments of the present invention, a recombinant expression system is provided to produce biologically active lysin polypeptide(s). A process for preparation of the polypeptides, particularly one or more lysin polypeptide of the invention, is provided comprising culturing a host cell containing an expression vector encoding one or more lysin polypeptide(s) of the invention or capable of expressing a lysin polypeptide(s) of the invention, and recovering the polypeptide(s).

The diagnostic utility of the present invention extends to the use of the present lysin polypeptides in assays to screen for the presence of gram-positive bacteria, to screen for the presence of susceptible gram-positive bacteria, or to determine the susceptibility of bacteria to killing or lysing by a one or more lysin polypeptide(s) of the invention.

The present invention extends to the development of antibodies against the lysin polypeptide(s), or alternatively against the cleavage target of the lysin polypeptide, including naturally raised and recombinantly prepared antibodies. Such antibodies could include both polyclonal and monoclonal antibodies prepared by known genetic techniques, as well as bi-specific (chimeric) antibodies, and antibodies including other functionalities suiting them for additional diagnostic use conjunctive with their capability of modulating lysin activity.

Lysin polypeptides which are modified and are chimeric or fusion proteins, or which are labeled, are contemplated and provided herein. In a chimeric or fusion protein, the lysin polypeptide(s) of the invention may be covalently attached to an entity which may provide additional function or enhance the use or application of the lysin polypeptide(s), including for instance a tag, label, targeting moiety or ligand, a cell binding or cell recognizing motif or agent, an antibacterial agent, an antibody, an antibiotic. Exemplary labels include a radioactive label, such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re. The label may be an enzyme, and detection of the labeled lysin polypeptide may be accomplished by any of the presently utilized or accepted colorimetric, spectrophotometric, fluorospectrophotometric, amperometric or gasometric techniques known in the art.

Other objects and advantages will become apparent to those skilled in the art from a review of the following description which proceeds with reference to the following illustrative drawings.

BRIEF DESCRIPTION OF THE DRAWINGS

FIGS. 3A, 3B and 3C provides the (A) nucleotide (SEQ ID NO: 11) and (B) amino acid sequence of the lysin PlySs1 as well as a (C) protein domain analysis. The amino acid sequence of the full length PlySs1 (SEQ ID NO:1) and truncated PlySs1 (SEQ ID NO:2) are provided. The endopeptidase domain (SEQ ID NO:6), dual CPL-7 domain (SEQ ID NO:7) and glucosaminidase domain (SEQ ID NO:8) are denoted.

FIGS. 4A, 4B and 4C provides the (A) nucleotide (SEQ ID NO: 12) and (B) amino acid sequence of the lysin e PlySs2 as well as a (C) protein domain analysis. The amino acid sequence of PlySs2 corresponds to SEQ ID NO:3. The CHAP domain and the SH-3 domain of the PlySs2 lysin are shaded, with the CHAP domain starting with LNN . . . and ending with . . . YIT (SEQ ID NO:4) and the SH-3 domain starting with RSY . . . and ending with . . . VAT (SEQ ID NO:5).

FIG. 27 depicts the minimum inhibitory concentration (MIC) of PlySs2 for various Gram-positive bacteria. There was a low MIC for MRSA MW2, as expected, and a higher MIC for *S. pyogenes* 5005. The MIC of PlySs2 correlates to the lytic activity and bactericidal tests. The MIC of PlySs2 for the negative control *E. coli* was accordingly immeasurable.

FIG. 30 provides PlySs2 enzymatic domain alignment to PlyC. The CHAP domains of the streptococcal lysins PlySs2 (SEQ ID NO:13) and PlyC (SEQ ID NO: 14) (subunit A, GenBank no. AAP42310) are aligned. Amino-acid identities are indicated with underlying asterisks and highlighting. The positions of the presumptive catalytic residues (cysteine and histidine, for which the domain is named is named) are indicated with arrows.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions as provided and set out below and in this section.

Figure 3C:
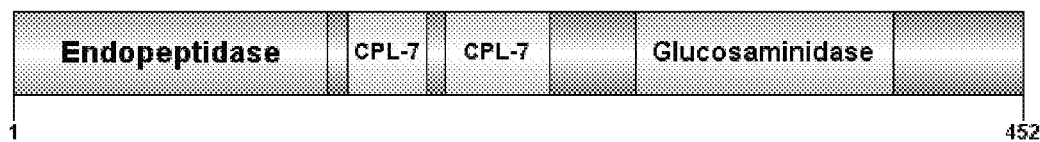
Figure 4C:
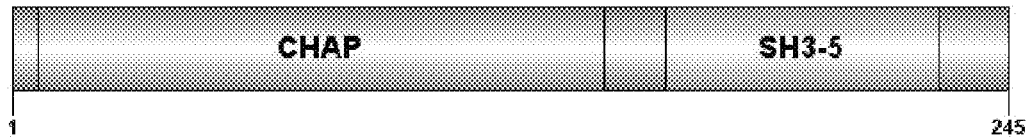

The terms "*S. suis* lysin(s)", "PlySs lysin(s)", "PlySs1 lysin", "PlySs1", "whole PlySs1", "truncated PlySs1", "ΔPlySs1", "PlySs2 lysin", "PlySs2" and any variants not specifically listed, may be used herein interchangeably, and as used throughout the present application and claims refer to proteinaceous material including single or multiple proteins, and extends to those proteins having the amino acid sequence data described herein and presented in FIG. 3 and in FIG. 4 (SEQ ID NOS: 1, 2 and/or 3), and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "*S. suis* lysin(s)", "PlySs lysin(s)", "PlySs1 lysin", "PlySs1", "whole PlySs1", "truncated PlySs1", "ΔPlySs1", "PlySs2 lysin", "PlySs2" are intended to include within their scope proteins specifically recited herein as well as all substantially homologous analogs, fragments or truncations, and allelic variations.

Polypeptides and Lytic Enzymes

A "lytic enzyme" includes any bacterial cell wall lytic enzyme that kills one or more bacteria under suitable conditions and during a relevant time period. Examples of lytic enzymes include, without limitation, various amidase cell wall lytic enzymes.

A "*S. suis* lytic enzyme" includes a lytic enzyme that is capable of killing at least one or more *Streptococcus suis* bacteria under suitable conditions and during a relevant time period.

A "bacteriophage lytic enzyme" refers to a lytic enzyme extracted or isolated from a bacteriophage or a synthesized lytic enzyme with a similar protein structure that maintains a lytic enzyme functionality.

A lytic enzyme is capable of specifically cleaving bonds that are present in the peptidoglycan of bacterial cells to disrupt the bacterial cell wall. It is also currently postulated that the bacterial cell wall peptidoglycan is highly conserved among most bacteria, and cleavage of only a few bonds to may disrupt the bacterial cell wall. The bacteriophage lytic enzyme may be an amidase, although other types of enzymes are possible. Examples of lytic enzymes that cleave these bonds are various amidases such as muramidases, glucosaminidases, endopeptidases, or N-acetyl-muramoyl-L-alanine amidases. Fischetti et al (1974) reported that the C1 streptococcal phage lysin enzyme was an amidase. Garcia et al (1987, 1990) reported that the Cpl lysin from a *S. pneumoniae* from a Cp-1 phage was a lysozyme. Caldentey and Bamford (1992) reported that a lytic enzyme from the phi 6 *Pseudomonas* phage was an endopeptidase, splitting the peptide bridge formed by melo-diammopimilic acid and D-alanine. The *E. coli* T1 and T6 phage lytic enzymes are amidases as is the lytic enzyme from *Listeria* phage (ply) (Loessner et al, 1996). There are also other lytic enzymes known m the art that are capable of cleaving a bacterial cell wall.

A "lytic enzyme genetically coded for by a bacteriophage" includes a polypeptide capable of killing a host bacteria, for instance by having at least some cell wall lytic activity against the host bacteria. The polypeptide may have a sequence that encompasses native sequence lytic enzyme and variants thereof. The polypeptide may be isolated from a variety of sources, such as from a bacteriophage ("phage"), or prepared by recombinant or synthetic methods, such as those described by Garcia et al and also as provided herein. The polypeptide may comprise a choline-binding portion at the carboxyl terminal side and may be characterized by an enzyme activity capable of cleaving cell wall peptidoglycan (such as amidase activity to act on amide bonds in the peptidoglycan) at the amino terminal side. Lytic enzymes have been described which include multiple enzyme activities, for example two enzymatic domains, such as PlyGBS lysin. Generally speaking, a lytic enzyme may be between 25,000 and 35,000 daltons m molecular weight and comprise a single polypeptide chain; however, this can vary depending on the enzyme chain. The molecular weight most conveniently can be determined by assay on denaturing sodium dodecyl sulfate gel electrophoresis and comparison with molecular weight markers.

"A native sequence phage associated lytic enzyme" includes a polypeptide having the same amino acid sequence as an enzyme derived from a bacteria. Such native sequence enzyme can be isolated or can be produced by recombinant or synthetic means.

The term "native sequence enzyme" encompasses naturally occurring forms (e.g., alternatively spliced or altered forms) and naturally-occurring variants of the enzyme. In one embodiment of the invention, the native sequence enzyme is a mature or full-length polypeptide that is genetically coded for by a gene from a bacteriophage specific for Streptococcus suis. Of course, a number of variants are possible and known, as acknowledged in publications such as Lopez et al., Microbial Drug Resistance 3: 199-211 (1997); Garcia et al., Gene 86: 81-88 (1990); Garcia et al., Proc. Natl. Acad. Sci. USA 85: 914-918 (1988); Garcia et al., Proc. Natl. Acad. Sci. USA 85: 914-918 (1988); Garcia et al., Streptococcal Genetics (J. J. Ferretti and Curtis eds., 1987); Lopez et al., FEMS Microbiol. Lett. 100: 439-448 (1992); Romero et al., J. Bacteriol. 172. 5064-5070 (1990); Ronda et al., Eur. J. Biochem. 164: 621-624 (1987) and Sanchez et al., Gene 61: 13-19 (1987). The contents of each of these references, particularly the sequence listings and associated text that compares the sequences, including statements about sequence homologies, are specifically incorporated by reference in their entireties.

"A variant sequence lytic enzyme" includes a lytic enzyme characterized by a polypeptide sequence that is different from that of a lytic enzyme, but retains functional activity. The lytic enzyme can, in some embodiments, be genetically coded for by a bacteriophage specific for Streptococcus suis having a particular amino acid sequence identity with the lytic enzyme sequence(s) hereof, as provided in FIG. 3 and FIG. 4 or in any of SEQ ID NOS: 1, 2 or 3. For example, in some embodiments, a functionally active lytic enzyme can kill Streptococcus suis bacteria, and other susceptible bacteria as provided herein, including as shown in TABLE 1 and in FIGS. 9 and 10, by disrupting the cellular wall of the bacteria. An active lytic enzyme may have a 60, 65, 70, 75, 80, 85, 90, 95, 97, 98, 99 or 99.5% amino acid sequence identity with the lytic enzyme sequence(s) hereof, as provided in FIG. 3 and FIG. 4 or m any of SEQ ID NOS: 1, 2 or 3. Such phage associated lytic enzyme variants include, for instance, lytic enzyme polypeptides wherein one or more amino acid residues are added, or deleted at the N or C terminus of the sequence of the lytic enzyme sequence(s) hereof, as provided in FIG. 3 and FIG. 4 or in any of SEQ ID NOS: 1, 2 or 3. In a particular aspect, a phage associated lytic enzyme will have at least about 80% or 85% amino acid sequence identity with native phage associated lytic enzyme sequences, particularly at least about 90% (e.g. 90%) amino acid sequence identity. Most particularly a phage associated lytic enzyme variant will have at least about 95% (e.g. 95%) amino acid sequence identity with the native phage associated the lytic enzyme sequence(s) hereof, as provided in FIG. 3 and FIG. 4 or m any of SEQ ID NOS 1, 2 or 3.

"Percent amino acid sequence identity" with respect to the phage associated lytic enzyme sequences identified is defined herein as the percentage of amino acid residues in a candidate sequence that are identical with the amino acid residues in the phage associated lytic enzyme sequence, after aligning the sequences in the same reading frame and introducing gaps, if necessary, to achieve the maximum percent sequence identity, and not considering any conservative substitutions as part of the sequence identity.

"Percent nucleic acid sequence identity" with respect to the phage associated lytic enzyme sequences identified herein is defined as the percentage of nucleotides in a candidate sequence that are identical with the nucleotides in the phage associated lytic enzyme sequence, after aligning the sequences and introducing gaps, if necessary, to achieve the maximum percent sequence identity.

To determine the percent identity of two nucleotide or amino acid sequences, the sequences are aligned for optimal comparison purposes (e.g., gaps may be introduced in the sequence of a first nucleotide sequence). The nucleotides or amino acids at corresponding nucleotide or amino acid positions are then compared. When a position in the first sequence is occupied by the same nucleotide or amino acid as the corresponding position m the second sequence, then the molecules are identical at that position. The percent identity between the two sequences is a function of the number of identical positions shared by the sequences (i.e., % identity=# of identical positions/total # of positions.times.100).

The determination of percent identity between two sequences may be accomplished using a mathematical algorithm. A preferred, non-limiting example of a mathematical algorithm utilized for the comparison of two sequences is the algorithm of Karlin et al., Proc. Natl. Acad. Sci. USA, 90:5873-5877 (1993). Such an algorithm is incorporated into the NBLAST program which may be used to identify sequences having the desired identity to nucleotide sequences of the invention. To obtain gapped alignments for comparison purposes, Gapped BLAST may be utilized as described in Altschul et al., Nucleic Acids Res, 25:3389-3402 (1997). When utilizing BLAST and Gapped BLAST programs, the default parameters of the respective programs (e.g., NBLAST) may be used. See the programs provided by National Center for Biotechnology Information, National Library of Medicine, National Institutes of Health. In one embodiment, parameters for sequence comparison may be set at W=12. Parameters may also be varied (e.g., W=5 or W=20). The value "W" determines how many continuous nucleotides must be identical for the program to identify two sequences as containing regions of identity.

"Polypeptide" includes a polymer molecule comprised of multiple amino acids joined in a linear manner. A polypeptide can, in some embodiments, correspond to molecules encoded by a polynucleotide sequence which is naturally occurring. The polypeptide may include conservative substitutions where the naturally occurring amino acid is replaced by one having similar properties, where such conservative substitutions do not alter the function of the polypeptide (see, for example, Lewin "Genes V" Oxford University Press Chapter 1, pp. 9-13 1994).

The term "altered lytic enzymes" includes shuffled and/or chimeric lytic enzymes.

Phage lytic enzymes specific for bacteria infected with a specific phage have been found to effectively and efficiently break down the cell wall of the bacterium in question. The lytic enzyme is believed to lack proteolytic enzymatic activity and is therefore non-destructive to mammalian proteins and tissues when present during the digestion of the bacterial cell wall. As shown by Loeffler et al., "Rapid Killing of Streptococcus pneumoniae with a Bacteriophage Cell Wall Hydrolase," Science, 294: 2170-2172 (Dec. 7, 2001), and supplemental material thereto published online by Science magazine, which are incorporated herein by reference in their entirety, a purified pneumococcal bacteriophage lytic enzyme, such as Pal, is able to kill various pneumococci. Loeffler et al. have shown through these experiments that within seconds after contact, the lytic enzyme Pal is able to kill 15 clinical stains of *S. pneumoniae*, including the most frequently isolated serogroups and penicillin resistant stains, in vitro. Treatment of mice with Pal was also able to eliminate or significantly reduce nasal carriage of serotype 14 in a dose-dependent manner. Furthermore, because it has been found that the action of Pal, like other phage lytic enzymes, but unlike antibiotics, was rather specific for the target pathogen, it is likely that the normal flora will remain essentially intact (M. J. Loessner, G. Wendlinger, S. Scherer, Mol Microbiol 16, 1231-41. (1995) incorporated herein by reference). In contrast, lysin polypeptide of the present invention has a remarkably broad and clinically significant bacterial killing profile. As demonstrated herein, for example, the isolated *S. suis* lysin PlySs2, is effective in killing *S. suis*, and also various other *Streptococcus* strains, including Group B *Streptococcus* (GBS), Staphylococcal strains, including *Staphylococcus aureus, Enterococcus* and *Listeria*. The lysin of the present invention thus demonstrates a breadth of bacterial cell killing unlike any lysin previously reported or contemplated.

A lytic enzyme or polypeptide of the invention may be produced by the bacterial organism after being infected with a particular bacteriophage as either a prophylactic treatment for preventing those who have been exposed to others who have the symptoms of an infection from getting sick, or as a therapeutic treatment for those who have already become ill from the infection. In as much the lysin polypeptide sequences and nucleic acids encoding the lysin polypeptides are provided herein, the lytic enzyme(s)/polypeptide(s) may be preferably produced via the isolated gene for the lytic enzyme from the phage genome, putting the gene into a transfer vector, and cloning said transfer vector into an expression system, using standard methods of the art, including as exemplified herein. The lytic enzyme(s) or polypeptide(s) may be truncated, chimeric, shuffled or "natural," and may be in combination. Relevant U.S. Pat. No. 5,604,109 is incorporated herein in its entirety by reference. An "altered" lytic enzyme can be produced in a number of ways. In a preferred embodiment, a gene for the altered lytic enzyme from the phage genome is put into a transfer or movable vector, preferably a plasmid, and the plasmid is cloned into an expression vector or expression system. The expression vector for producing a lysin polypeptide or enzyme of the invention may be suitable for *E. coli, Bacillus*, or a number of other suitable bacteria. The vector system may also be a cell free expression system. All of these methods of expressing a gene or set of genes are known in the art. The lytic enzyme may also be created by infecting *Streptococcus suis* with a bacteriophage specific for *Streptococcus suis*, wherein said at least one lytic enzyme exclusively lyses the cell wall of said *Streptococcus suis* having at most minimal effects on other, for example natural or commensal, bacterial flora present.

A "chimeric protein" or "fusion protein" comprises all or (preferably a biologically active) part of a polypeptide of the invention operably linked to a heterologous polypeptide. Chimeric proteins or peptides are produced, for example, by combining two or more proteins having two or more active sites. Chimeric protein and peptides can act independently on the same or different molecules, and hence have a potential to treat two or more different bacterial infections at the same time. Chimeric proteins and peptides also may be used to treat a bacterial infection by cleaving the cell wall in more than one location, thus potentially providing more rapid or effective (or synergistic) killing from a single lysin molecule or chimeric peptide.

A "heterologous" region of a DNA construct or peptide construct is an identifiable segment of DNA within a larger DNA molecule or peptide within a larger peptide molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA or peptide as defined herein.

The term "operably linked" means that the polypeptide of the disclosure and the heterologous polypeptide are fused in-frame. The heterologous polypeptide can be fused to the N-terminus or C-terminus of the polypeptide of the disclosure. Chimeric proteins are produced enzymatically by chemical synthesis, or by recombinant DNA technology. A number of chimeric lytic enzymes have been produced and studied. Gene E-L, a chimeric lysis constructed from bacteriophages phi X174 and MS2 lysis proteins E and L, respectively, was subjected to internal deletions to create a series of new E-L clones with altered lysis or killing properties. The lytic activities of the parental genes E, L, E-L, and the internal truncated forms of E-L were investigated in this study to characterize the different lysis mechanism, based on differences in the architecture of the different membranes spanning domains. Electron microscopy and release of marker enzymes for the cytoplasmic and periplasmic spaces revealed that two different lysis mechanisms can be distinguished depending on penetration of the proteins of either the inner membrane or the inner and outer membranes of the *E. coli* (FEMS Microbiol. Lett. (1998) 164(1):159-67 (incorporated herein by reference). One example of a useful fusion protein is a GST fusion protein in which the polypeptide of the disclosure is fused to the C-terminus of a GST sequence. Such a chimeric protein can facilitate the purification of a recombinant polypeptide of the disclosure.

In another embodiment, the chimeric protein or peptide contains a heterologous signal sequence at its N-terminus. For example, the native signal sequence of a polypeptide of the disclosure can be removed and replaced with a signal sequence from another protein. For example, the gp67 secretory sequence of the baculovirus envelope protein can be used as a heterologous signal sequence (Current Protocols in Molecular Biology, Ausubel et al., eds., John Wiley & Sons, 1992, incorporated herein by reference). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

The fusion protein may combine a lysin polypeptide with a protein or polypeptide of having a different capability, or providing an additional capability or added character to the lysin polypeptide. The fusion protein may be an immunoglobulin fusion protein in which all or part of a polypeptide of the disclosure is fused to sequences derived from a member of the immunoglobulin protein family. The immunoglobulin may be an antibody, for example an antibody directed to a surface protein or epitope of a susceptible or target bacteria. An immunoglobulin fusion protein can be incorporated into a pharmaceutical composition and administered to a subject to inhibit an interaction between a ligand (soluble or membrane-bound) and a protein on the surface of a cell (receptor), to thereby suppress signal transduction in vivo. The immunoglobulin fusion protein can alter bioavailability of a cognate ligand of a polypeptide of the disclosure. Inhibition of ligand/receptor interaction may be useful therapeutically, both for treating bacterial-associated diseases and disorders for modulating (i.e. promoting or inhibiting) cell survival. Moreover, an immunoglobulin fusion protein of the disclosure can be used as an immunogen to produce antibodies directed against a polypeptide of the disclosure in a subject, to purify ligands and m screening assays to identify molecules which inhibit the interaction of receptors with ligands. Chimeric and fusion proteins and peptides of the disclosure can be produced by standard recombinant DNA techniques.

The fusion gene can be synthesized by conventional techniques, including automated DNA synthesizers. Alternatively, PCR amplification of gene fragments can be carried out using anchor primers which give rise to complementary overhangs between two consecutive gene fragments which subsequently can be annealed and reamplified to generate a chimeric gene sequence (see, i.e., Ausubel et al., supra). Moreover, many expression vectors are commercially available that already encode a fusion moiety (i.e., a GST polypeptide). A nucleic acid encoding a polypeptide of the invention can be cloned into such an expression vector such that the fusion moiety is linked in-frame to the polypeptide of the invention.

As used herein, shuffled proteins or peptides, gene products, or peptides for more than one related phage protein or protein peptide fragments have been randomly cleaved and reassembled into a more active or specific protein. Shuffled oligonucleotides, peptides or peptide fragment molecules are selected or screened to identify a molecule having a desired functional property. This method is described, for example, in Stemmer, U.S. Pat. No. 6,132,970 (Method of shuffling polynucleotides); Kauffman, U.S. Pat. No. 5,976,862 (Evolution via Condon-based Synthesis) and Huse, U.S. Pat. No. 5,808,022 (Direct Codon Synthesis). The contents of these patents are incorporated herein by reference. Shuffling can be used to create a protein that is more active, for instance up to 10 to 100 fold more active than the template protein. The template protein is selected among different varieties of lysin proteins. The shuffled protein or peptides constitute, for example, one or more binding domains and one or more catalytic domains. Each binding or catalytic domain is derived from the same or a different phage or phage protein. The shuffled domains are either oligonucleotide based molecules, as gene or gene products, that either alone or in combination with other genes or gene products are translatable into a peptide fragment, or they are peptide based molecules. Gene fragments include any molecules of DNA, RNA, DNA-RNA hybrid, antisense RNA, Ribozymes, ESTs, SNIPs and other oligonucleotide-based molecules that either alone or in combination with other molecules produce an oligonucleotide molecule capable or incapable of translation into a peptide.

The modified or altered form of the protein or peptides and peptide fragments, as disclosed herein, includes protein or peptides and peptide fragments that are chemically synthesized or prepared by recombinant DNA techniques, or both. These techniques include, for example, chimerization and shuffling. When the protein or peptide is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

A signal sequence of a polypeptide can facilitate transmembrane movement of the protein and peptides and peptide fragments of the disclosure to and from mucous membranes, as well as by facilitating secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the disclosure can pertain to the described polypeptides having a signal sequence, as well as to the signal sequence itself and to the polypeptide in the absence of the signal sequence (i.e., the cleavage products). A nucleic acid sequence encoding a signal sequence of the disclosure can be operably linked in an expression vector to a protein of interest, such as a protein which is ordinarily not secreted or is otherwise difficult to isolate. The signal sequence directs secretion of the protein, such as from an eukaryotic host into which the expression vector is transformed, and the signal sequence is subsequently or concurrently cleaved. The protein can then be readily purified from the extracellular medium by art-recognized methods. Alternatively, the signal sequence can be linked to a protein of interest using a sequence which facilitates purification, such as with a GST domain.

The present invention also pertains to other variants of the polypeptides of the invention. Such variants may have an altered amino acid sequence which can function as either agonists (mimetics) or as antagonists. Variants can be generated by mutagenesis, i.e., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein. Variants of a protein of the disclosure which function as either agonists (mimetics) or as antagonists can be identified by screening combinatorial libraries of mutants, i.e., truncation mutants, of the protein of the disclosure for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (i.e., for phage display). There are a variety of methods which can be used to produce libraries of potential variants of the polypeptides of the disclosure from a degenerate oligonucleotide sequence. Methods for synthesizing degenerate oligonucleotides are known in the art (see, i.e., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477, all herein incorporated by reference).

In addition, libraries of fragments of the coding sequence of a polypeptide of the disclosure can be used to generate a variegated population of polypeptides for screening and subsequent selection of variants, active fragments or truncations. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest. Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions m which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the disclosure (Arkin and Yourvan (1992) Proc. Natl. Acad. Sci. USA 89:7811-7815; Delgrave et al. (1993) Protein Engineering 6(3):327-331) immunologically active portions of a protein or peptide fragment include regions that bind to antibodies that recognize the phage enzyme. In this context, the smallest portion of a protein (or nucleic acid that encodes the protein) according to embodiments is an epitope that is recognizable as specific for the phage that makes the lysin protein. Accordingly, the smallest polypeptide (and associated nucleic acid that encodes the polypeptide) that can be expected to bind a target or receptor, such as an antibody, and is useful for some embodiments may be 8, 9, 10, 11, 12, 13, 15, 20, 25, 30, 35, 40, 45, 50, 55, 60, 65, 75, 85, or 100 amino acids long. Although small sequences as short as 8, 9, 10, 11, 12 or 15 amino acids long reliably comprise enough structure to act as targets or epitopes, shorter sequences of 5, 6, or 7 amino acids long can exhibit target or epitopic structure in some conditions and have value in an embodiment. Thus, the smallest portion of the protein(s) or lysin polypeptides provided herein, including as set out in FIGS. 3 and 4 and in SEQ ID NOS: 1, 2 and/or 3, includes polypeptides as small as 5, 6, 7, 8, 9, 10, 12, 14 or 16 amino acids long.

Biologically active portions of a protein or peptide fragment of the embodiments, as described herein, include polypeptides comprising amino acid sequences sufficiently identical to or derived from the amino acid sequence of the phage protein of the disclosure, which include fewer amino acids than the full length protein of the phage protein and exhibit at least one activity of the corresponding full-length protein. Typically, biologically active portions comprise a domain or motif with at least one activity of the corresponding protein. A biologically active portion of a protein or protein fragment of the disclosure can be a polypeptide which is, for example, 10, 25, 50, 100 less or more amino acids in length. Moreover, other biologically active portions, in which other regions of the protein are deleted, or added can be prepared by recombinant techniques and evaluated for one or more of the functional activities of the native form of a polypeptide of the embodiments.

Homologous proteins and nucleic acids can be prepared that share functionality with such small proteins and/or nucleic acids (or protein and/or nucleic acid regions of larger molecules) as will be appreciated by a skilled artisan. Such small molecules and short regions of larger molecules that may be homologous specifically are intended as embodiments. Preferably the homology of such valuable regions is at least 50%, 65%, 75%, 80%, 85%, and preferably at least 90%, 95%, 97%, 98%, or at least 99% compared to the lysin polypeptides provided herein, including as set out in FIGS. 3 and 4 and in SEQ ID NOS: 1, 2 and/or 3. These percent homology values do not include alterations due to conservative amino acid substitutions.

Two amino acid sequences are "substantially homologous" when at least about 70% of the amino acid residues (preferably at least about 80%, at least about 85%, and preferably at least about 90 or 95%) are identical, or represent conservative substitutions. The sequences of comparable lysins, such as comparable PlySs2 lysins, or comparable PlySs1 lysins, are substantially homologous when one or more, or several, or up to 10%, or up to 15%, or up to 20% of the amino acids of the lysin polypeptide are substituted with a similar or conservative amino acid substitution, and wherein the comparable lysins have the profile of activities, anti-bacterial effects, and/or bacterial specificities of a lysin, such as the PlySs2 and/or PlySs1 lysins, disclosed herein.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |

-continued

TABLE OF CORRESPONDENCE

| SYMBOL | | |
|---|---|---|
| 1-Letter | 3-Letter | AMINO ACID |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

Mutations can be made in the amino acid sequences, or in the nucleic acid sequences encoding the polypeptides and lysins herein, including in the lysin sequences set out in FIG. 3 or in FIG. 4, or in active fragments or truncations thereof, such that a particular codon is changed to a codon which codes for a different amino acid, an amino acid is substituted for another amino acid, or one or more amino acids are deleted. Such a mutation is generally made by making the fewest amino acid or nucleotide changes possible. A substitution mutation of this sort can be made to change an amino acid in the resulting protein in a non-conservative manner (for example, by changing the codon from an amino acid belonging to a grouping of amino acids having a particular size or characteristic to an amino acid belonging to another grouping) or in a conservative manner (for example, by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

Thus, one of skill in the art, based on a review of the sequence of the PlySs1 and PlySs2 lysin polypeptides provided herein and on their knowledge and the public information available for other lysin polypeptides, can make amino acid changes or substitutions in the lysin polypeptide sequence. Amino acid changes can be made to replace or substitute one or more, one or a few, one or several, one to five, one to ten, or such other number of amino acids in the sequence of the lysin(s) provided herein to generate mutants or variants thereof. Such mutants or variants thereof may be predicted for function or tested for function or capability for killing bacteria, including Staphylococcal, Streptococcal, *Listeria*, or Enterococcal bacteria, and/or for having comparable activity to the lysin(s) provided herein. Thus, changes can be made to the sequence of PlySs2, for example, by modifying the amino acid sequence as set out m FIG. 4 hereof, and mutants or variants having a change in sequence can be tested using the assays and methods described and exemplified herein, including in the examples. One of skill in the art, on the basis of the domain structure of the lysin(s) hereof can predict one or more, one or several amino acids suitable for substitution or replacement and/or one or more amino acids which are not suitable for substitution or replacement, including reasonable conservative or non-conservative substitutions.

In this regard, and with exemplary reference to PlySs2 lysin it is pointed out that, although the PlySs2 polypeptide lysin represents a divergent class of prophage lytic enzyme, the lysin comprises an N-terminal CHAP domain (cysteine-histidine amidohydrolase/peptidase) and a C-terminal SH3-type 5 domain as depicted in FIG. 4. The domains are depicted in the amino acid sequence in distinct shaded color regions, with the CHAP domain corresponding to the first shaded amino acid sequence region starting with LNN . . . and the SH3-type 5 domain corresponding to the second shaded region starting with RSY . . . CHAP domains are included in several previously characterized streptococcal and staphylococcal phage lysins. Thus, one of skill in the art can reasonably make and test substitutions or replacements to the CHAP domain and/or the SH-3 domain of PlySs2. Sequence comparisons to the Genbank database can be made with either or both of the CHAP and/or SH-3 domain sequences or with the PlySs2 lysin full amino acid sequence, for instance, to identify amino acids for substitution. In FIG. 30, the CHAP domain of PlySs2 is aligned with that of the well-characterized streptococcal PlyC lysin, demonstrating conserved catalytic residues, but only a modest level of identity overall (28% sequence identity). In FIG. 30 the conserved cysteine and histidine amino acid sequences in the CHAP domain are shown with an arrow. It is reasonable to predict, for example, that the conserved cysteine and histidine residues should be maintained in a mutant or variant of PlySs2 so as to maintain activity or capability. It is notable that a mutant or variant having an alanine replaced for valine at valine amino acid 19 in the PlySs2 sequence of FIG. 4 and SEQ ID NO: 3 is active and capable of killing gram positive bacteria in a manner similar to and as effective as the FIG. 4 and SEQ ID NO:3 lysin.

The following is one example of various groupings of amino acids:

Amino Acids with Nonpolar R Groups
Alanine, Valine, Leucine, Isoleucine, Proline, Phenylalanine, Tryptophan, Methionine
Amino Acids with Uncharged Polar R Groups
Glycine, Serine, Threonine, Cysteine, Tyrosine, Asparagine, Glutamine
Amino Acids with Charged Polar R Groups (Negatively Charged at pH 6.0)
Aspartic acid, Glutamic acid
Basic Amino Acids (Positively Charged at pH 6.0)
Lysine, Arginine, Histidine (at pH 6.0)

Another grouping may be those amino acids with phenyl groups:
Phenylalanine, Tryptophan, Tyrosine Another grouping may be according to molecular weight (i.e., size of R groups):

| Glycine | 75 | Alanine | 89 |
| Serine | 105 | Proline | 115 |
| Valine | 117 | Threonine | 119 |
| Cysteine | 121 | Leucine | 131 |
| Isoleucine | 131 | Asparagine | 132 |
| Aspartic acid | 133 | Glutamine | 146 |
| Lysine | 146 | Glutamic acid | 147 |

| | | | |
|---|---|---|---|
| Methionine | 149 | Histidine (at pH 6.0) | 155 |
| Phenylalanine | 165 | Arginine | 174 |
| Tyrosine | 181 | Tryptophan | 204 |

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Exemplary and preferred conservative amino acid substitutions include any of: glutamine (Q) for glutamic acid (E) and vice versa; leucine (L) for valine (V) and vice versa; serine (S) for threonine (T) and vice versa; isoleucine (I) for valine (V) and vice versa; lysine (K) for glutamine (Q) and vice versa; isoleucine (I) for methionine (M) and vice versa; serine (S) for asparagine (N) and vice versa; leucine (L) for methionine (M) and vice versa; lysine (L) for glutamic acid (E) and vice versa; alanine (A) for serine (S) and vice versa; tyrosine (Y) for phenylalanine (F) and vice versa; glutamic acid (E) for aspartic acid (D) and vice versa; leucine (L) for isoleucine (I) and vice versa; lysine (K) for arginine (R) and vice versa.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

A polypeptide or epitope as described herein may be used to generate an antibody and also can be used to detect binding to the lysin or to molecules that recognize the lysin protein. Another embodiment is a molecule such as an antibody or other specific binder that may be created through use of an epitope such as by regular immunization or by a phase display approach where an epitope can be used to screen a library if potential binders. Such molecules recognize one or more epitopes of lysin protein or a nucleic acid that encodes lysin protein. An antibody that recognizes an epitope may be a monoclonal antibody, a humanized antibody, or a portion of an antibody protein. Desirably the molecule that recognizes an epitope has a specific binding for that epitope which is at least 10 times as strong as the molecule has for serum albumin. Specific binding can be measured as affinity (Km). More desirably the specific binding is at least $10^2$, $10^3$, $10^4$, $10^5$, $10^6$, $10^7$, $10^8$, or even higher than that for serum albumin under the same conditions.

In a desirable embodiment the antibody or antibody fragment is in a form useful for detecting the presence of the lysin protein or, alternatively detecting the presence of a bacteria susceptible to the lysin protein. In a further embodiment the antibody may be attached or otherwise associated with the lysin polypeptide of the invention, for example in a chimeric or fusion protein, and may serve to direct the lysin to a bacterial cell or strain of interest or target. Alternatively, the lysin polypeptide may serve to direct the antibody or act in conjunction with the antibody, for example in lysing the bacterial cell wall fully or partially, so that the antibody may specifically bind to its epitope at the surface or under the surface on or in the bacteria. For example, a lysin of the invention may be attached to an anti-Streptococcal antibody and direct the antibody to its epitope.

A variety of forms and methods for antibody synthesis are known as will be appreciated by a skilled artisan. The antibody may be conjugated (covalently complexed) with a reporter molecule or atom such as a fluor, an enzyme that creates an optical signal, a chemilumiphore, a microparticle, or a radioactive atom. The antibody or antibody fragment may be synthesized in vivo, after immunization of an animal, for example, the antibody or antibody fragment may be synthesized via cell culture after genetic recombination. The antibody or antibody fragment may be prepared by a combination of cell synthesis and chemical modification.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567. The term "antibody" describes an immunoglobulin whether natural or partly or wholly synthetically produced. The term also covers any polypeptide or protein having a binding domain which is, or is homologous to, an antibody binding domain. CDR grafted antibodies are also contemplated by this term. An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567. The term "antibody (ies)" includes a wild type immunoglobulin (Ig) molecule, generally comprising four full length polypeptide chains, two heavy (H) chains and two light (L) chains, or an equivalent Ig homologue thereof (e.g., a camelid nanobody, which comprises only a heavy chain); including full length functional mutants, variants, or derivatives thereof, which retain the essential epitope binding features of an Ig molecule, and including dual specific, bispecific, multispecific, and dual variable domain antibodies; Immunoglobulin molecules can be of any class (e.g., IgG, IgE, IgM, IgD, IgA, and IgY), or subclass (e.g., IgG1, IgG2, IgG3, IgG4, IgA1, and IgA2). Also included within the meaning of the term "antibody" are any "antibody fragment".

An "antibody fragment" means a molecule comprising at least one polypeptide chain that is not full length, including (i) a Fab fragment, which is a monovalent fragment consisting of the variable light (VL), variable heavy (VH), constant light (CL) and constant heavy 1 (CH1) domains; (ii) a F(ab')2 fragment, which is a bivalent fragment comprising two Fab fragments linked by a disulfide bridge at the hinge region; (iii) a heavy chain portion of an Fab (Fd) fragment, which consists of the VH and CH1 domains; (iv) a variable fragment (Fv) fragment, which consists of the VL and VH domains of a single arm of an antibody, (v) a domain antibody (dAb) fragment, which comprises a single variable domain (Ward, E. S. et al., Nature 341, 544-546 (1989)); (vi) a camelid antibody; (vii) an isolated complementarity determining region (CDR); (viii) a Single Chain Fv Fragment wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (ix) a diabody, which is a bivalent, bispecific antibody in which VH and VL domains are expressed on a single polypeptide chain, but using a linker that is too short to allow for pairing between the two domains on the same chain, thereby forcing the domains to pair with the complementarity domains of another chain and creating two antigen binding sites (WO94/13804; P. Holliger et al Proc. Natl. Acad. Sci. USA 90 6444-6448, (1993)); and (x) a linear antibody, which comprises a pair of tandem Fv segments (VH-CH1-VH-CH1) which, together with complementarity light chain polypeptides, form a pair of antigen binding regions; (xi) multivalent antibody fragments (scFv dimers, trimers and/or tetramers (Power and Hudson, J Immunol. Methods 242: 193-204 9 (2000)); and (xii) other non-full length portions of heavy and/or light chains, or mutants, variants, or derivatives thereof, alone or in any combination.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin-binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023 and U.S. Pat. Nos. 4,816,397 and 4,816,567.

An "antibody combining site" is that structural portion of an antibody molecule comprised of light chain or heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule. Exemplary antibody molecules are intact immunoglobulin molecules, substantially intact immunoglobulin molecules and those portions of an immunoglobulin molecule that contains the paratope, including those portions known in the art as Fab, Fab', $F(ab')_2$ and F(v), which portions are preferred for use in the therapeutic methods described herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The term "specific" may be used to refer to the situation in which one member of a specific binding pair will not show significant binding to molecules other than its specific binding partner(s). The term is also applicable where e.g. an antigen binding domain is specific for a particular epitope which is carried by a number of antigens, m which case the specific binding member carrying the antigen binding domain will be able to bind to the various antigens carrying the epitope.

The term "comprise" generally used in the sense of include, that is to say permitting the presence of one or more features or components.

The term "consisting essentially of" refers to a product, particularly a peptide sequence, of a defined number of residues which is not covalently attached to a larger product. In the case of the peptide of the invention hereof, those of skill in the art will appreciate that minor modifications to the N- or C-terminal of the peptide may however be contemplated, such as the chemical modification of the terminal to add a protecting group or the like, e.g. the amidation of the C-terminus.

The term "isolated" refers to the state in which the lysin polypeptide(s) of the invention, or nucleic acid encoding such polypeptides will be, in accordance with the present invention. Polypeptides and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Polypeptides and nucleic acid may be formulated with diluents or adjuvants and still for practical purposes be isolated—for example the polypeptides will normally be mixed with polymers or mucoadhesives or other carriers, or will be mixed with pharmaceutically acceptable carriers or diluents, when used in diagnosis or therapy.

Nucleic Acids

Nucleic acids capable of encoding the *S. suis* lysin polypeptide(s) of the invention are provided herein and constitute an aspect of the invention. Representative nucleic acid sequences in this context are polynucleotide sequences coding for the polypeptide of any of FIGS. 3 and 4, the polypeptides of SEQ ID NO:1, SEQ ID NO:2 and SEQ ID NO:3, and sequences that hybridize, under stringent conditions, with complementary sequences of the DNA of the FIG. 3 or 4 sequence(s). Further variants of these sequences and sequences of nucleic acids that hybridize with those shown in the figures also are contemplated for use in production of lysing enzymes according to the disclosure, including natural variants that may be obtained. A large variety of isolated nucleic acid sequences or cDNA sequences that encode phage associated lysing enzymes and partial sequences that hybridize with such gene sequences are useful for recombinant production of the lysin enzyme(s) or polypeptide(s) of the invention.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Many of the herein contemplated variant DNA molecules include those created by standard DNA mutagenesis techniques, such as M13 primer mutagenesis. Details of these techniques are provided in Sambrook et al. (1989) In Molecular Cloning: A Laboratory Manual, Cold Spring Harbor, N.Y. (incorporated herein by reference). By the use of such techniques, variants may be created which differ in minor ways from those disclosed. DNA molecules and nucleotide sequences which are derivatives of those specifically disclosed herein and which differ from those disclosed by the deletion, addition or substitution of nucleotides while still encoding a protein which possesses the functional characteristic of the lysin polypeptide(s) are contemplated by the disclosure. Also included are small DNA molecules which are derived from the disclosed DNA molecules. Such small DNA molecules include oligonucleotides suitable for use as hybridization probes or polymerase chain reaction (PCR) primers. As such, these small DNA molecules will comprise at least a segment of a lytic enzyme genetically coded for by a bacteriophage of *Staphylococcus suis* and, for the purposes of PCR, will comprise at least a 10-15 nucleotide sequence and, more preferably, a 15-30 nucleotide sequence of the gene. DNA molecules and nucleotide sequences which are derived from the disclosed DNA molecules as described above may also be defined as DNA sequences which hybridize under stringent conditions to the DNA sequences disclosed, or fragments thereof.

Hybridization conditions corresponding to particular degrees of stringency vary depending upon the nature of the hybridization method of choice and the composition and length of the hybridizing DNA used. Generally, the temperature of hybridization and the ionic strength (especially the sodium ion concentration) of the hybridization buffer will determine the stringency of hybridization. Calculations regarding hybridization conditions required for attaining particular degrees of stringency are discussed by Sambrook et al. (1989), In Molecular Cloning: A Laboratory Manual, Cold Spring Harbor, N.Y., chapters 9 and 11 (herein incorporated by reference).

An example of such calculation is as follows. A hybridization experiment may be performed by hybridization of a DNA molecule (for example, a natural variation of the lytic enzyme genetically coded for by a bacteriophage specific for *Bacillus anthracis*) to a target DNA molecule. A target DNA may be, for example, the corresponding cDNA which has been electrophoresed m an agarose gel and transferred to a nitrocellulose membrane by Southern blotting (Southern (1975). J. Mol. Biol. 98:503), a technique well known in the art and described in Sambrook et al. (1989) In Molecular Cloning: A Laboratory Manual, Cold Spring Harbor, N.Y. (incorporated herein by reference). Hybridization with a target probe labeled with isotopic $P^{32}$ labeled-dCTP is carried out in a solution of high ionic strength such as 6 times SSC at a temperature that is 20-25 degrees Celsius below the melting temperature, Tm (described infra). For such Southern hybridization experiments where the target DNA molecule on the Southern blot contains 10 ng of DNA or more, hybridization is carried out for 6-8 hours using 1-2 ng/ml radiolabeled probe (of specific activity equal to 109 CPM/mug or greater). Following hybridization, the nitrocellulose filter is washed to remove background hybridization. The washing conditions are as stringent as possible to remove background hybridization while retaining a specific hybridization signal. The term "Tm" represents the temperature above which, under the prevailing ionic conditions, the radiolabeled probe molecule will not hybridize to its target DNA molecule. The Tm of such a hybrid molecule may be estimated from the following equation: $T_m$=81.5° C.−16.6 (log 10 of sodium ion concentration)+0.41(% G+C)−0.63(% formamide)−(600/1) where 1=the length of the hybrid in base pairs. This equation is valid for concentrations of sodium ion in the range of 0.01M to 0.4M, and it is less accurate for calculations of Tm in solutions of higher sodium ion concentration (Bolton and McCarthy (1962). Proc. Natl. Acad. Sci. USA 48:1390) (incorporated herein by reference). The equation also is valid for DNA having G+C contents within 30% to 75%, and also applies to hybrids greater than 100 nucleotides in length. The behavior of oligonucleotide probes is described in detail m Ch. 11 of Sambrook et al. (1989), In Molecular Cloning: A Laboratory Manual, Cold Spring Harbor, N.Y. (incorporated herein by reference). The preferred exemplified conditions described here are particularly contemplated for use in selecting variations of the lytic gene.

In preferred embodiments of the present disclosure, stringent conditions may be defined as those under which DNA molecules with more than 25% sequence variation (also termed "mismatch") will not hybridize. In a more preferred embodiment, stringent conditions are those under which DNA molecules with more than 15% mismatch will not hybridize, and more preferably still, stringent conditions are those under which DNA sequences with more than 10% mismatch will not hybridize. Preferably, stringent conditions are those under which DNA sequences with more than 6% mismatch will not hybridize.

The degeneracy of the genetic code further widens the scope of the embodiments as it enables major variations in the nucleotide sequence of a DNA molecule while maintaining the amino acid sequence of the encoded protein. For example, a representative amino acid residue is alanine. This may be encoded in the cDNA by the nucleotide codon triplet GCT. Because of the degeneracy of the genetic code, three other nucleotide codon triplets—GCT, GCC and GCA—also code for alanine. Thus, the nucleotide sequence of the gene could be changed at this position to any of these three codons without affecting the amino acid composition of the encoded protein or the characteristics of the protein. The genetic code and variations in nucleotide codons for particular amino acids are well known to the skilled artisan. Based upon the degeneracy of the genetic code, variant DNA molecules may be derived from the cDNA molecules disclosed herein using standard DNA mutagenesis techniques as described above, or by synthesis of DNA sequences. DNA sequences which do not hybridize under stringent conditions to the cDNA sequences disclosed by virtue of sequence variation based on the degeneracy of the genetic code are herein comprehended by this disclosure.

Thus, it should be appreciated that also within the scope of the present invention are DNA sequences encoding a lysin of the present invention, including PlySs2 and PlySs1, which sequences code for a polypeptide having the same amino acid sequence as provided in FIG. 3 or 4 or in SEQ ID NO:1, 2 or 3, but which are degenerate thereto or are degenerate to the exemplary nucleic acids sequences provided in FIG. 3 or 4. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC or GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |

| | |
|---|---|
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

One skilled in the art will recognize that the DNA mutagenesis techniques described here and known in the art can produce a wide variety of DNA molecules that code for a bacteriophage lysin in *Streptococcus suis* yet that maintain the essential characteristics of the lytic polypeptides described and provided herein. Newly derived proteins may also be selected in order to obtain variations on the characteristic of the lytic polypeptide(s), as will be more fully described below. Such derivatives include those with variations in amino acid sequence including minor deletions, additions and substitutions.

While the site for introducing an amino acid sequence variation may be predetermined, the mutation per se does not need to be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence as described above are well known.

Amino acid substitutions are typically of single residues, or can be of one or more, one or a few, one, two, three, four, five, six or seven residues; insertions usually will be on the order of about from 1 to 10 amino acid residues; and deletions will range about from 1 to 30 residues. Deletions or insertions may be in single form, but preferably are made in adjacent pairs, i.e., a deletion of 2 residues or insertion of 2 residues. Substitutions, deletions, insertions or any combination thereof may be combined to arrive at a final construct. Obviously, the mutations that are made in the DNA encoding the protein must not place the sequence out of reading frame and preferably will not create complementary regions that could produce secondary mRNA structure (EP 75,444A).

Substitutional variants are those in which at least one residue in the amino acid sequence has been removed and a different residue inserted in its place. Such substitutions may be made so as to generate no significant effect on the protein characteristics or when it is desired to finely modulate the characteristics of the protein. Amino acids which may be substituted for an original amino acid in a protein and which are regarded as conservative substitutions are described above and will be recognized by one of skill in the art.

Substantial changes m function or immunological identity may be made by selecting substitutions that are less conservative, for example by selecting residues that differ more significantly in their effect on maintaining: (a) the structure of the polypeptide backbone in the area of the substitution, for example, as a sheet or helical conformation; (b) the charge or hydrophobicity of the molecule at the target site; or (c) the bulk of the side chain. The substitutions which in general are expected to produce the greatest changes in protein properties will be those in which: (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The effects of these amino acid substitutions or deletions or additions may be assessed for derivatives or variants of the lytic polypeptide(s) by analyzing the ability of the derivative or variant proteins to lyse or kill susceptible bacteria, or to complement the sensitivity to DNA cross-linking agents exhibited by phages m infected bacteria hosts. These assays may be performed by transfecting DNA molecules encoding the derivative or variant proteins into the bacteria as described above or by incubating bacteria with expressed proteins from hosts transfected with the DNA molecules encoding the derivative or variant proteins.

While the site for introducing an amino acid sequence variation can be predetermined, the mutation per se does not need to be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence as described above are well known.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host. Such operative linking of a DNA sequence of this invention to an expression control sequence, of course, includes, if not already part of the DNA sequence, the provision of an initiation codon, ATG, in the correct reading frame upstream of the DNA sequence. A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids colE1, pCR1, pBR322, pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2□ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli, Pseudomonas, Bacillus, Streptomyces*, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention.

Libraries of fragments of the coding sequence of a polypeptide can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein (Arkin and Yourvan (1992) Proc. Natl. Acad. Sci. USA 89:7811-7815; Delgrave et al. (1993) Protein Engineering 6(3):327-331).

Compositions

Therapeutic or pharmaceutical compositions comprising the lytic enzyme(s)/polypeptide(s) of the invention are provided in accordance with the invention, as well as related methods of use and methods of manufacture. Therapeutic or pharmaceutical compositions may comprise one or more lytic polypeptide(s), and optionally include natural, truncated, chimeric or shuffled lytic enzymes, optionally combined with other components such as a carrier, vehicle, polypeptide, polynucleotide, holin protein(s), one or more antibiotics or suitable excipients, carriers or vehicles. The invention provides therapeutic compositions or pharmaceutical compositions of the lysins of the invention, including PlySs2 and/or PlySs1 (particularly ΔPlySs1), for use in the killing, alleviation, decolonization, prophylaxis or treatment of gram-positive bacteria, including bacterial infections or related conditions. The invention provides therapeutic compositions or pharmaceutical compositions of the lysins of the invention, including PlySs2 and/or PlySs1 (particularly ΔPlySs1), for use in treating, reducing or controlling contamination and/or infections by gram positive bacteria, particularly including *Streptococcus suis*, including m contamination or infection of or via an external surface such as skin. Compositions are thereby contemplated and provided for topical or dermatological applications and general administration to the exterior, including the skin or other external surface. Compositions comprising PlySs2 or PlySs1 lysin, including truncations or variants thereof, are provided herein for use in the killing, alleviation, decolonization, prophylaxis or treatment of gram-positive bacteria, including bacterial infections or related conditions, particularly of *Streptococcus, Staphylococcus, Enterococcus* or *Listeria*, including *Streptococcus pyogenes* and antibiotic resistant *Staphylococcus aureus*.

The enzyme(s) or polypeptide(s) included in the therapeutic compositions may be one or more or any combination of unaltered phage associated lytic enzyme(s), truncated lytic polypeptides, variant lytic polypeptide(s), and chimeric and/or shuffled lytic enzymes. Additionally, different lytic polypeptide(s) genetically coded for by different phage for treatment of the same bacteria may be used. These lytic enzymes may also be any combination of "unaltered" lytic enzymes or polypeptides, truncated lytic polypeptide(s), variant lytic polypeptide(s), and chimeric and shuffled lytic enzymes. The lytic enzyme(s)/polypeptide(s) in a therapeutic or pharmaceutical composition for gram-positive bacteria, including *Streptococcus, Staphylococcus, Enterococcus* and *Listeria*, may be used alone or in combination with antibiotics or, if there are other invasive bacterial organisms to be treated, in combination with other phage associated lytic enzymes specific for other bacteria being targeted. The lytic enzyme, truncated enzyme, variant enzyme, chimeric enzyme, and/or shuffled lytic enzyme may be used in conjunction with a holin protein. The amount of the holin protein may also be varied. Various antibiotics may be optionally included in the therapeutic composition with the enzyme(s) or polypeptide(s) and with or without the presence of lysostaphin. More than one lytic enzyme or polypeptide may be included in the therapeutic composition.

The pharmaceutical composition can also include one or more altered lytic enzymes, including isozymes, analogs, or variants thereof, produced by chemical synthesis or DNA recombinant techniques. In particular, altered lytic protein can be produced by amino acid substitution, deletion, truncation, chimerization, shuffling, or combinations thereof. The pharmaceutical composition may contain a combination of one or more natural lytic protein and one or more truncated, variant, chimeric or shuffled lytic protein. The pharmaceutical composition may also contain a peptide or a peptide fragment of at least one lytic protein derived from the same or different bacteria species, with an optional addition of one or more complementary agent, and a pharmaceutically acceptable carrier or diluent.

The present invention provides to bacterial lysins comprising a PlySs lysin polypeptide variant having bacterial killing activity. The invention describes PlySs lysin truncation mutants that contain only one catalytic or enzymatic domain and retains gram positive antibacterial activity. The invention describes, for example, exemplary PlySs lysin truncation mutant that contain only one domain selected from the predicted alanine-amidase domain and the predicted glucosaminidase domain. In the PLySS1 truncation mutant, for example, the C terminal glucosaminidase domain is deleted, so that the truncated lysin comprises and contains an N-terminal enzymatic domain and a cell-wall binding domain. The ΔPlySS1 truncation has the N-terminal 254 amino acids, whereas the full length PlySs1 lysin has 452 amino acids. Thus, the invention provides S suis lysin mutants, particularly PlySs1 lysin mutants which are truncated mutants containing only one catalytic domain and which retain killing activity against S. suis and numerous other bacterial strains including other Streptococcus, as well as Staphylococcus, Listeria, and other bacteria, as provided and demonstrated herein. A composition is herein provided comprising a PlySs mutant lysin, including a PlySS1 mutant lysin, having equal or greater killing activity against Streptococcus cells, including Streptococcus suis compared with the full length PlySs lysin protein, including the full length PlySs1 lysin protein, the PlySs mutant lysin having a polypeptide variant of the amino acid sequence of SEQ ID NO:1 with a modification selected from the group consisting of: a) the PlySs mutant is a truncated mutant lysin containing only one catalytic domain selected from the group consisting of an endopeptidase domain and a glucosaminidase domain; b) the PlySs mutant is a truncated mutant lysin without a C-terminal enzymatic domain; c) the PlySs mutant has a single catalytic domain and a cell-wall binding domain; and d) the PlySs mutant corresponds to SEQ ID NO:2, or amino acid variants thereof having one or more conservative substitutions.

The therapeutic composition may also comprise a holin protein. Holin proteins (or "holins") are proteins which produce holes in the cell membrane. Holin proteins may form lethal membrane lesions that terminate cellular respiration in a bacteria. Like the lytic proteins, holin proteins are coded for and carried by a phage. In fact, it is quite common for the genetic code of the holin protein to be next to or even within the code for the phage lytic protein. Most holin protein sequences are short, and overall, hydrophobic in nature, with a highly hydrophilic carboxy-terminal domain. In many cases, the putative holin protein is encoded on a different reading frame within the enzymatically active domain of the phage. In other cases, holin protein is encoded on the DNA next or close to the DNA coding for the cell wall lytic protein. Holin proteins are frequently synthesized during the late stage of phage infection and found in the cytoplasmic membrane where they cause membrane lesions. Holins can be grouped into two general classes based on primary structure analysis. Class I holins are usually 95 residues or longer and may have three potential transmembrane domains. Class II holins are usually smaller, at approximately 65-95 residues, with the distribution of charged and hydrophobic residues indicating two TM domains (Young, et al. Trends in Microbiology v. 8, No. 4, March 2000). At least for the phages of gram-positive hosts, however, the dual-component lysis system may not be universal. Although the presence of holins has been shown or suggested for several phages, no genes have yet been found encoding putative holins for all phages. Holins have been shown to be present in several bacteria, including, for example, lactococcal bacteriophage Tuc2009, lactococcal NLC3, pneumococcal bacteriophage EJ-1, Lactobacillus gasseri bacteriophage Nadh, Staphylococcus aureus bacteriophage Twort, Listeria monocytogenes bacteriophages, pneumococcal phage Cp-1, Bacillus subtilis phage M29, Lactobacillus delbrueckki bacteriophage LL-H lysin, and bacteriophage N 11 of Staphyloccous aureus. (Loessner, et al., Journal of Bacteriology, August 1999, p. 4452-4460).

For example, holin proteins can be used in conjunction with the lytic enzymes to accelerate the speed and efficiency at which the bacteria are killed. Holin proteins may also be in the form of chimeric and/or shuffled enzymes. Holin proteins may also be used alone in the treatment of bacterial infections according to some embodiments.

The pharmaceutical composition can contain a complementary agent, including one or more antimicrobial agent and/or one or more conventional antibiotics. In order to accelerate treatment of the infection, the therapeutic agent may further include at least one complementary agent which can also potentiate the bactericidal activity of the lytic enzyme. Antimicrobials act largely by interfering with the structure or function of a bacterial cell by inhibition of cell wall synthesis, inhibition of cell-membrane function and/or inhibition of metabolic functions, including protein and DNA synthesis. Antibiotics can be subgrouped broadly into those affecting cell wall peptidoglycan biosynthesis and those affecting DNA or protein synthesis in gram positive bacteria. Cell wall synthesis inhibitors, including penicillin and antibiotics like it, disrupt the rigid outer cell wall so that the relatively unsupported cell swells and eventually ruptures. Antibiotics affecting cell wall peptidoglycan biosynthesis include: Glycopeptides, which inhibit peptidoglycan synthesis by preventing the incorporation of N-acetylmuramic acid (NAM) and N-acetylglucosamine (NAG) peptide subunits into the peptidoglycan matrix. Available glycopeptides include vancomycin and teicoplanin. Penicillins, which act by inhibiting the formation of peptidoglycan cross-links. The functional group of penicillins, the β-lactam moiety, binds and inhibits DD-transpeptidase that links the peptidoglycan molecules in bacteria. Hydrolytic enzymes continue to break down the cell wall, causing cytolysis or death due to osmotic pressure. Common penicillins include oxacillin, ampicillin and cloxacillin; and Polypeptides, which interfere with the dephosphorylation of the $C_{55}$-isoprenyl pyrophosphate, a molecule that carries peptidoglycan building-blocks outside of the plasma membrane. A cell wall-impacting polypeptide is bacitracin.

The complementary agent may be an antibiotic, such as erythromycin, clarithromycin, azithromycin, roxithromycin, other members of the macrolide family, penicilins, cephalosporins, and any combinations thereof in amounts which are effective to synergistically enhance the therapeutic effect of the lytic enzyme. Virtually any other antibiotic may be used with the altered and/or unaltered lytic enzyme. Similarly, other lytic enzymes may be included in the carrier to treat other bacterial infections. Antibiotic supplements may be used in virtually all uses of the enzyme when treating different diseases. The pharmaceutical composition can also contain a peptide or a peptide fragment of at least one lytic protein, one holin protein, or at least one holin and one lytic protein, which lytic and holin proteins are each derived from the same or different bacteria species, with an optional addition of a complementary agents, and a suitable carrier or diluent.

Also provided are compositions containing nucleic acid molecules that, either alone or in combination with other nucleic acid molecules, are capable of expressing an effective amount of a lytic polypeptide(s) or a peptide fragment of a lytic polypeptide(s) in vivo. Cell cultures containing these nucleic acid molecules, polynucleotides, and vectors carrying and expressing these molecules in vitro or in vivo, are also provided.

Therapeutic or pharmaceutical compositions may comprise lytic polypeptide(s) combined with a variety of carriers to treat the illnesses caused by the susceptible gram-positive bacteria. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter-ions such as sodium; non-ionic surfactants such as polysorbates, poloxamers, or polyethylene glycol (PEG); and/or neutral salts, e.g., NaCl, KCl, $MgCl_2$, $CaCl_2$, and others. Glycerin or glycerol (1,2,3-propanetriol) is commercially available for pharmaceutical use. It may be diluted in sterile water for injection, or sodium chloride injection, or other pharmaceutically acceptable aqueous injection fluid, and used m concentrations of 0.1 to 100% (v/v), preferably 1.0 to 50% more preferably about 20%. DMSO is an aprotic solvent with a remarkable ability to enhance penetration of many locally applied drugs. DMSO may be diluted in sterile water for injection, or sodium chloride injection, or other pharmaceutically acceptable aqueous injection fluid, and used in concentrations of 0.1 to 100% (v/v). The carrier vehicle may also include Ringer's solution, a buffered solution, and dextrose solution, particularly when an intravenous solution is prepared.

Any of the carriers for the lytic polypeptide(s) may be manufactured by conventional means. However, it is preferred that any mouthwash or similar type products not contain alcohol to prevent denaturing of the polypeptide/enzyme. Similarly, when the lytic polypeptide(s) is being placed in a cough drop, gum, candy or lozenge during the manufacturing process, such placement should be made prior to the hardening of the lozenge or candy but after the cough drop or candy has cooled somewhat, to avoid heat denaturation of the enzyme.

A lytic polypeptide(s) may be added to these substances in a liquid form or in a lyophilized state, whereupon it will be solubilized when it meets body fluids such as saliva. The polypeptide(s)/enzyme may also be in a micelle or liposome.

The effective dosage rates or amounts of an altered or unaltered lytic enzyme/polypeptide(s) to treat the infection will depend in part on whether the lytic enzyme/polypeptide(s) will be used therapeutically or prophylactically, the duration of exposure of the recipient to the infectious bacteria, the size and weight of the individual, etc. The duration for use of the composition containing the enzyme/polypeptide(s) also depends on whether the use is for prophylactic purposes, wherein the use may be hourly, daily or weekly, for a short time period, or whether the use will be for therapeutic purposes wherein a more intensive regimen of the use of the composition may be needed, such that usage may last for hours, days or weeks, and/or on a daily basis, or at timed intervals during the day. Any dosage form employed should provide for a minimum number of units for a minimum amount of time. The concentration of the active units of enzyme believed to provide for an effective amount or dosage of enzyme may be in the range of about 100 units/ml to about 500,000 units/ml of fluid in the wet or damp environment of the nasal and oral passages, and possibly in the range of about 100 units/ml to about 50,000 units/ml. More specifically, time exposure to the active enzyme/polypeptide(s) units may influence the desired concentration of active enzyme units per ml. Carriers that are classified as "long" or "slow" release carriers (such as, for example, certain nasal sprays or lozenges) could possess or provide a lower concentration of active (enzyme) units per ml, but over a longer period of time, whereas a "short" or "fast" release carrier (such as, for example, a gargle) could possess or provide a high concentration of active (enzyme) units per ml, but over a shorter period of time. The amount of active units per ml and the duration of time of exposure depend on the nature of infection, whether treatment is to be prophylactic or therapeutic, and other variables. There are situations where it may be necessary to have a much higher unit/ml dosage or a lower unit/ml dosage.

The lytic enzyme/polypeptide(s) should be in an environment having a pH which allows for activity of the lytic enzyme/polypeptide(s). For example if a human individual has been exposed to another human with a bacterial upper respiratory disorder, the lytic enzyme/polypeptide(s) will reside in the mucosal lining and prevent any colonization of the infecting bacteria. Prior to, or at the time the altered lytic enzyme is put in the carrier system or oral delivery mode, it is preferred that the enzyme be in a stabilizing buffer environment for maintaining a pH range between about 4.0 and about 9.0, more preferably between about 5.5 and about 7.5.

A stabilizing buffer may allow for the optimum activity of the lysin enzyme/polypeptide(s). The buffer may contain a reducing reagent, such as dithiothreitol. The stabilizing buffer may also be or include a metal chelating reagent, such as ethylenediaminetetracetic acid disodium salt, or it may also contain a phosphate or citrate-phosphate buffer, or any other buffer. The DNA coding of these phages and other phages may be altered to allow a recombinant enzyme to attack one cell wall at more than two locations, to allow the recombinant enzyme to cleave the cell wall of more than one species of bacteria, to allow the recombinant enzyme to attack other bacteria, or any combinations thereof. The type and number of alterations to a recombinant bacteriophage produced enzyme are incalculable.

A mild surfactant can be included in a therapeutic or pharmaceutical composition in an amount effective to potentiate the therapeutic effect of the lytic enzyme/polypeptide(s) may be used in a composition. Suitable mild surfactants include, inter alia, esters of polyoxyethylene sorbitan and fatty acids (Tween series), octylphenoxy polyethoxy ethanol (Triton-X series), n-Octyl-.beta.-D-glucopyranoside, n-Octyl-.beta.-D-thioglucopyranoside, n-Decyl-.beta.-D-glucopyranoside, n-Dodecyl-.beta.-D-glucopyranoside, and biologically occurring surfactants, e.g., fatty acids, glycerides, monoglycerides, deoxycholate and esters of deoxycholate.

Preservatives may also be used in this invention and preferably comprise about 0.05% to 0.5% by weight of the total composition. The use of preservatives assures that if the product is microbially contaminated, the formulation will prevent or diminish microorganism growth. Some preservatives useful in this invention include methylparaben, propylparaben, butylparaben, chloroxylenol, sodium benzoate, DMDM Hydantoin, 3-Iodo-2-Propylbutyl carbamate, potassium sorbate, chlorhexidine digluconate, or a combination thereof.

Pharmaceuticals for use in all embodiments of the invention include antimicrobial agents, anti-inflammatory agents, antiviral agents, local anesthetic agents, corticosteroids, destructive therapy agents, antifungals, and antiandrogens. In the treatment of acne, active pharmaceuticals that may be used include antimicrobial agents, especially those having anti-inflammatory properties such as dapsone, erythromycin, minocycline, tetracycline, clindamycin, and other antimicrobials. The preferred weight percentages for the antimicrobials are 0.5% to 10%.

Local anesthetics include tetracaine, tetracaine hydrochloride, lidocaine, lidocaine hydrochloride, dyclonine, dyclonine hydrochloride, dimethisoquin hydrochloride, dibucaine, dibucaine hydrochloride, butambenpicrate, and pramoxine hydrochloride. A preferred concentration for local anesthetics is about 0.025% to 5% by weight of the total composition. Anesthetics such as benzocaine may also be used at a preferred concentration of about 2% to 25% by weight.

Corticosteroids that may be used include betamethasone dipropionate, fluocinolone actinide, betamethasone valerate, triamcinolone actinide, clobetasol propionate, desoximetasone, diflorasone diacetate, amcinonide, flurandrenolide, hydrocortisone valerate, hydrocortisone butyrate, and desonide are recommended at concentrations of about 0.01% to 1.0% by weight. Preferred concentrations for corticosteroids such as hydrocortisone or methylprednisolone acetate are from about 0.2% to about 5.0% by weight.

Additionally, the therapeutic composition may further comprise other enzymes, such as the enzyme lysostaphin for the treatment of any *Staphylococcus aureus* bacteria present along with the susceptible gram-positive bacteria. Mucolytic peptides, such as lysostaphin, have been suggested to be efficacious in the treatment of *S. aureus* infections of humans (Schaffner et al., Yale J. Biol. & Med., 39:230 (1967). Lysostaphin, a gene product of *Staphylococcus simulans*, exerts a bacteriostatic and bactericidal effect upon *S. aureus* by enzymatically degrading the polyglycine crosslinks of the cell wall (Browder et al., Res. Comm., 19: 393-400 (1965)). U.S. Pat. No. 3,278,378 describes fermentation methods for producing lysostaphin from culture media of *S. staphylolyticus*, later renamed *S. simulans*. Other methods for producing lysostaphin are further described in U.S. Pat. Nos. 3,398,056 and 3,594,284. The gene for lysostaphin has subsequently been cloned and sequenced (Recsei et al., Proc. Natl. Acad. Sci. USA, 84: 1127-1131 (1987)). The recombinant mucolytic bactericidal protein, such as r-lysostaphin, can potentially circumvent problems associated with current antibiotic therapy because of its targeted specificity, low toxicity and possible reduction of biologically active residues. Furthermore, lysostaphin is also active against non-dividing cells, while most antibiotics require actively dividing cells to mediate their effects (Dixon et al., Yale J. Biology and Medicine, 41: 62-68 (1968)). Lysostaphin, in combination with the altered lytic enzyme, can be used in the presence or absence of antibiotics. There is a degree of added importance in using both lysostaphin and the lysin enzyme in the same therapeutic agent. Frequently, when a human has a bacterial infection, the infection by one genus of bacteria weakens the human body or changes the bacterial flora of the body, allowing other potentially pathogenic bacteria to infect the body. One of the bacteria that sometimes co-infects a body is *Staphylococcus aureus*. Many strains of *Staphylococcus aureus* produce penicillinase, such that *Staphylococcus, Streptococcus*, and other Gram positive bacterial strains will not be killed by standard antibiotics. Consequently, the use of the lysin and lysostaphin, possibly m combination with antibiotics, can serve as the most rapid and effective treatment of bacterial infections. A therapeutic composition may also include mutanolysin, and lysozyme.

Means of application of the therapeutic composition comprising a lytic enzyme/polypeptide(s) include, but are not limited to direct, indirect, carrier and special means or any combination of means. Direct application of the lytic enzyme/polypeptide(s) may be by any suitable means to directly bring the polypeptide in contact with the site of infection or bacterial colonization, such as to the nasal area (for example nasal sprays), dermal or skin applications (for example topical ointments or formulations), suppositories, tampon applications, etc. Nasal applications include for instance nasal sprays, nasal drops, nasal ointments, nasal washes, nasal injections, nasal packings, bronchial sprays and inhalers, or indirectly through use of throat lozenges, mouthwashes or gargles, or through the use of ointments applied to the nasal nares, or the face or any combination of these and similar methods of application. The forms in which the lytic enzyme may be administered include but are not limited to lozenges, troches, candies, injectants, chewing gums, tablets, powders, sprays, liquids, ointments, and aerosols.

When the natural and/or altered lytic enzyme(s)/polypeptide(s) is introduced directly by use of sprays, drops, ointments, washes, injections, packing and inhalers, the enzyme is preferably in a liquid or gel environment, with the liquid acting as the carrier. A dry anhydrous version of the altered enzyme may be administered by the inhaler and bronchial spray, although a liquid form of delivery is preferred.

Compositions for treating topical infections or contaminations comprise an effective amount of at least one lytic enzyme, including PlySs1 and/or PlySs2, according to the invention and a carrier for delivering at least one lytic enzyme to the infected or contaminated skin, coat, or external surface of a companion animal or livestock. The mode of application for the lytic enzyme includes a number of different types and combinations of carriers which include, but are not limited to an aqueous liquid, an alcohol base liquid, a water soluble gel, a lotion, an ointment, a nonaqueous liquid base, a mineral oil base, a blend of mineral oil and petrolatum, lanolin, liposomes, protein carriers such as serum albumin or gelatin, powdered cellulose carmel, and combinations thereof. A mode of delivery of the carrier containing the therapeutic agent includes, but is not limited to a smear, spray, a time-release patch, a liquid absorbed wipe, and combinations thereof. The lytic enzyme may be applied to a bandage either directly or in one of the other carriers. The bandages may be sold damp or dry, wherein the enzyme is in a lyophilized form on the bandage. This method of application is most effective for the treatment of infected skin. The carriers of topical compositions may comprise semi-solid and gel-like vehicles that include a polymer thickener, water, preservatives, active surfactants or emulsifiers, sun screens, antioxidants, and a solvent or mixed solvent system. U.S. Pat. No. 5,863,560 (Osborne) discusses a number of different carrier combinations which can aid in the exposure of the skin to a medicament. Polymer thickeners that may be used include those known to one skilled in the art, such as hydrophilic and hydroalcoholic gelling agents frequently used in the cosmetic and pharmaceutical industries. CARBOPOL® is one of numerous cross-linked acrylic acid polymers that are given the general adopted name carbomer. These polymers dissolve in water and form a clear or slightly hazy gel upon neutralization with a caustic material such as sodium hydroxide, potassium hydroxide, triethanolamine, or other amine bases. KLUCEL® is a cellulose polymer that is dispersed in water and forms a uniform gel upon complete hydration. Other preferred gelling polymers include hydroxyethylcellulose, cellulose gum, MVE/MA decadiene crosspolymer, PVM/MA copolymer, or a combination thereof.

A composition comprising a lytic enzyme/polypeptide(s) can be administered in the form of a candy, chewing gum, lozenge, troche, tablet, a powder, an aerosol, a liquid, a liquid spray, or toothpaste for the prevention or treatment of bacterial infections associated with upper respiratory tract illnesses. The lozenge, tablet, or gum into which the lytic enzyme/polypeptide(s) is added may contain sugar, corn syrup, a variety of dyes, non-sugar sweeteners, flavorings, any binders, or combinations thereof. Similarly, any gum-based products may contain acacia, carnauba wax, citric acid, cornstarch, food colorings, flavorings, non-sugar sweeteners, gelatin, glucose, glycerin, gum base, shellac, sodium saccharin, sugar, water, white wax, cellulose, other binders, and combinations thereof. Lozenges may further contain sucrose, cornstarch, acacia, gum tragacanth, anethole, linseed, oleoresin, mineral oil, and cellulose, other binders, and combinations thereof. Sugar substitutes can also be used in place of dextrose, sucrose, or other sugars.

Compositions comprising lytic enzymes, or their peptide fragments can be directed to the mucosal lining, where, in residence, they kill colonizing disease bacteria. The mucosal lining, as disclosed and described herein, includes, for example, the upper and lower respiratory tract, eye, buccal cavity, nose, rectum, vagina, periodontal pocket, intestines and colon. Due to natural eliminating or cleansing mechanisms of mucosal tissues, conventional dosage forms are not retained at the application site for any significant length of time.

It may be advantageous to have materials which exhibit adhesion to mucosal tissues, to be administered with one or more phage enzymes and other complementary agents over a period of time. Materials having controlled release capability are particularly desirable, and the use of sustained release mucoadhesives has received a significant degree of attention. J. R. Robinson (U.S. Pat. No. 4,615,697, incorporated herein by reference) provides a good review of the various controlled release polymeric compositions used in mucosal drug delivery. The patent describes a controlled release treatment composition which includes a bioadhesive and an effective amount of a treating agent. The bioadhesive is a water swellable, but water insoluble fibrous, crosslinked, carboxy functional polymer containing (a) a plurality of repeating units of which at least about 80 percent contain at least one carboxyl functionality, and (b) about 0.05 to about 1.5 percent crosslinking agent substantially free from polyalkenyl polyether. While the polymers of Robinson are water swellable but insoluble, they are crosslinked, not thermoplastic, and are not as easy to formulate with active agents, and into the various dosage forms, as the copolymer systems of the present application. Micelles and multilamillar micelles may also be used to control the release of enzyme.

Other approaches involving mucoadhesives which are the combination of hydrophilic and hydrophobic materials, are known. Orahesive® from E.R. Squibb & Co is an adhesive which is a combination of pectin, gelatin, and sodium carboxymethyl cellulose in a tacky hydrocarbon polymer, for adhering to the oral mucosa. However, such physical mixtures of hydrophilic and hydrophobic components eventually fall apart. In contrast, the hydrophilic and hydrophobic domains in this application produce an insoluble copolymer. U.S. Pat. No. 4,948,580, also incorporated by reference, describes a bioadhesive oral drug delivery system. The composition includes a freeze-dried polymer mixture formed of the copolymer poly(methyl vinyl ether/maleic anhydride) and gelatin, dispersed in an ointment base, such as mineral oil containing dispersed polyethylene. U.S. Pat. No. 5,413,792 (incorporated herein by reference) discloses paste-like preparations comprising (A) a paste-like base comprising a polyorganosiloxane and a water soluble polymeric material which are preferably present in a ratio by weight from 3:6 to 6:3, and (B) an active ingredient. U.S. Pat. No. 5,554,380 claims a solid or semisolid bioadherent orally ingestible drug delivery system containing a water-in-oil system having at least two phases. One phase comprises from about 25% to about 75% by volume of an internal hydrophilic phase and the other phase comprises from about 23% to about 75% by volume of an external hydrophobic phase, wherein the external hydrophobic phase is comprised of three components: (a) an emulsifier, (b) a glyceride ester, and (c) a wax material. U.S. Pat. No. 5,942,243 describes some representative release materials useful for administering antibacterial agents, which are incorporated by reference.

Therapeutic or pharmaceutical compositions can also contain polymeric mucoadhesives including a graft copolymer comprising a hydrophilic main chain and hydrophobic graft chains for controlled release of biologically active agents. The graft copolymer is a reaction product of (1) a polystyrene macromonomer having an ethylenically unsaturated functional group, and (2) at least one hydrophilic acidic monomer having an ethylenically unsaturated functional group. The graft chains consist essentially of polystyrene, and the main polymer chain of hydrophilic monomeric moieties, some of which have acidic functionality. The weight percent of the polystyrene macromonomer in the graft copolymer is between about 1 and about 20% and the weight percent of the total hydrophilic monomer in the graft copolymer is between 80 and 99%, and wherein at least 10% of said total hydrophilic monomer is acidic, said graft copolymer when fully hydrated having an equilibrium water content of at least 90%. Compositions containing the copolymers gradually hydrate by sorption of tissue fluids at the application site to yield a very soft jelly like mass exhibiting adhesion to the mucosal surface. During the period of time the composition is adhering to the mucosal surface, it provides sustained release of the pharmacologically active agent, which is absorbed by the mucosal tissue.

The compositions of this application may optionally contain other polymeric materials, such as poly(acrylic acid), poly,-(vinyl pyrrolidone), and sodium carboxymethyl cellulose plasticizers, and other pharmaceutically acceptable excipients in amounts that do not cause deleterious effect upon mucoadhesivity of the composition.

The dosage forms of the compositions of this invention can be prepared by conventional methods. In cases where intramuscular injection is the chosen mode of administration, an isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. A vasoconstriction agent can be added to the formulation. The pharmaceutical preparations according to this application are provided sterile and pyrogen free.

A lytic enzyme/polypeptide(s) of the invention may also be administered by any pharmaceutically applicable or acceptable means including topically, orally or parenterally. For example, the lytic enzyme/polypeptide(s) can be administered intramuscularly, intrathecally, subdermally, subcutaneously, or intravenously to treat infections by gram-positive bacteria. In cases where parenteral injection is the chosen mode of administration, an isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. A vasoconstriction agent can be added to the formulation. The pharmaceutical preparations according to this application are provided sterile and pyrogen free.

For any compound, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. The exact dosage is chosen by the individual physician in view of the patient to be treated. Dosage and administration are adjusted to provide sufficient levels of the active moiety or to maintain the desired effect. Additional factors which may be taken into account include the severity of the disease state, age, weight and gender of the patient; diet, desired duration of treatment, method of administration, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

The effective dosage rates or amounts of the lytic enzyme/polypeptide(s) to be administered parenterally, and the duration of treatment will depend in part on the seriousness of the infection, the weight of the patient, particularly human, the duration of exposure of the recipient to the infectious bacteria, the number of square centimeters of skin or tissue which are infected, the depth of the infection, the seriousness of the infection, and a variety of a number of other variables. The composition may be applied anywhere from once to several times a day, and may be applied for a short or long term period. The usage may last for days or weeks. Any dosage form employed should provide for a minimum number of units for a minimum amount of time. The concentration of the active units of enzymes believed to provide for an effective amount or dosage of enzymes may be selected as appropriate. The amount of active units per ml and the duration of time of exposure depend on the nature of infection, and the amount of contact the carrier allows the lytic enzyme(s)/polypeptide(s) to have.

Methods and Assays

The bacterial killing capability, and indeed the significantly broad range of bacterial killing, exhibited by the lysin polypeptide(s) of the invention provides for various methods based on the antibacterial effectiveness of the polypeptide(s) of the invention. Thus, the present invention contemplates antibacterial methods, including methods for killing of gram-positive bacteria, for reducing a population of gram-positive bacteria, for treating or alleviating a bacterial infection, for treating a human subject exposed to a pathogenic bacteria, and for treating a human subject at risk for such exposure. The susceptible bacteria are demonstrated herein to include the bacteria from which the phage enzyme(s) of the invention are originally derived, *Streptococcus suis*, as well as various other Streptococcal, Staphylococcal, Enterococcal and *Listeria* bacterial strains. Methods of treating various conditions are also provided, including methods of prophylactic treatment of Streptococcal, Staphylococcal, Enterococcal or *Listeria* infections, treatment of Streptococcal, Staphylococcal, Enterococcal or *Listeria* infections, reducing Streptococcal, Staphylococcal, Enterococcal or *Listeria* population or carriage, treating lower respiratory infection, treating ear infection, treating ottis media, treating endocarditis, and treating or preventing other local or systemic infections or conditions.

The lysin(s) of the present invention demonstrate remarkable capability to kill and effectiveness against bacteria from various species such as multiple Streptococcal or Staphylococcal species, bacteria across distinct species groups such as bacteria from each of Streptococcal, Staphylococcal, Enterococcal and/or *Listeria*, and bacterial from distinct orders. The bacterial taxonomic class of Bacilli includes two orders, Bacillales and Lactobacillales. The Bacillales order includes *Staphylococcus, Listeria* and also *Bacillus*. The Lactobacillales order includes *Streptococcus, Enterococcus, Lactobacillus* and *Lactococcus*. The lysin(s) of the present invention demonstrate anti-bacterial activity and the capability to kill bacteria from distinct orders of bacteria, particularly from distinct orders of Bacilli bacteria. The lysin(s) provided herein are capable of killing bacteria from order Bacillales and also from order Lactobacillales. The PlySs2 lysin is demonstrated herein to kill bacteria from two distinct orders, particularly Bacillales and Lactobacillales, in vitro and in vivo. Lysin of the present invention is capable of killing Bacillales and Lactobacillales bacteria in mixed culture and in mixed infections in vivo. The invention thus contemplates treatment, decolonization, and/or decontamination of bacteria, cultures or infections or in instances wherein more than one gram positive bacteria is suspected or present. In particular, the invention contemplates treatment, decolonization, and/or decontamination of bacteria, cultures or infections or in instances wherein more than one type of Bacilalles bacteria, more than one type of Lactobacillales bacteria, or at least one type of Bacillales and one type of Lactobacillales bacteria is suspected, present, or may be present.

This invention may also be used to treat septicemia, particularly in a human. For the treatment of a septicemic infection, such as for *pneumoniae*, or bacterial meningitis, there should be a continuous intravenous flow of therapeutic agent into the blood stream. The concentration of the enzymes for the treatment of septicemia is dependent upon the bacterial count in the blood and the blood volume.

Also provided is a method for treating Streptococcal, Staphylococcal, Enterococcal or *Listeria* infection, carriage or populations comprises treating the infection with a therapeutic agent comprising an effective amount of at least one lytic enzyme(s)/polypeptide(s) of the invention, particularly PlySs2 and/or PlySs1, particularly PlySs2. More specifically, lytic enzyme/polypeptide capable of lysing the cell wall of Streptococcal, Staphylococcal, Enterococcal or *Listeria* bacterial strains is produced from genetic material from a bacteriophage specific for *Streptococcus suis*. In the methods of the invention, the lysin polypeptide(s) of the present invention, including PlySs2 and/or PlySs1, particularly PlySs2, are useful and capable in prophylactic and treatment methods directed against gram-positive bacteria, particularly Streptococcal, Staphylococcal, Enterococcal or *Listeria* infections or bacterial colonization. Bacterial strains susceptible and relevant as targets in the methods of the invention include and may be selected from *Staphylococcus aureus, Listeria monocytogenes, Staphylococcus simulans, Streptococcus suis, Staphylococcus epidermidis, Streptococcus equi, Streptococcus equi zoo, Streptococcus agalactiae* (GBS), *Streptococcus pyogenes* (GAS), *Streptococcus sanguinis, Streptococcus gordonii, Streptococcus dysgalactiae*, Group G *Streptococcus*, Group E *Streptococcus, Enterococcus faecalis* and *Streptococcus pneumonia*.

The invention includes methods of treating or alleviating Streptococcal, including *S. pyogenes*, and/or Staphylococcal, including *S. aureus*, related infections or conditions, including antibiotic-resistant *Staphylococcus aureus*, particularly including MRSA, wherein the bacteria or a human subject infected by or exposed to the particular bacteria, or suspected of being exposed or at risk, is contacted with or administered an amount of isolated lysin polypeptide(s) of the invention effective to kill the particular bacteria. Thus, one or more of PlySs2 and/or PlySs1, including truncations or variants thereof, including such polypeptides as provided herein in FIGS. 3 and 4 and in SEQ ID NOS: 1, 2 or 3, is contacted or administered so as to be effective to kill the relevant bacteria or otherwise alleviate or treat the bacterial infection.

The term 'agent' means any molecule, including polypeptides, antibodies, polynucleotides, chemical compounds and small molecules. In particular the term agent includes compounds such as test compounds, added additional compound(s), or lysin enzyme compounds.

The term 'agonist' refers to a ligand that stimulates the receptor the ligand binds to in the broadest sense.

The term 'assay' means any process used to measure a specific property of a compound. A 'screening assay' means a process used to characterize or select compounds based upon their activity from a collection of compounds.

The term 'preventing' or 'prevention' refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term 'prophylaxis' is related to and encompassed in the term 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Therapeutically effective amount' means that amount of a drug, compound, antimicrobial, antibody, polypeptide, or pharmaceutical agent that will elicit the biological or medical response of a subject that is being sought by a medical doctor or other clinician. In particular, with regard to gram-positive bacterial infections and growth of gram-positive bacteria, the term "effective amount" is intended to include an effective amount of a compound or agent that will bring about a biologically meaningful decrease in the amount of or extent of infection of gram-positive bacteria, including having a bacteriocidal and/or bacteriostatic effect. The phrase "therapeutically effective amount" is used herein to mean an amount sufficient to prevent, and preferably reduce by at least about 30 percent, more preferably by at least 50 percent, most preferably by at least 90 percent, a clinically significant change in the growth or amount of infectious bacteria, or other feature of pathology such as for example, elevated fever or white cell count as may attend its presence and activity.

The term 'treating' or 'treatment' of any disease or infection refers, in one embodiment, to ameliorating the disease or infection (i.e., arresting the disease or growth of the infectious agent or bacteria or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or infection, either physically, (e.g., stabilization of a discernible symptom), physiologically, (e.g., stabilization of a physical parameter), or both. In a further embodiment, 'treating' or 'treatment' relates to slowing the progression of a disease or reducing an infection.

The phrase "pharmaceutically acceptable" refers to molecular entities and compositions that are physiologically tolerable and do not typically produce an allergic or similar untoward reaction, such as gastric upset, dizziness and the like, when administered to a human.

It is noted that in the context of treatment methods which are carried out in vivo or medical and clinical treatment methods in accordance with the present application and claims, the term subject, patient or individual is intended to refer to a human.

The terms "gram-positive bacteria", "Gram-positive bacteria", "gram-positive" and any variants not specifically listed, may be used herein interchangeably, and as used throughout the present application and claims refer to Gram-positive bacteria which are known and/or can be identified by the presence of certain cell wall and/or cell membrane characteristics and/or by staining with Gram stain. Gram positive bacteria are known and can readily be identified and may be selected from but are not limited to the genera *Listeria, Staphylococcus, Streptococcus, Enterococcus, Mycobacterium, Corynebacterium*, and *Clostridium*, and include any and all recognized or unrecognized species or strains thereof. In an aspect of the invention, the PlyS lysin sensitive gram-positive bacteria include bacteria selected from one or more of *Listeria, Staphylococcus, Streptococcus*, and *Enterococcus*.

The term "bacteriocidal" refers to capable of killing bacterial cells.

The term "bacteriostatic" refers to capable of inhibiting bacterial growth, including inhibiting growing bacterial cells.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the S phase activity of a target cellular mass, or other feature of pathology such as for example, elevated blood pressure, fever or white cell count as may attend its presence and activity.

One method for treating systemic or tissue bacterial infections caused by *Streptococcus* or *Staphylococcus* bacteria comprises parenterally treating the infection with a therapeutic agent comprising an effective amount of one or more lysin polypeptide(s) of the invention, particularly PlySs2 and/or PlySs1, including truncations or variants thereof, including such polypeptides as provided herein in FIGS. 3 and 4 and in SEQ ID NOS: 1, 2 or Sand an appropriate carrier. A number of other different methods may be used to introduce the lytic enzyme(s)/polypeptide(s). These methods include introducing the lytic enzyme(s)/polypeptide(s) intravenously, intramuscularly, subcutaneously, intrathecally, and subdermally. One skilled in the art, including medical personnel, will be capable of evaluating and recognizing the most appropriate mode or means of administration, given the nature and extent of the bacterial condition and the strain or type of bacteria involved or suspected. For instance, intrathecal use and administration of one or more lytic polypeptide(s) would be most beneficial for treatment of bacterial meningitis.

Infections may be also be treated by injecting into the infected tissue of the human patient a therapeutic agent comprising the appropriate lytic enzyme(s)/polypeptide(s) and a carrier for the enzyme. The carrier may be comprised of distilled water, a saline solution, albumin, a serum, or any combinations thereof. More specifically, solutions for infusion or injection may be prepared in a conventional manner, e.g. with the addition of preservatives such as p-hydroxybenzoates or stabilizers such as alkali metal salts of ethylene-diamine tetraacetic acid, which may then be transferred into fusion vessels, injection vials or ampules. Alternatively, the compound for injection may be lyophilized either with or without the other ingredients and be solubilized in a buffered solution or distilled water, as appropriate, at the time of use. Non-aqueous vehicles such as fixed oils, liposomes, and ethyl oleate are also useful herein. Other phage associated lytic enzymes, along with a holin protein, may be included in the composition.

Various methods of treatment are provided for using a lytic enzyme/polypeptide(s), such as PlySs2 and PlySS1 as exemplified herein, as a prophylactic treatment for eliminating or reducing the carriage of susceptible bacteria, preventing those humans who have been exposed to others who have the symptoms of an infection from getting sick, or as a therapeutic treatment for those who have already become ill from the infection. Similarly, the lytic enzyme(s)/polypeptide(s) can be used to treat, for example, lower respiratory tract illnesses, particularly by the use of bronchial sprays or intravenous administration of the enzyme. For example, a lytic enzyme can be used for the prophylactic and therapeutic treatment of eye infections, such as conjunctivitis. The method of treatment comprises administering eye drops or an eye wash which comprise an effective amount of at least one lytic polypeptide(s) of the invention and a carrier capable of being safely applied to an eye, with the carrier containing the lytic enzymes. The eye drops or eye wash are preferably in the form of an isotonic solution. The pH of the solution should be adjusted so that there is no irritation of the eye, which in turn would lead to possible infection by other organisms, and possible to damage to the eye. While the pH range should be in the same range as for other lytic enzymes, the most optimal pH will be in the range as demonstrated and provided herein. Similarly, buffers of the sort described above for the other lytic enzymes should also be used. Other antibiotics which are suitable for use in eye drops may be added to the composition containing the enzymes. Bactericides and bacteriostatic compounds may also be added. The concentration of the enzyme(s) in the solution can be in the range of from about 100 units/ml to about 500,000 units/ml, with a more preferred range of about 100 to about 5,000 units/mil, and about 100 to about 50,000 units/ml. Concentrations can be higher or lower than the ranges provided.

The lytic polypeptide(s) of the invention may also be used in a contact lens solution, for the soaking and cleaning of contact lenses. This solution, which is normally an isotonic solution, may contain, in addition to the enzyme, sodium chloride, mannitol and other sugar alcohols, borates, preservatives, and the like. A lytic enzyme/polypeptide of the invention may also be administered to the ear of a patient. Thus, for instance a lytic polypeptide(s) of the invention may be used to treat ear infections, for example caused by *Streptococcus pneumoniae*. Otitis media is an inflammation of the middle ear characterized by symptoms such as otalgia, hearing loss and fever. One of the primary causes of these symptoms is a build up of fluid (effusion) in the middle ear. Complications include permanent hearing loss, perforation of the tympanic membrane, acquired cholesteatoma, mastoiditis, and adhesive otitis. Children who develop otitis media in the first years of life are at risk for recurrent acute or chronic disease. One of the primary causes of otitis media is *Streptococcus pneumoniae*. The lytic enzyme(s)/polypeptide(s) may be applied to an infected ear by delivering the enzyme(s) in an appropriate carrier to the canal of the ear. The carrier may comprise sterile aqueous or oily solutions or suspensions. The lytic enzyme(s) may be added to the carrier, which may also contain suitable preservatives, and preferably a surface-active agent. Bactericidal and fungicidal agents preferably included m the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol. Additionally, any number of other eardrop carriers may be used. The concentrations and preservatives used for the treatment of otitis media and other similar ear infections are the same as discussed for eye infections, and the carrier into which the enzyme goes is similar or identical to the carriers for treatment of eye infections. Additionally, the carrier may typically includes vitamins, minerals, carbohydrates, sugars, amino acids, proteinaceous materials, fatty acids, phospholipids, antioxidants, phenolic compounds, isotonic solutions, oil based solutions, oil based suspensions, and combinations thereof.

The diagnostic, prophylactic and therapeutic possibilities and applications that are raised by the recognition of and isolation of the lysin polypeptide(s) of the invention, derive from the fact that the polypeptides of the invention cause direct and specific effects (e.g. killing) in susceptible bacteria. Thus, the polypeptides of the invention may be used to eliminate, characterize, or identify the relevant and susceptible bacteria.

Thus, a diagnostic method of the present invention may comprise examining a cellular sample or medium for the purpose of determining whether it contains susceptible bacteria, or whether the bacteria in the sample or medium are susceptible by means of an assay including an effective amount of one or more lysin polypeptide(s) and a means for characterizing one or more cell in the sample, or for determining whether or not cell lysis has occurred or is occurring. Patients capable of benefiting from this method include those suffering from an undetermined infection, a recognized bacterial infection, or suspected of being exposed to or carrying a particular bacteria. A fluid, food, medical device, composition or other such sample which will come in contact with a subject or patient may be examined for susceptible bacteria or may be eliminated of relevant bacteria. In one such aspect a fluid, food, medical device, composition or other such sample may be sterilized or otherwise treated to eliminate or remove any potential relevant bacteria by incubation with or exposure to one or more lytic polypeptide(s) of the invention.

The procedures and their application are all familiar to those skilled in the art and accordingly may be utilized within the scope of the present invention. In one instance, the lytic polypeptide(s) of the invention complex(es) with or otherwise binds or associates with relevant or susceptible bacteria in a sample and one member of the complex is labeled with a detectable label. The fact that a complex has formed and, if desired, the amount thereof, can be determined by known methods applicable to the detection of labels. The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$ and $^{186}Re$. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLE 1

Cloning and Characterization of Phage Lysins from S. suis

*Streptococcus suis* is a Gram-positive pathogen that infects pigs worldwide. Reports of zoonotic transmission from pigs to humans are increasing (Sriskandan S. et al (2006) PLoS Medicine 3(5):585-567). *S. suis* may develop a consistent presence in human populations in years to come. Humans and pigs have been treated with penicillin or gentamicin, but *S. suis* isolates resistant to these antibiotics exist (Cantin, M. et al (1992) J Vet Diagnostic Investig 4:170-174).

We purified and characterized two phage lysins from strains of *S. suis* (PlySs1 and PlySs2) and confirmed their in vitro activity against various *S. suis* strains. In addition, the *S. suis* lysin, particularly PlySs2 lysin, was shown in vitro to kill various other and distinct strains of *Streptococcus*, including Group B strep. The PlySs2 lysin also is effective in killing numerous other bacteria, including other pathogenic and clinically significant bacteria, particularly *Staphylococcus*, including *Staphylococcus aureus*, even antibiotic resistant *S. aureus* such as MRSA, *Enterococcus*, including *Enterococcus faecalis*, and *Listeria*.

Results

PlySs1 was isolated and cloned via a functional genomic screen using *S. suis* prophage genomic DNA and PlySs2 was identified by sequence analysis of the *S. suis* prophage genome sequence and then isolated and cloned. The PlySs1 lysin was cloned through functional shotgun screening of the genome of *S. suis* 7711, a serotype 7 strain. Microgram quantities of genomic DNA (gDNA) were briefly subjected to restriction digestion with Tsp509I (NEB). Fragments 1.5-4 kb in length were isolated via agarose-gel electrophoresis and ligated into EcoRI-linearized pBAD24 plasmid. This plasmid confers ampicillin resistance and allows for arabinose induction of the recombinant insert. To identify lysin-encoding clones, libraries were subject to a novel screening technique that relies upon the toxicity of adjacently-encoded holin proteins (Schmitz J. E. et al (2010) Adv Environ Microbiol 76(21):7181-7187). Briefly, *E. coli* TOP10 transformants were plated onto LB-agar supplemented with ampicillin and sheep's blood. Following proliferation to macroscopic colonies, the plates were exposed to a mist of arabinose to induce recombinant transcription. Toxic clones were revealed by the development of a surrounding zone of hemolysis. These colonies were identified, re-propagated and subject to a secondary screen in which they were overlaid with heat-killed bacteria (to assay directly for the production of lytic enzyme). For the *S. suis* strain (7711) that yielded the PlySs1 lysin, ~3,500 clones were subjected to the original hemolysis screen; 100 of these were selected for the secondary screen, 2 of which encoded the lytic enzyme. For the theoretical translated protein, putative enzymatic and binding domains assignments were made via Pfam analysis (pfam.sanger.ac.uk). Based on this information, primers were designed for synthesizing a truncated constructed (hereafter referred to as PlySs1) with an inserted stop codon preceding the C-terminal glucosaminidase domain. The nucleic acid and amino acid sequences of the full length PlySs1 lysin and the amino acid sequence of a truncated enzyme are provided in FIG. 3.

For the identification and cloning of PlySs2, the genomes of 8 sequenced isolates of *S. suis* were inspected for the presence of lysin-encoding genes within integrated prophage. These strains were: 05ZYH33 (NCBI Genome Project #17153); 98HAH33 (#17155); BM407 (#32237); GZ1 (#18737); P1/7 (#352); SC84 (#32239); 05HAS68 05HAH33 (#17157); and 89/1591 (#12417). For each genome, the topologically-arranged list of annotated ORFs was manually inspected for potential prophage regions. If a prophage was suspected, the theoretical translations of each ORF in that region were subject to, and putative lysin-status was assigned based on the combination of predicted enzymatic and binding domains. The only lysin gene identified in this manner (PlySs2 from strain 89/1591) was PCR-cloned from genomic DNA and cloned in to the pBad24 *E. coli* expression plasmid (see below). The nucleotide and amino acid sequence of PlySs2 lysin are provided in FIG. 4.

As described above, two *S. suis* lysins have been identified and cloned through a combination of functional recombinant screening and computational analysis of published *S.*

Figure 1:
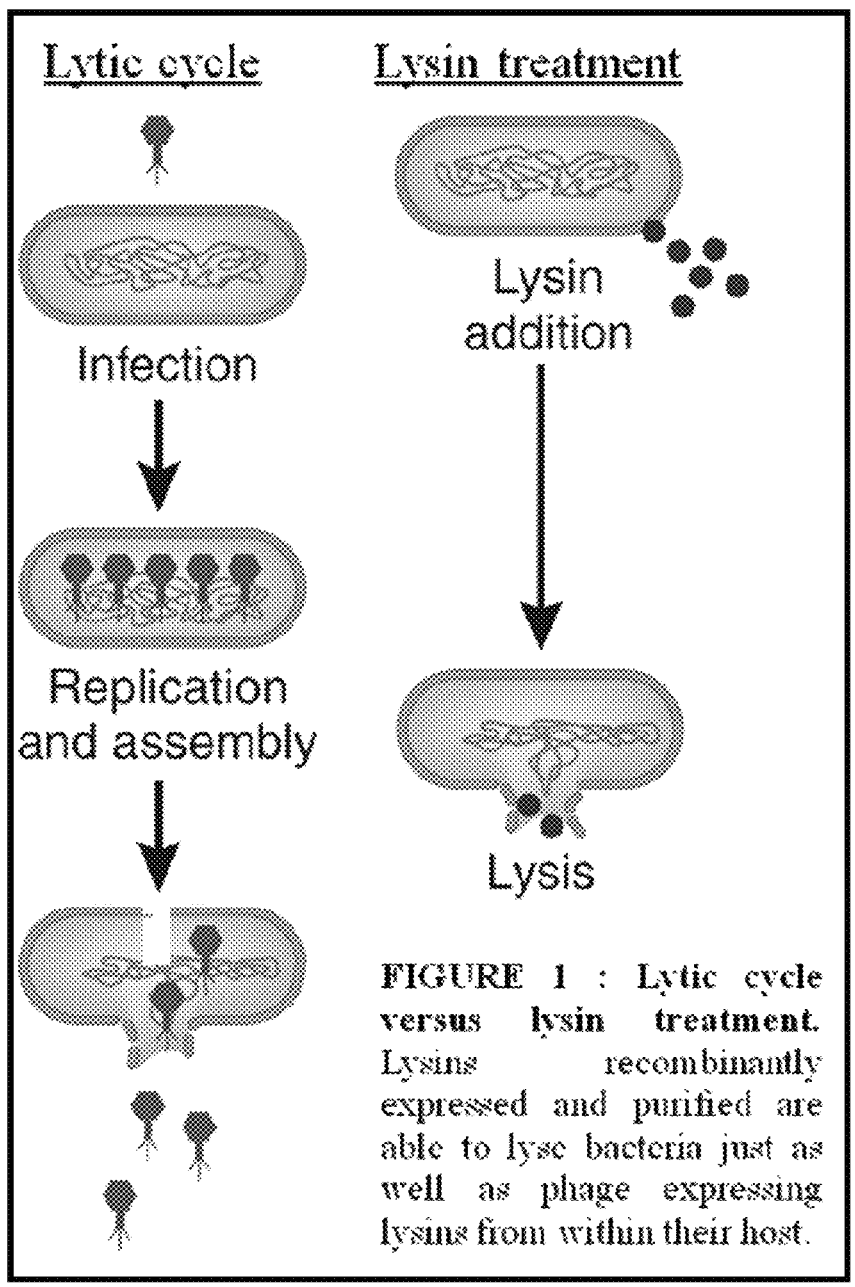
FIG. 1 depicts the lytic cycle versus lysin treatment. Lysins recombinantly expressed and purified are able to lyse bacteria just as well as phage expressing lysins from within their host.
Figure 2:
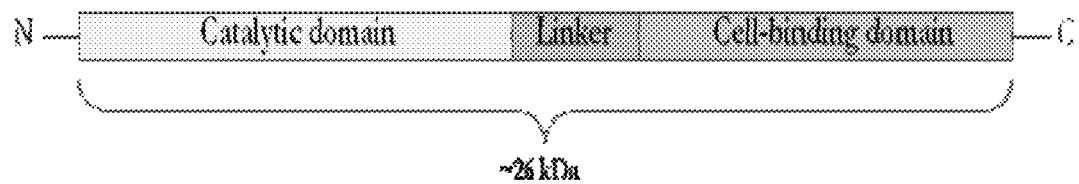
FIG. 2 depicts the PlySs2 domains. The catalytic domain corresponds to residues 8-146. There is a 16-residue linker. The binding domain corresponds to residues 162-228.

*suis* genomes. These lysins have been cloned and named PlySs1 and PlySs2. Like other lysins, the *S. suis* lysins, particularly PlySs2, have an N-terminal catalytic domain and C-terminal cell-binding domain (SH-3 Type 5 binding domain in PlySs2) (FIG. 2). In fact, the natural structure of PlySs1 as cloned from *S. suis* strain 7711 contained an additional secondary catalytic domain downstream of the binding domain (an atypical lysin arrangement), however this domain was recombinantly eliminated (as described above) to conform to standard architecture.

Figure 5:
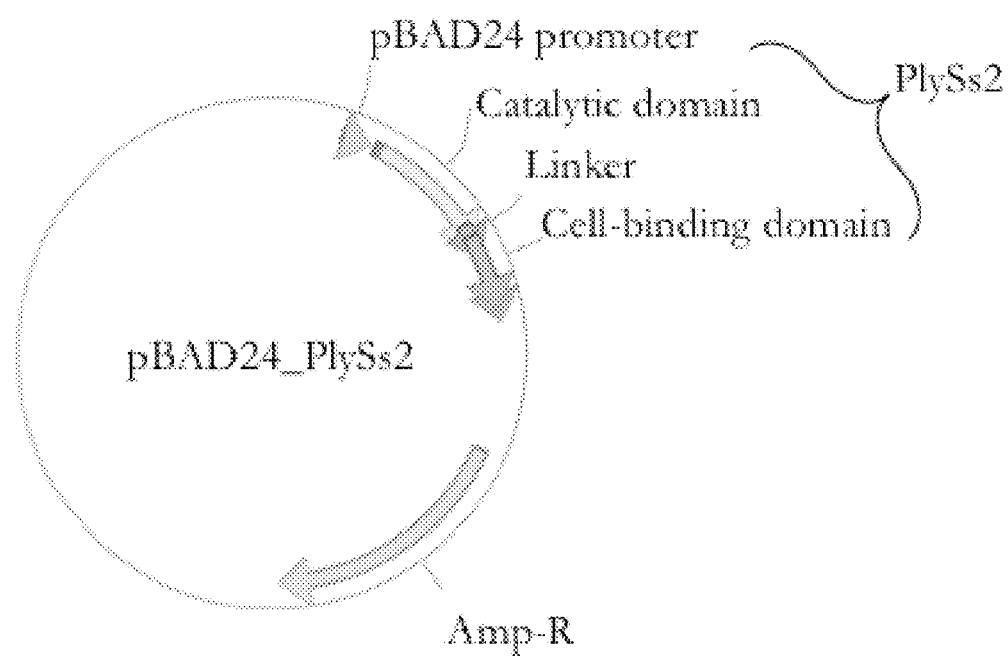
FIG. 5 depicts the pBAD24 vector. The sequence begins with the pBAD arabinose-inducible promoter for the T7 polymerase and ends with PlySs2. Ampicillin serves as a selective marker to ensure retention of the plasmid as cells grow.

The lysin-encoding gene PlySs2 was found within an integrated prophage genome along the sequenced genome of *S. suis* serotype 2 strain 89/1591 (NCBI Genome Project #12417, GenBank accession ZP_03625529) (Lucas, S. et al, US DOE Joint Genome Institute, direct submission). PlySs2 was PCR-cloned from genomic DNA from strain 89/1591 with the following primers: AATGCTAGCCTGATACACA-GTTAGAGACC-fwd (SEQ ID NO:9) and CCTAAGCT-TCTTTTCACAAATCATAATCCCCAG-rev (SEQ ID NO:10). The primers include restriction sites (NheI and HindIII) for cloning into pBAD24. The forward primer corresponds to a position≈60 bp upstream of the gene starting point, because several in-frame ATG triplets are situated near one another at the 5'-end. This enables the native ribosomal binding site (instead of the engineered RBS of pBAD24) to guide transcription. PlySs2 was cloned out of a prophage genome in *S. suis* into a pBAD24 vector (pBAD24_PlySs2, FIG. 5) and transformed it into *Escherichia coli* Top 10 cells. pBAD24 encodes β-lactamase, enables tight transcriptional control, and is induced by inexpensive arabinose. The vector-transformed *E. coli* were grown on opaque plate containing *Pseudomonas* peptidoglycan halos suspended in soft agar (Wang, Y et al (2009) Curr Microbiol 58(6):609-615). Clearing zones appeared around the *E. coli* colonies indicating expression of active PlySs2, which hydrolyzed the peptidoglycan within the soft agar. The structure of PlySs2 is quite unlike that of LySMP. It encodes a predicted N-terminal CHAP domain (cysteine-histidine amidohydrolase/peptidase, PF05257) and a C-terminal SH3-type 5 domain (PF08460) (FIG. 4). N-terminal sequencing confirmed the start as "MTTVNEA . . . ".

Lysin Protein Production

*E. coli* containing the pBAD24_PlySs2 plasmid were grown at 37° C. in 10 L of LB AMP100 and induced for overnight expression with 0.2% arabinose at an $OD_{600}$~0.8. The cultures were spun at 10,722 rcf for 20 mins. The pellets were resuspended in 100 mL of 15 mM $Na_3PO_4$, pH 7.4 and mixed with protease inhibitor cocktail tablets. This mixture was homogenized, and the homogenate was centrifuged at 1,723 rcf for 20 mins. The supernatant was ultra-centrifuged at 30,000 rpm for 1 hr. Enough 15 mM $Na_3PO_4$, pH 8.0 was added to the supernatant to bring the pH to 7.4.

The protein was run over an anionic HiTrap Fast Flow DEAE column (15 mM $Na_3PO_4$ (PB), pH 7.4) without PlySs2 binding (FIG. 6A). Ammonium sulphate was added to the flow through to a 40% concentration. The precipitate was centrifuged and resuspended in 200 mL 15 mM $Na_3PO_4$, pH 6.7. The protein was dialyzed overnight in 15 mM $Na_3PO_4$, pH 6.7 with 20 µm tubing. The dialysate was run over a cationic HiTrap Fast Flow CM column with PlySs2 eluting cleanly in the shoulder of the flow through as well as at 70 mM NaCl, 15 mM $Na_3PO_4$, pH 6.7 (FIG. 6B). All fractions showing pure PlySs2 were pooled (FIG. 6C). It is notable that there are three start codons in frame proceeding PlySs2: "ATGATGCGTGGAAAGGAGAAGCCT ATGACAACAGTAAATGAAGCATTA . . . " (corresponding to: "MMRGKEKPMT TVNEAL . . . "). A pure sample of the protein was submitted for protein sequencing to confirm c the start to be "MTTVNEAL . . . ".

To express PlySs1, the clone was grown in Power Broth+ LB-Booster (Athena Enzyme System) to $OD_{600}$≈1.0 and induced with 0.2% arabinose. The culture was shaken for 4 hr at 37° C. (inclusion bodies would form at longer times). The expressing cells were pelleted, resuspended m 15 mM phosphate buffer pH 6.2, and lysed by three passages through an EmulsiFlex C-5 homogenizer. Residual debris was removed by centrifugation (1 hr, 35,000×G), and ammonium sulfate was added at 225 g/L (40% saturation). The precipitated protein was pelleted and resolubilized in 15 mM phosphate pH 7.4, and dialyzed against this buffer overnight. The dialysate was next passed through a DEAE anion-exchange column equilibrated against the same buffer (fast flow resin, General Electric).

Figure 6:
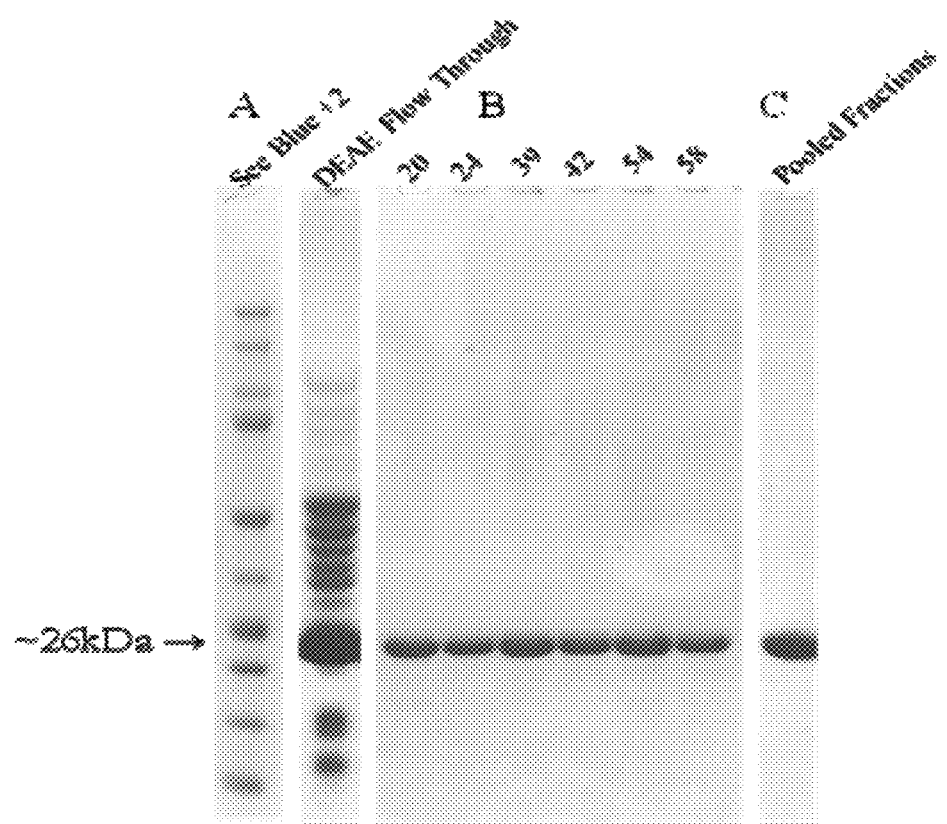
FIG. 6 shows PlySs2 purification. All samples were run on 4-12% Bis-Tris gels at 200 V for ~40 mins and stained with Coomassie. A. The DEAE column flow through containing PlySs2 at ~26 kDa. B. Six representative fractions of PlySs2 purified from a 10 L prep. C. A single band at ~26 kDa indicating the purity of PlySs2 after all fractions were pooled together.

The aforementioned preparation led to a highly pure lysin preparation in just two chromatographic steps (FIG. 6). With a predicted pI of 9.01, PlySs2 flowed directly through the DEAE column at pH=7.4 leaving the bulk of the contaminant proteins stuck to the DEAE column. PlySs2 eluted cleanly in the shoulder of the flow through and at 17 mM NaCl, being purified from proteins that rapidly flowed through the CM resin. This preparation yielded≈60 mg of protein per liter of *E. coli* culture at ≈1.5 mg/ml with >99% purity. The yield increased to ≈150 mg per liter of *E. coli* culture at ≈2.0 mg/ml with >90% purity when the CM column step was forwent. If necessary, the latter product was: dialyzed (into 5 mM PB, 15 mM NaCl); lyophilized; reconstituted (at 10% of the original volume); centrifuged; and filter-sterilized (to remove any insoluble material). This generated a soluble solution of PlySs2 at 20 mg/ml, which retained the concentration-adjusted activity of the lower concentration starting material. PlySs2 can be produced more efficiently, and at a higher concentration, than many published lysins (Daniel A et al (2010) Antimicrob Agents Chemother 54(4):1602-1612; Wang, Y. et al (2009) Curr Microbiol 58(6):609-615; Nelson, D et al (2006) Proc Natl Acad Sci USA 103(28):10765-10770).

Biochemical Characterization of PlySs2

Figure 7A:
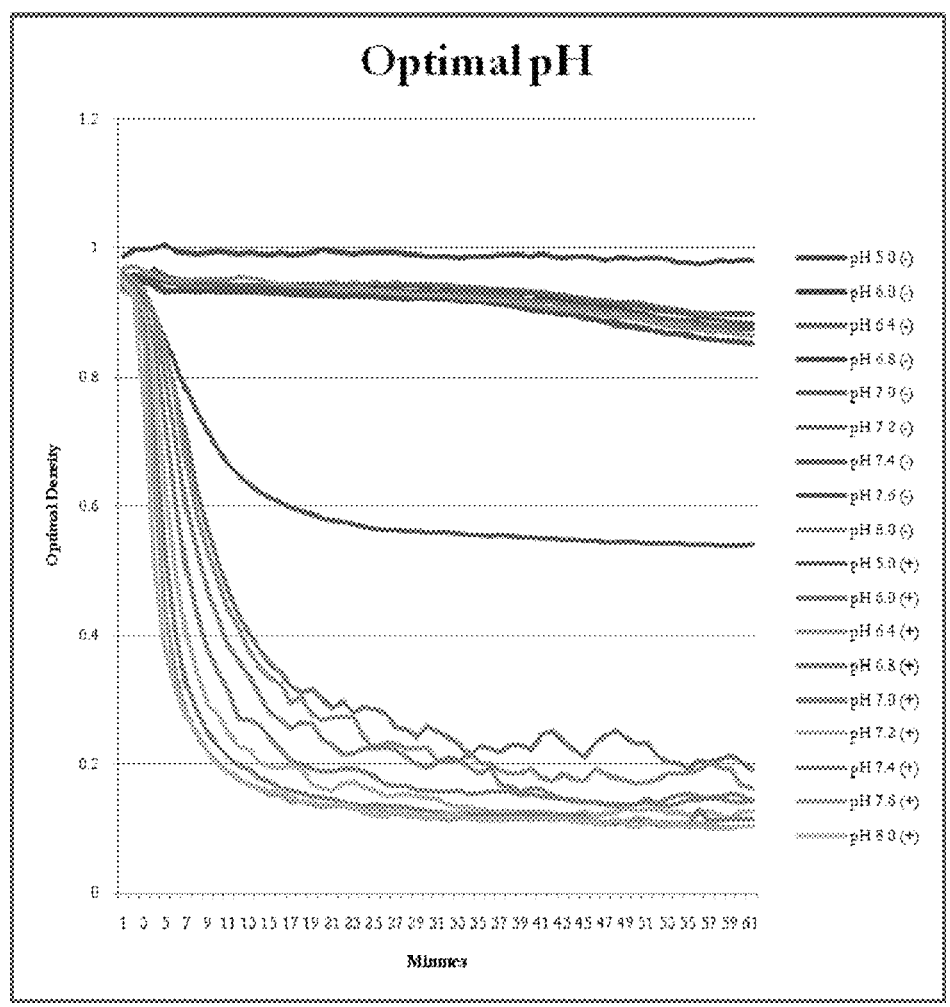
FIG. 7 depicts various aspects of PlySs2 characterization. A. To test the optimal pH for PlySs2 activity, 50 µL of various phosphate/citrate buffers pH levels were mixed with 195 µL S. suis strain 7997 cells and 5 µL of lysin. PlySs2 had the strongest activity at pH 8.0. PlySs2 was shown to have acute activity up to pH 9.7. B. 195 µL of cells, 5 µL lysin were added to 50 µL of various NaCl concentrations to determine the optimal salt concentration for PlySs2. C. To determine the temperature stability of PlySs2, it was incubated for 30 minutes at various temperatures, cooled and then added to 245 µL cells suspended in 15 mM Na$_3$PO$_4$, pH 8.0. D. PlySs2 was added to cells suspended in 15 mM Na$_3$PO$_4$, pH 8.0 along with various concentrations of ethylenediaminetetraacetate (EDTA) to determine if it requires a cofactor. In controls, dd H$_2$O replaced PlySs2 for all tests.
Figure 7B:
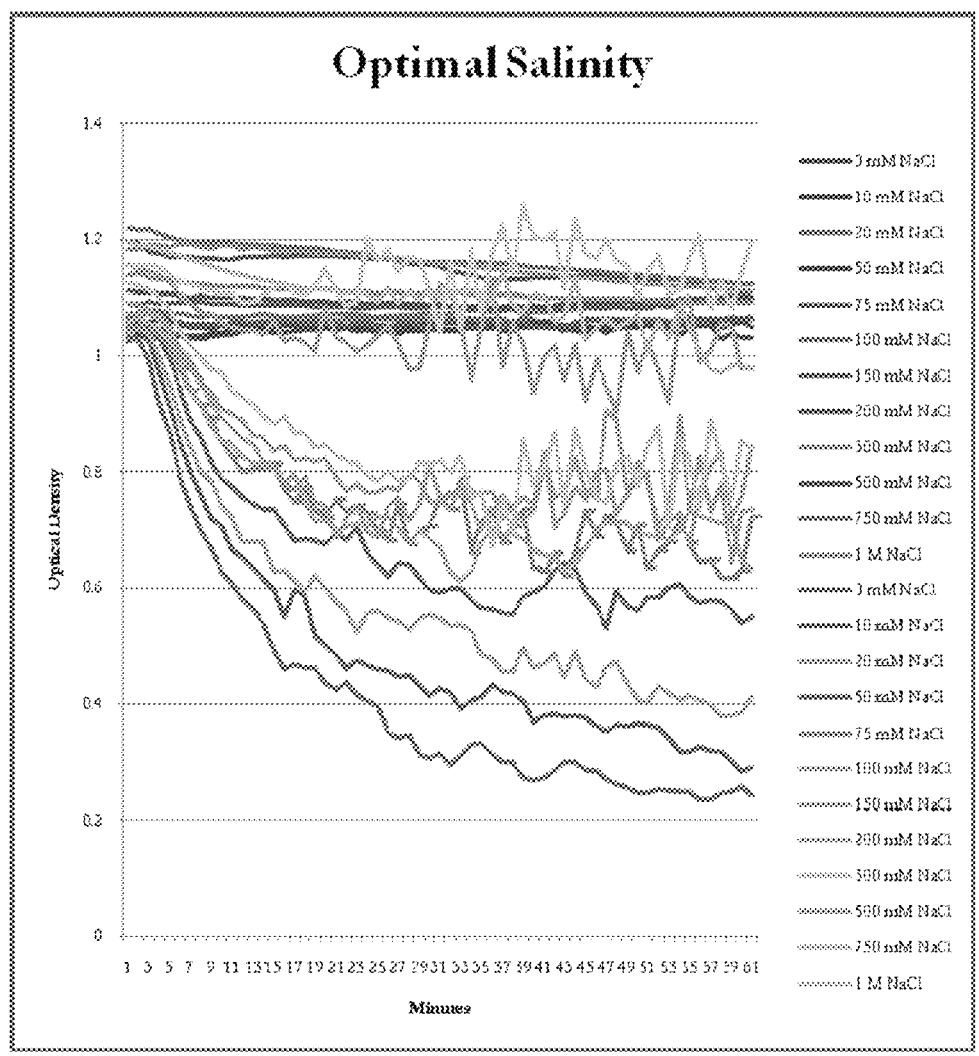

The *S. suis* lysins were further characterized and tested to determine biochemical conditions including optimal pH, optimal salinity, temperature stability, and the effect of EDTA. The activity was determined by the degree of *S. suis* 7997 turbidity reduction ($OD_{600}$) following the addition of PlySs2 at 32 µg/ml. Briefly, a 5 mL brain heart infusion (BHI) *S. suis* 7997 overnight culture was inoculated into 45 mL BHI and grown at 37° C. for 2 hours. The 50 mL culture was spun at 1,789 rcf for 10 min. A 50 mL culture of *S. suis* 7997 was centrifuged. The pellet was washed with 50 mL double-distilled $H_2O$ (dd$H_2O$) for the pH test, or 25 mL 15 mM $Na_3PO_4$, pH 8.0 for the other tests and centrifuged again. The pellet was then resuspended in enough dd $H_2O$ or 15 mM $Na_3PO_4$, pH 8.0 to bring the final $OD_{600}$ to ~1.0 for each test condition. In all controls, PB replaced PlySs2. Spectrophotometric readings were taken of each sample at $OD_{600}$ every minute over an hour. The overall results for optimal pH, optimal salinity, temperature stability and effect of EDTA are depicted in FIG. 7A-7D. The pH-dependence of the enzyme was first addressed using two buffer sets with adjacent pH ranges, citrate/phosphate: 4.6-8.0; and bis-tripropane (BTP): 7.0-9.7. NaCl, EDTA, and DTT were also varied to test conditions for PlySs2 activity. To determine optimal pH, PlySs2 activity was tested against *S. suis* strain 7997 in phosphate/citrate buffer at various pH levels (FIG. 7A). PlySs2 had the strongest activity at pH 8.0. We observed an extended spectrum of lysis at the highest pH values. Optimal pH was similarly determined against *S suis* strain 7997 this time using Bis-tris propane (BTP) buffer, which permitted assessment up to a higher pH level (FIG. 8). PlySs2 was shown to have acute activity up to a pH of 9.7. In BTP, lysis was maximal at the highest pH, 9.7, but this is not a suitable buffer for living cells. Lysis also occurred in BTP, pH 7.0-8.0; at commensurate pH-values, however, the magnitude of the OD-drop was much more pronounced in citrate/phosphate (a more physiological buffer for the growth of test cultures). There was activity down to pH 6.0, which is significant, because the pH of blood is approximately 7.4. To determine the optimal salt concentration, in 195 μl of cells, 5 μl lysin were added to 50 μl of various NaCl concentrations (FIG. 7B). PlySs2 had the greatest activity in 0 mM NaCl. The cells are more susceptible to lysis within a more hypotonic solution. Salt did not enhance PlySs2-induced lysis. At constant enzyme concentrations, bacteriolysis decreased from 0-1000 mM NaCl. Therefore, 0 mM NaCl is optimal, because cells are more susceptible to lysis within a more hypotonic solution.

Figure 7C:
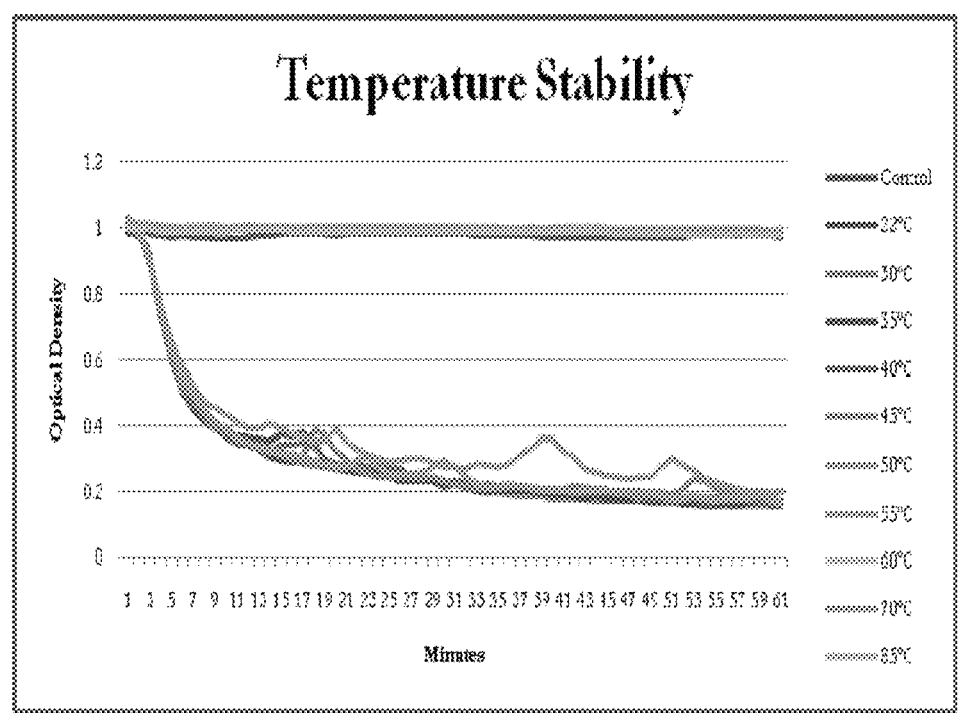
Figure 7D:
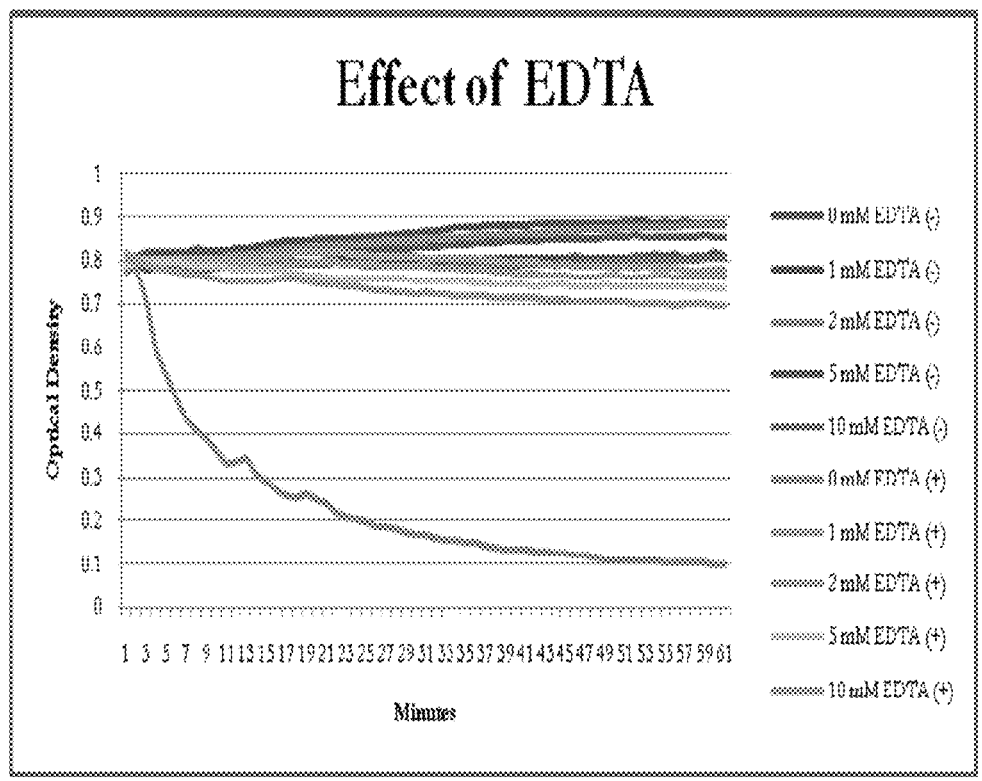
Figure 8:
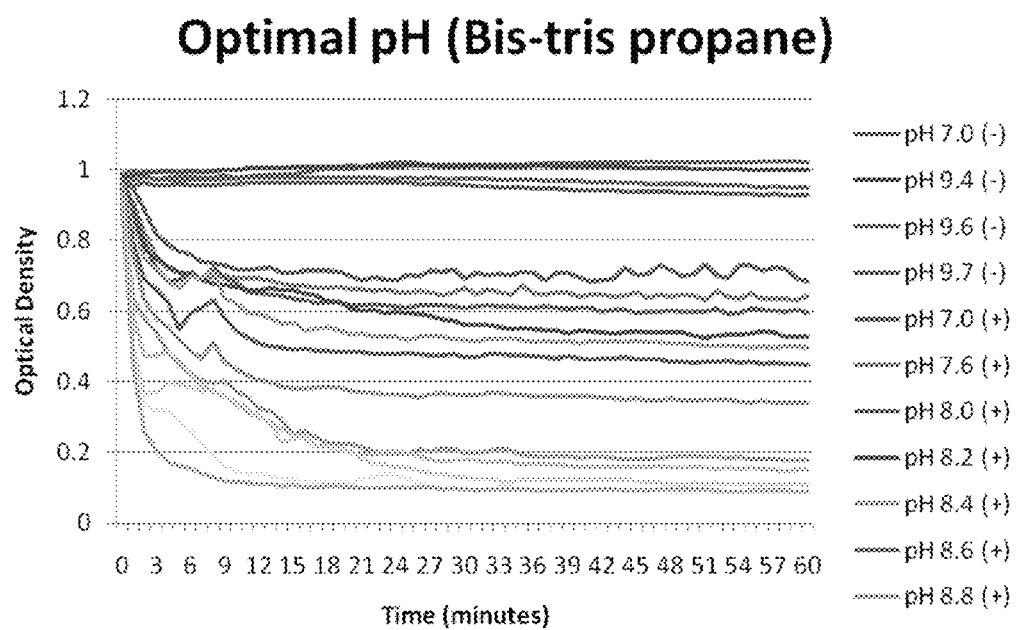
FIG. 8 depicts optimal pH of PlySs2 determined against S. suis strain 7997 in Bis-tris propane (BTP) buffer up to a higher pH level.

To determine the temperature stability of lysin, it was incubated for 30 minutes at various temperatures, cooled and then added to 245 μl cells suspended in 15 mM $Na_3PO_4$, pH 8.0 (FIG. 7C). Exposure of PlySs2 to an excess of DTT had no impact (either positive or negative) on activity (data not shown). Treatment with EDTA impeded PlySs2-induced lysis of *S. suis*. Lysin was added to cells suspended in 15 mM $Na_3PO_4$, pH 8.0 along with various concentrations of ethylenediaminetetraacetate (EDTA) to determine if it requires a cofactor. In controls, dd $H_2O$ replaced lysine (PlySs2) for all tests. Very low concentrations of ethylenediaminetetraacetate (EDTA) diminish PlySs2 activity (FIG. 7D). This signifies that PlySs2 requires a cofactor or some other modifier. Lysin (PlySs2) was tested with EDTA at very low concentrations to determine what level would allow some residual activity. At that level (between 4 uM and 200 uM EDTA), low (5-50 uM) amounts of different divalent cations ($Ca^{2+}$, $Fe^{2+}$, $Mg^{2+}$, $Mn^{2+}$, $Ni^{2+}$, $Zn^{2+}$) are added to determine the cofactor.

Figure 9:
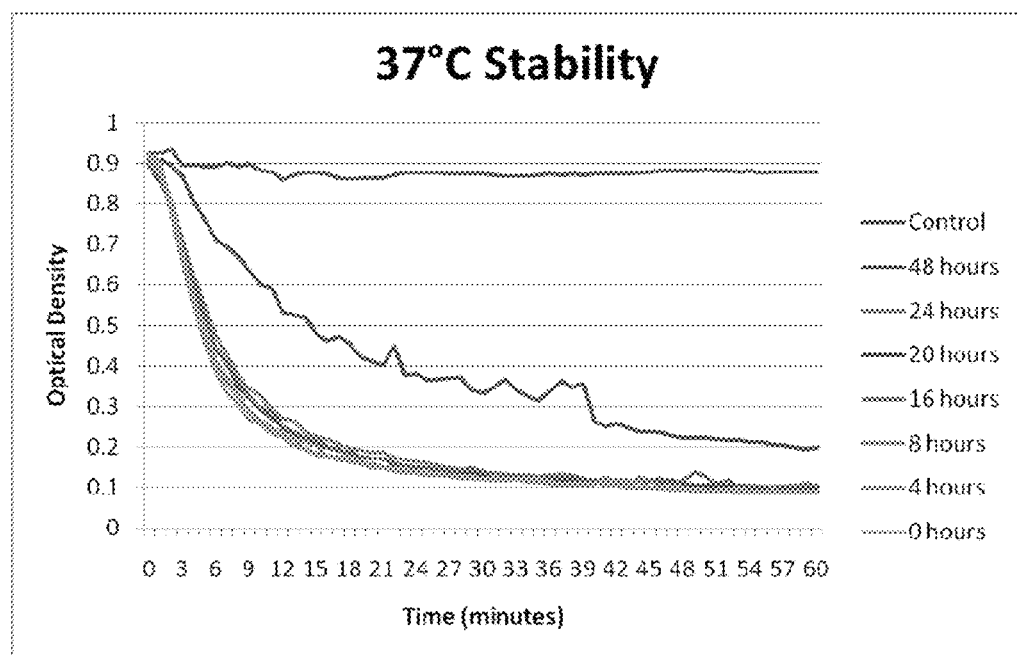
FIG. 9. The stability of purified PlySS2 was determined by evaluating killing effectiveness against strain 7997 after storage at 37° C. for up to 48 hours in buffer.
Figure 10:
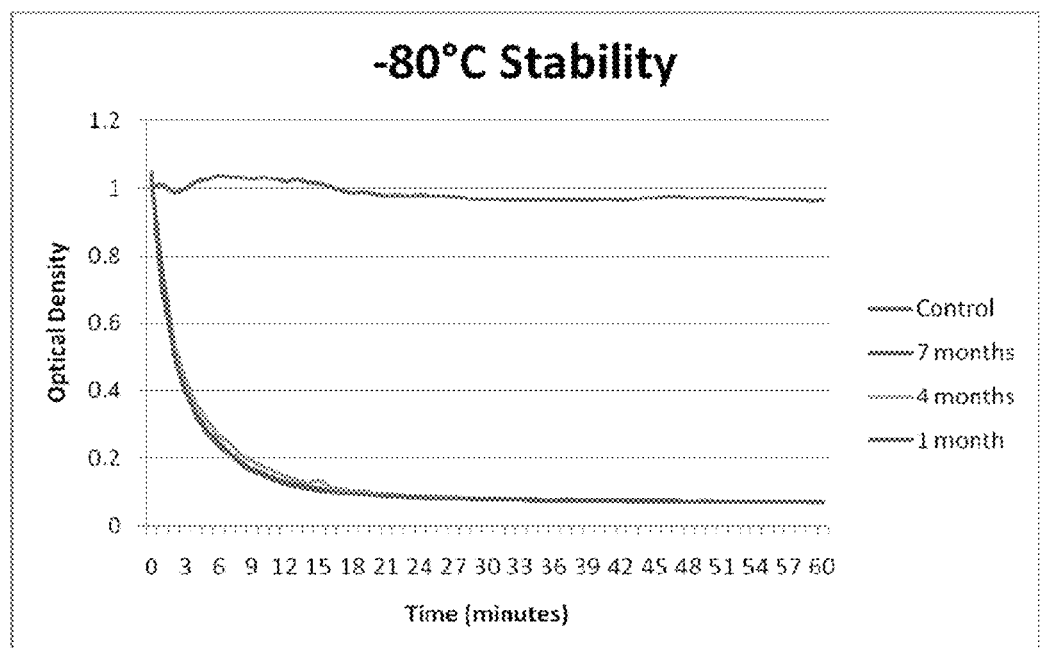
FIG. 10. Killing effectiveness, assessed by OD$_{600}$ growth of strain 7997 upon treatment with PlySs2 lysin after lysin storage at −80° C. for up to 7 months in buffer.

The stability of PlySs2 was tested when incubated at: different temperatures for 30 minutes; 37° C. for hours; 4° C. for days; and −80° C. for months. The activity of each aliquot (at 32 μg/ml) against *S. suis* 7997 was spectrophotometrically determined as outlined above. PlySs2 was also tested after one to ten consecutive room temperature to −80° C. freeze-thaws. When incubated at 22° C.-85° C. for 30 min, PlySs2 activity was principally unaffected through a significant temperature range, including 55° C.; at 60° C., PlySs2 activity was completely abolished. After incubation at 37° C. for 24 hours, PlySs2 retained full activity; but after a 48-hour 37° C. incubation, PlySs2 showed diminished activity. There was no observable decrease in activity after 15 days of 4° C. incubation. In addition, PlySs2 lasted over 7 months at −80° C. without a reduction in activity. The lysin can endure 10 consecutive room temperature to −80° C. freeze-thaws without any observable effect on its activity. The stability of purified PlySs2 lysin was determined upon maintenance at 37° C. for up to 48 hours in buffer. Killing effectiveness was determined against *S. suis* strain 7997 periodically, as shown in FIG. 9. The PlySs2 lysin is >90% stable up to 24 hours and maintains at least 50% activity after 48 hours Stability of the PlySS2 lysin was evaluated on freezer storage at −80° C. The PlySs2 lysin retains essentially 100% activity on storage in buffer for up to at least 7 months at −80° C. (FIG. 10).

Investigations to determine the bond catalyzed by PlySs2 lysin have been undertaken. PlySs2 was incubated with purified *S. suis* peptidoglycan stripped of lipotechoic acid and carbohydrates overnight at 37° C. and the product submitted for mass spectroscopy. Data suggest that the cleavage is an N-acetylmuramoyl,-L-alanine amidase.

Biochemical Characterization of PlySs1

A prophage lytic enzyme was cloned from a functional genomic screen of *S. suis* strain 7711, a serotype 7 isolate originating from the Netherlands1. The complete PlySs1 lysin gene encodes a 452-residue protein: Pfam analysis predicts a type 5 alanine-amidase domain (PF05832) at the N-terminus, followed by a double CPL-7 cell-wall binding domain (PF08230) in the central region, and a secondary glucosaminidase domain (PF01832) at the C-terminus. Architecturally, the domain arrangement of the cloned lysin is highly atypical. Gram-positive lysins typically consist of an N-terminal enzymatic domain and a C-terminal binding domain. While occasionally lysins are seen with two N-terminal lytic domains, it is rare for a second enzymatic functionally to be encoded after the binding domain. One example is the LambdaSa2 lysin of *S. agalactiae* (Pritchard D G et al (2007) Appl Environ Microbiol 73(22):7150-7154). Working with LambdaSa2, Donovan and Foster-Frey surprisingly observed increased enzymatic activity following removal of the C-terminal glucosaminidase domain (Donovan D M and Foster-Frey J (2008) FEMS Microbiol Lett 287(1):22-33). With this motivation, we engineered a truncated construct of the cloned lysin with only the N-terminal enzymatic and central binding domains. This truncated construct was expressed and purified for subsequent functional analysis; activity and characterization studies described herein were based on the truncated PlySS1; herein it is referred to as truncated PlySs1 or ΔPlySs1. As above noted, the structure and amino acid sequence of the full length and truncated PlySs1 lysin is depicted in FIG. 3.

Figure 11A:
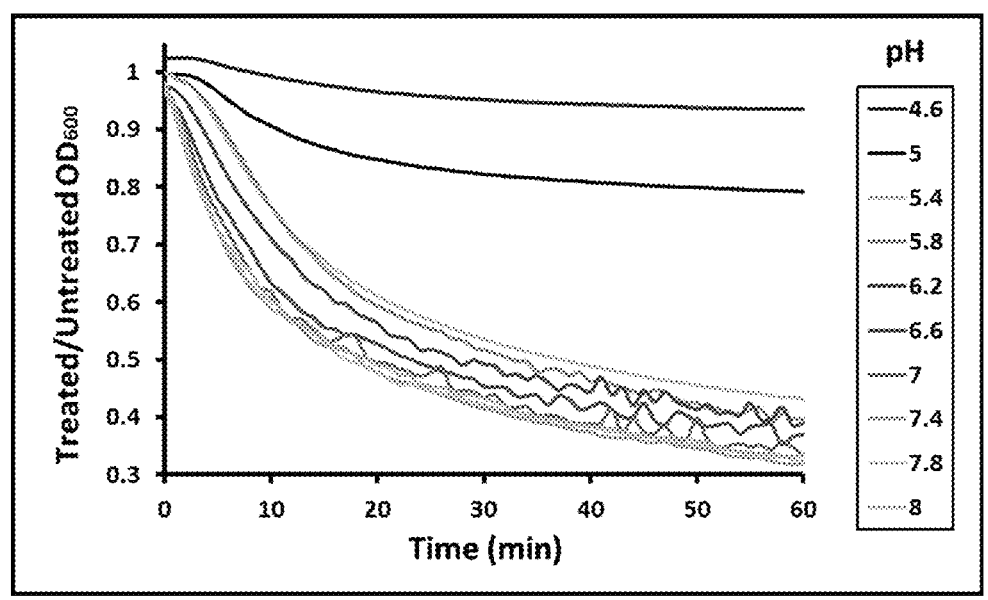
FIGS. 11A and 11B depicts ΔPlySs1 pH dependence. (A) Cells of host strain 7711 were suspended in phosphate citrate buffer (40/20 mM) at a range of pH-values from 4.6 to 8.0. ΔPlySs1 was added (110 µg/ml) and OD600 was measured over 60 min (horizontal axis) at 37° C. The vertical axis represents the treated/untreated OD600-ratio at each timepoint. For each pH-value, the curve depicts the running average of 3 independent experiments. Overall, activity was maximal at the upper end of the buffering range. (B) Here, bis-tris-propane (40 mM) was employed as the buffering agent with a pH-range from 7.0 to 9.7; ΔPlySs1 was again added to 110 μg/ml. Each curve depicts the running average of 3 experiments. Maximal activity was observed at pH=9.0, although the quantitative degree of OD-decline was, in general, less than in phosphate-citrate.
Figure 11B:
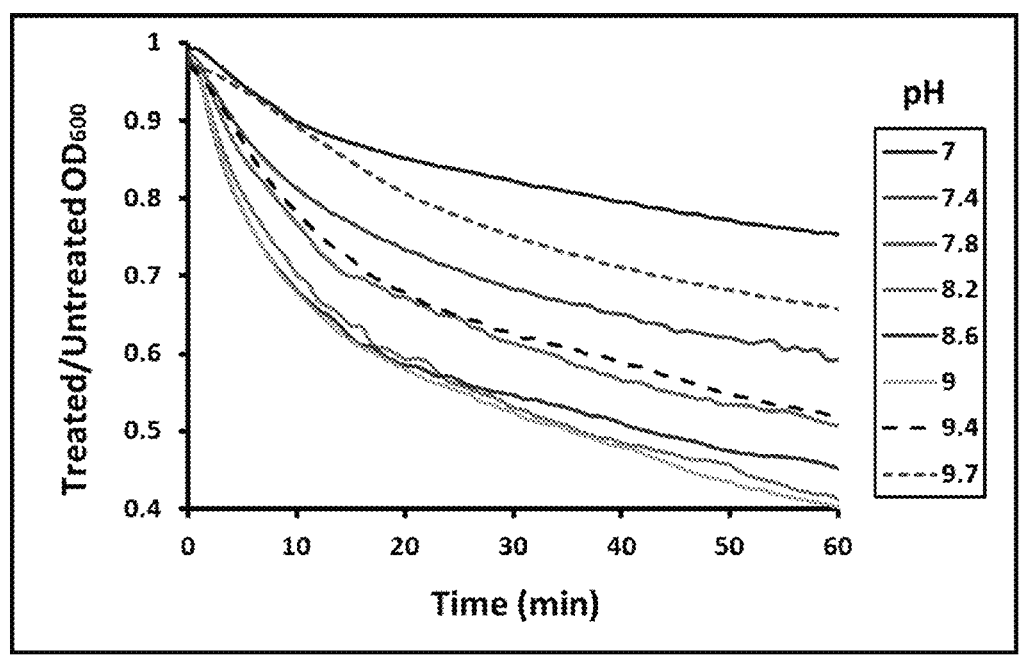

The optimal biochemical conditions for PlySs1 were determined against live cells of the encoding *S. suis* strain (7711). For these experiments, activity was gauged through the degree of turbidity reduction ($OD_{600}$) of an aqueous bacterial suspension following the addition of lysin. The pH-dependence of the enzyme was first addressed using two buffer sets with adjacent pH ranges, citrate/phosphate: 4.6-8.0; and bis-tris-propane (BTP): 7.0-9.7. An extended spectrum of lysis was observed, from 5.4-9.4 (FIG. 11A). In BTP, lysis was maximal from 8.2-9.0; at commensurate pH-values, however, the magnitude of the OD-drop was slightly more pronounced in citrate/phosphate (FIG. 11B).

Figure 12:
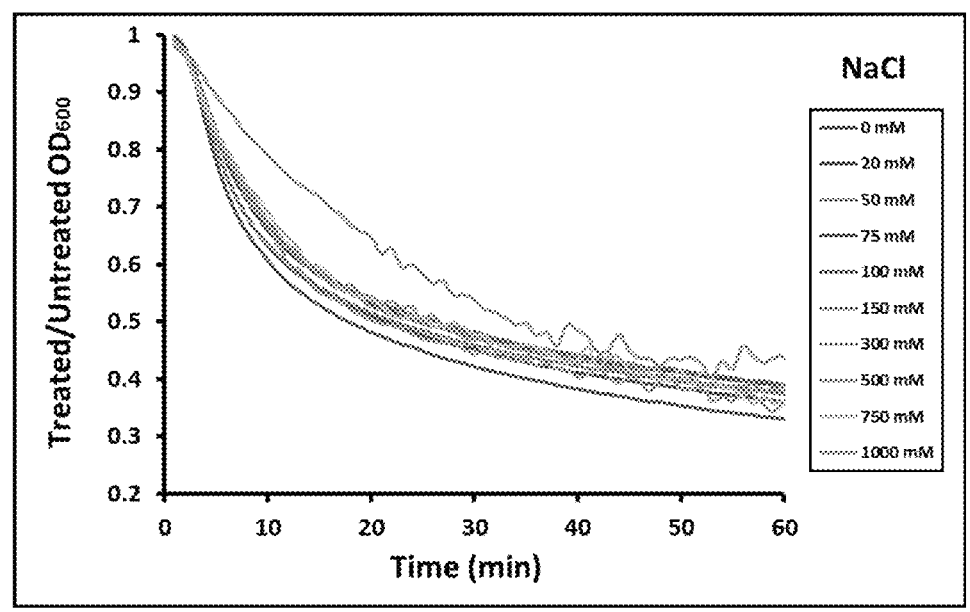
FIG. 12 depicts ΔPLySS1 NaCl dependence. S. suis 7711 cells were suspended in phosphate-citrate buffer pH=7.8 (40/20 mM). NaCl was added to the above concentrations, followed by ΔPlySs1 at 110 μg/ml. Optical density at 600 nm was observed over 60 min at 37° C. In this figure, the vertical axis represents the treated/untreated $OD_{600}$-ratio for each NaCl concentration, averaged over 3 independent experiments.
Figure 13A:
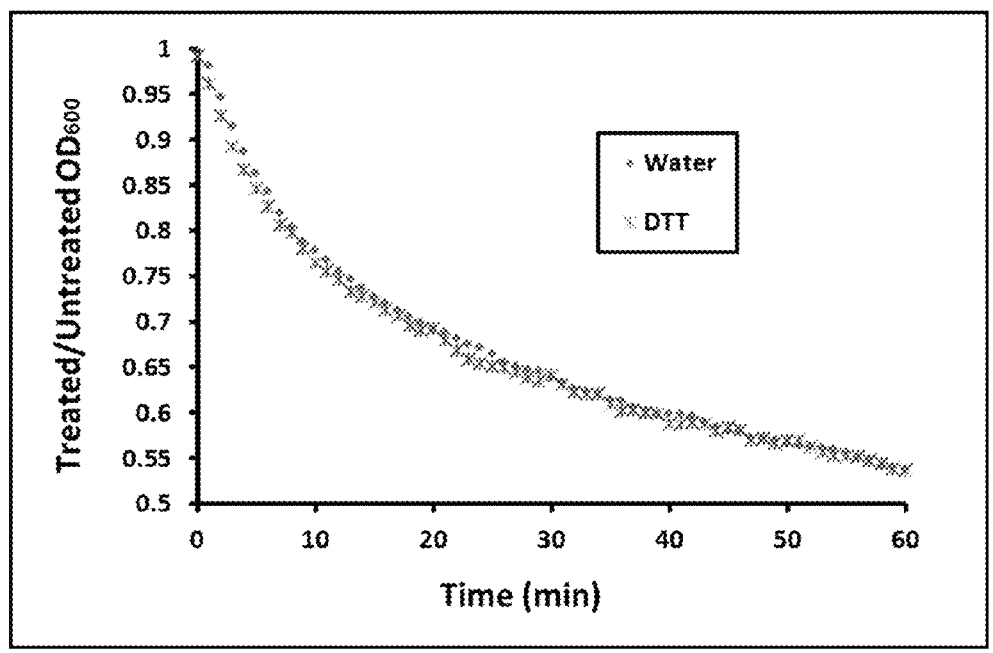
FIGS. 13A and 13B provides assessment of ΔPlySs1 DTT and EDTA susceptibility. (A) ΔPlySs1 was pre-incubated for 1 hr with 5 mM DTT (a large molar excess) prior to addition to 7711 cells; activity was unchanged. (B) Here, various concentrations of EDTA were included in the buffered suspension of cells prior to addition of ΔPlySs1 (110 μg/ml lysin). For both images, the vertical axis represents the treated/untreated $OD_{600}$-ratio for each condition, averaged over 3 independent experiments.
Figure 13B:
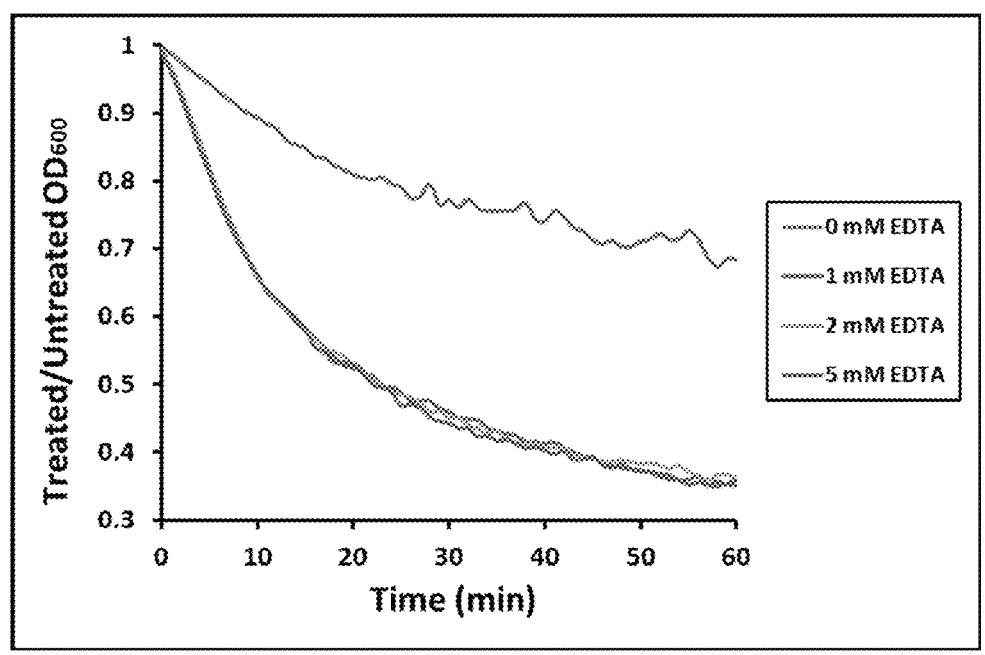
Figure 14A:
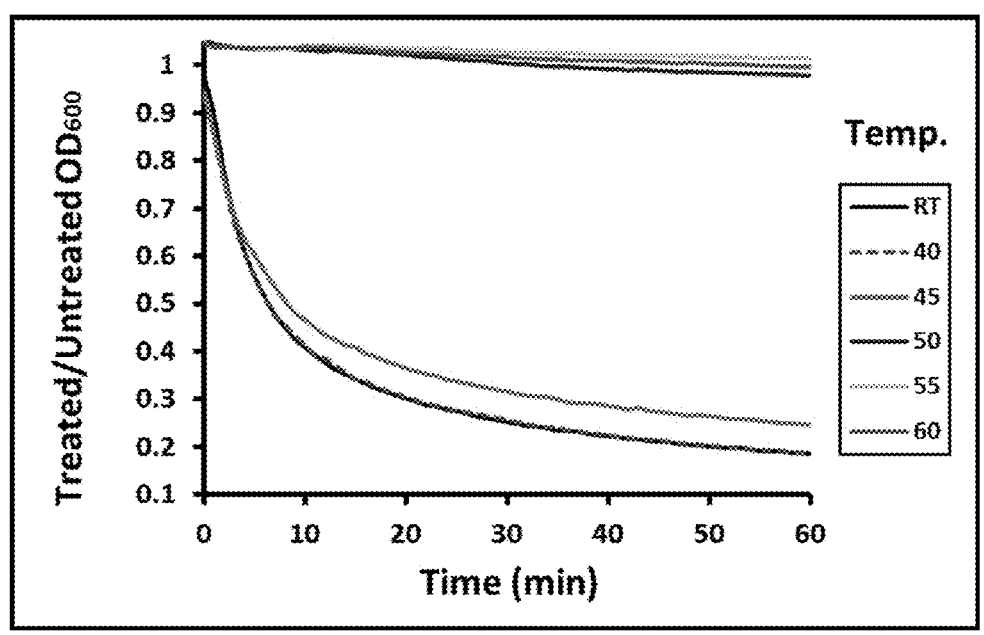
FIGS. 14A and 14B shows ΔPlySs1 temperature stability. (A) A ΔPlySs1 stock solution was held at each of the above temperature for 30 minutes, followed by addition to 7711 cells (270 μg/ml final enzyme concentration, final temperature=37° C., ideal buffering conditions). The curves in this image represent running averages of 3 individual experiments. In each case, complete loss of activity was observed between the 45° C. and 50° C. samples. The 3 hottest samples show a slightly higher $OD_{600}$ reading than the untreated control due to flocculation of ΔPlySs1 upon denaturation. (B) The above experiment was repeated, but with 6 hours of heat-treatment prior to the assay. At this longer incubation time, the 45° C. sample showed some loss of activity, though not complete. The 40° C. sample maintained essentially native activity.
Figure 14B:
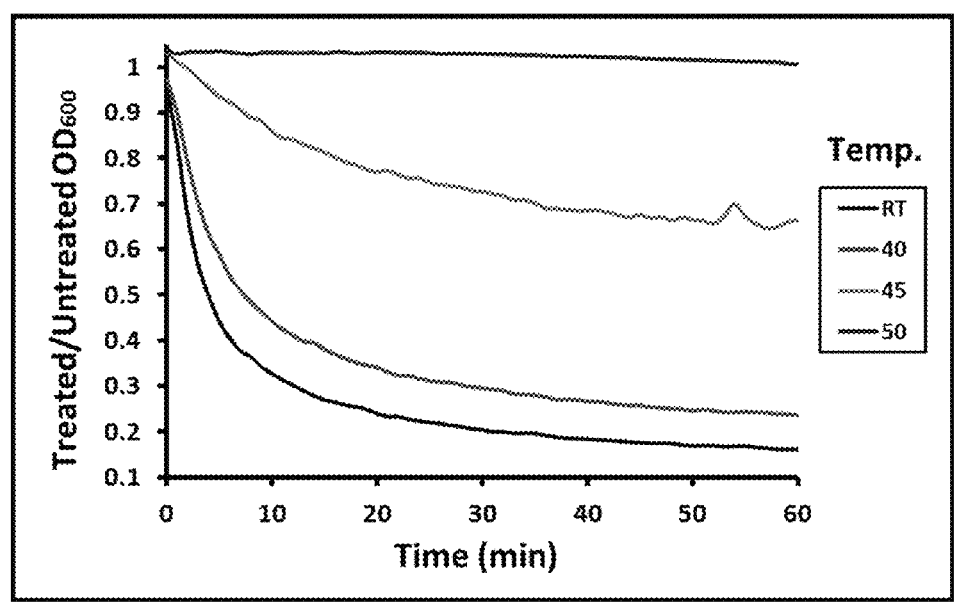

The role of salt concentration was likewise considered, although it did not greatly affect PlySs1-induced lysis. At constant enzyme concentrations, bacteriolysis varied little from 0-1000 mM NaCl, with only small numeric increases under the most hypotonic conditions (FIG. 12). Exposure of PlySs1 to an excess of DTT or EDTA did not negatively impact activity, indicating that the enzyme does not rely upon intramolecular disulfide bridges or chelatable cations as cofactors (FIGS. 13A and 13B). The thermal stability of PlySs1 was examined by incubating the enzyme at various elevated temperatures prior to use (the OD-drop experiment itself was always conducted at 37° C.). When held at 35° C.-60° C. for 30 min, lysin activity was virtually unaffected until 50° C., at which point it was completely abolished (FIG. 14A). For the 6-hr incubation, a partial decrease m activity was observed at 45° C., while the 40° C. sample was unaffected (FIG. 14B). The latter corresponds to typical porcine body temperature.

To determine the bond specificity of the enzymatic domain of PlySs1, purified *S. suis* cell walls (from type strain S735) were subject to double digestion with HEWL (a muramidase) and PlySs1. The two predominant peaks were m/z=718 and m/z=734. This corresponds exactly to the predicted masses of the [Na-M]+ and [K-M]+ adducts of GlcNAc-MurNAc-LAla-D-Gln. This suggests that PlySs1 possesses gamma-endopeptidase activity, cleaving the peptidoglycan stem between D-Gln and L-Lys as characteristic of a γ-D-glutaminyl-L-lysine endopeptidase. When a mass spectrum was taken of undigested cell wall, the above two peaks were absent.

quickly. However, it is unusual and remarkable in its broad activity against major pathogens. It is also notable that the lysin can be produced and purified readily, as shown above, and is stable in various relevant temperatures, pH and salinity, making it an attractive candidate therapeutic enzyme.

TABLE 1

| PlySs2 Reduction in Growth (Optical Density) of Different Bacteria | | | |
|---|---|---|---|
| None (0.3-0.8 drop in $OD_{600}$) | Slight (0.05-0.3 drop in $OD_{600}$) | Moderate (0.3-0.8 drop in $OD_{600}$) | Acute (>0.8 drop in $OD_{600}$) |
| Bacillus thuringiensis | Streptococcus sobrinus | Enterococcus faecalis | Streptococcus suis, Strain (Serotypes): 10 (2), 735 (2) 6112 (1), 6388 (1), 7997 (9), 8067 (9) |
| Bacillus cereus | Streptococcus rattus | Streptococcus dysgalactiae - GGS | Staphylococcus epidermidis |
| Bacillus subtilis | | Streptococcus agalactiae - GBS - 090R | Staphylococcus simulans |
| Bacillus anthracis | | Streptococcus pyogenes - GAS | Staphylococcus aureus |
| Escherichia coli | | Streptococcus agalactiae - GBS - Type II | Lysteria monocytogenes |
| Enterococcus faecium | | | |

EXAMPLE 2

In Vitro Testing of Lysin Specific Activity

PlySs2 Activity

To determine PlySs2 lysin activity against different cell types, 5 μL of 1.6 μg/μL (8 μg) of PlySs2 was added in a microtiter well to 245 μL of cells (suspended in 15 mM $Na_3PO_4$, pH 8.0). In a corresponding well as control, 5 μL dd $H_2O$ was added to 245 μL of cells. Readings ($OD_{600}$) were taken for each well in a spectrophotometer every minute over an hour. The OD density indicates the amount of bacterial cell growth in the microtiter well.

Figure 15A:
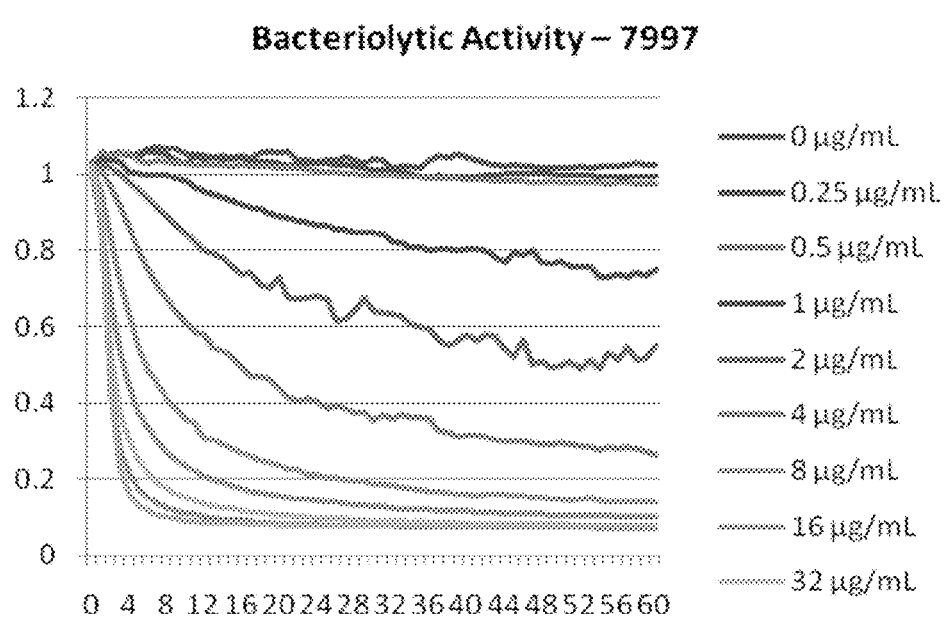
FIGS. 15A and 15B (A) PlySs2 has acute lytic activity against S. suis strain 7997 at, or above 8 ug/mL. (B) Activity of PlySs2 assessed in vitro against S. suis strain S735.
Figure 15B:
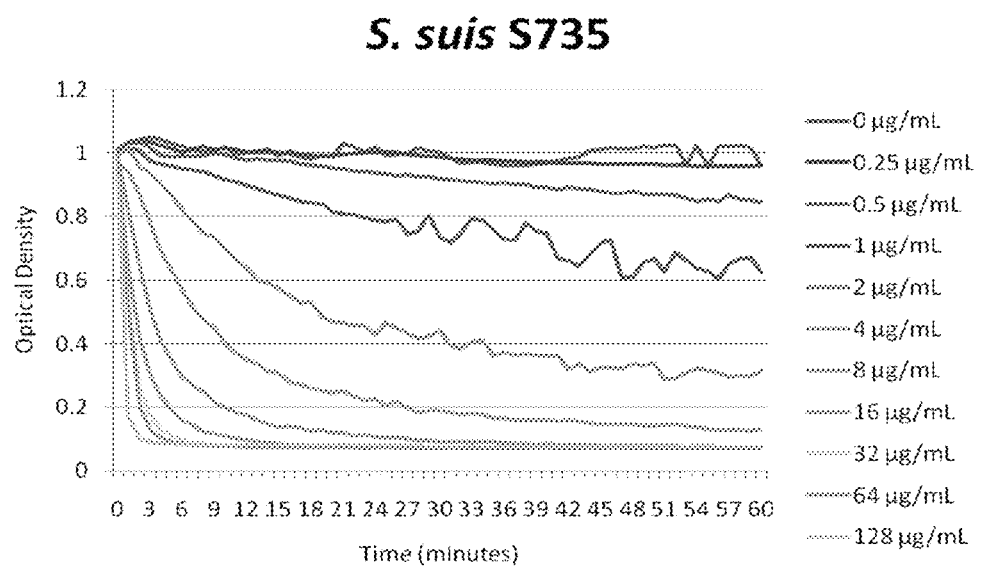
Figure 16A:
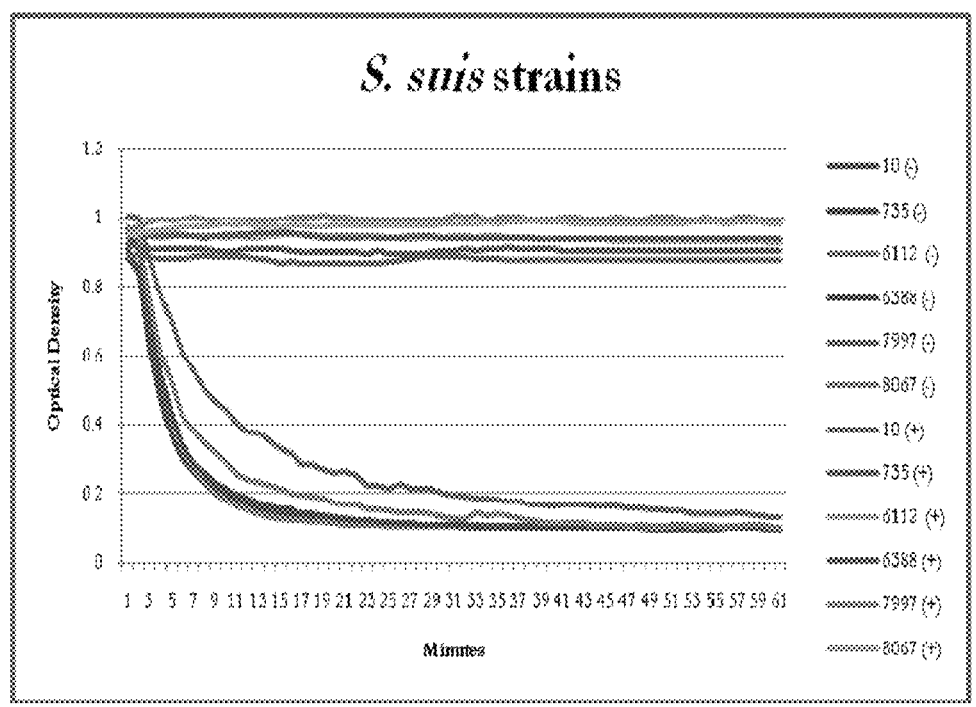
FIG. 16A-16D provides PlySs2 activity against different species and strains. S. suis 7997 was used as a positive control for each test. A. PlySs2 activity against strains of S. suis. B. PlySs2 activity against different species of bacteria and 2 strains of S. suis. C. Streptococci and staphylococci sensitivity to PlySs2. D. Various species tested for susceptibility to PlySs2 treatment.
Figure 16B:
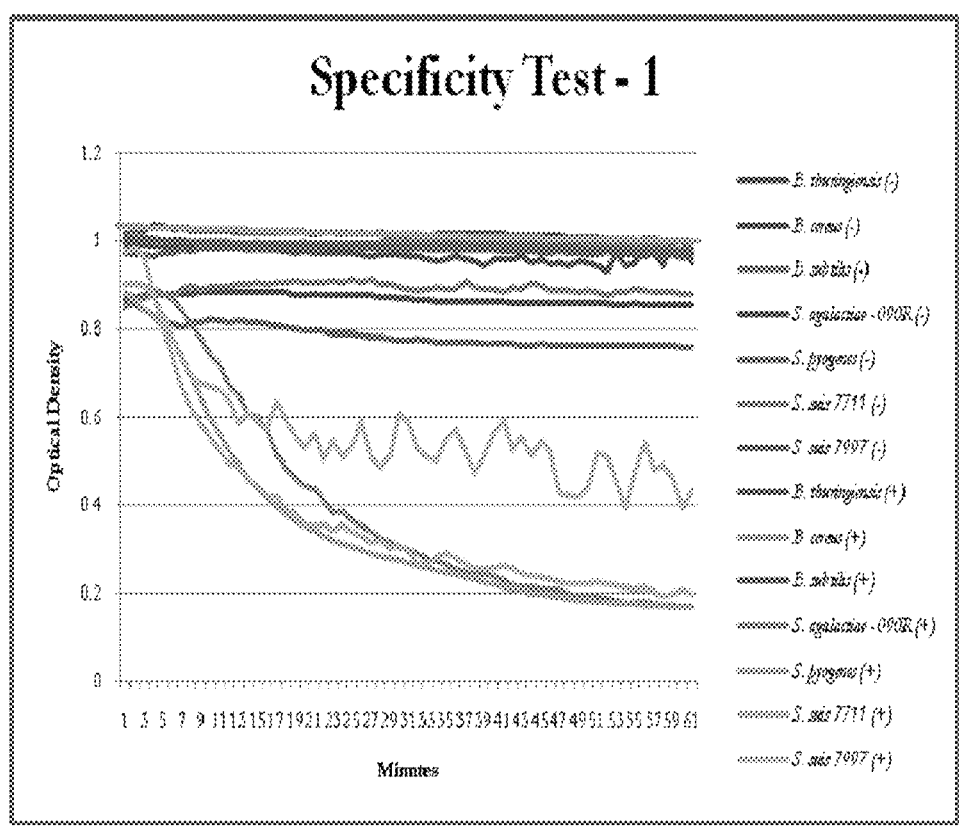
Figure 16C:
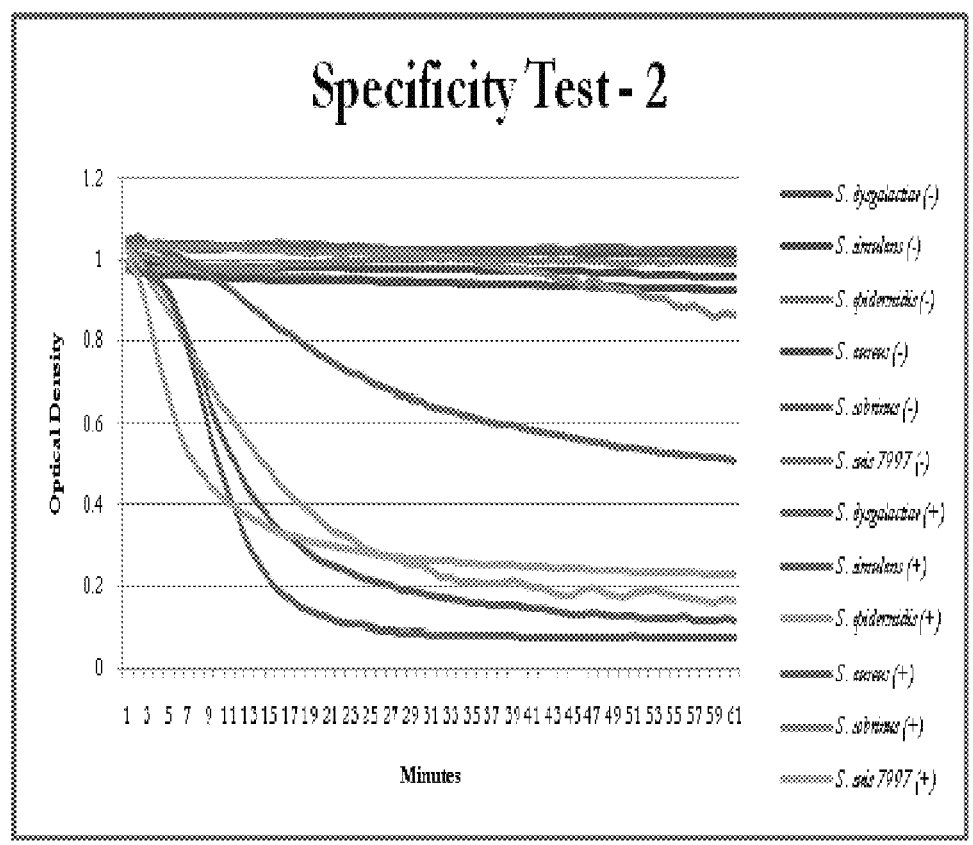
Figure 16D:
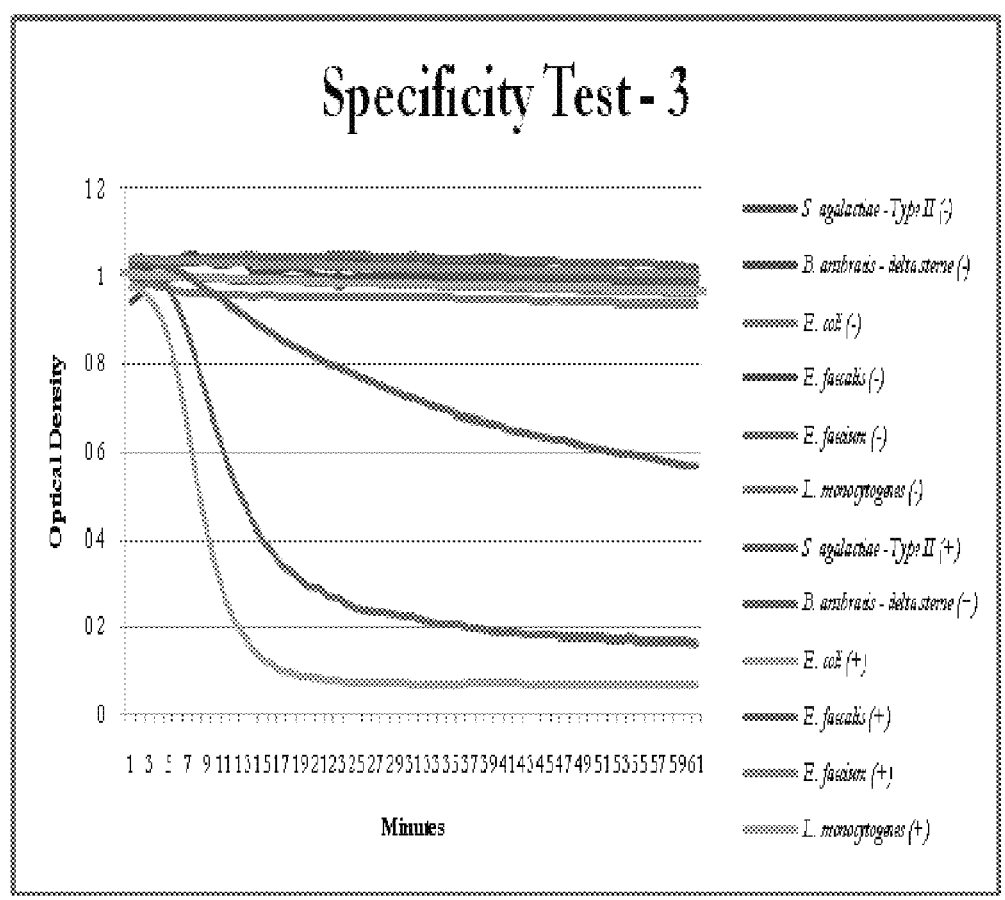
Figure 17A:
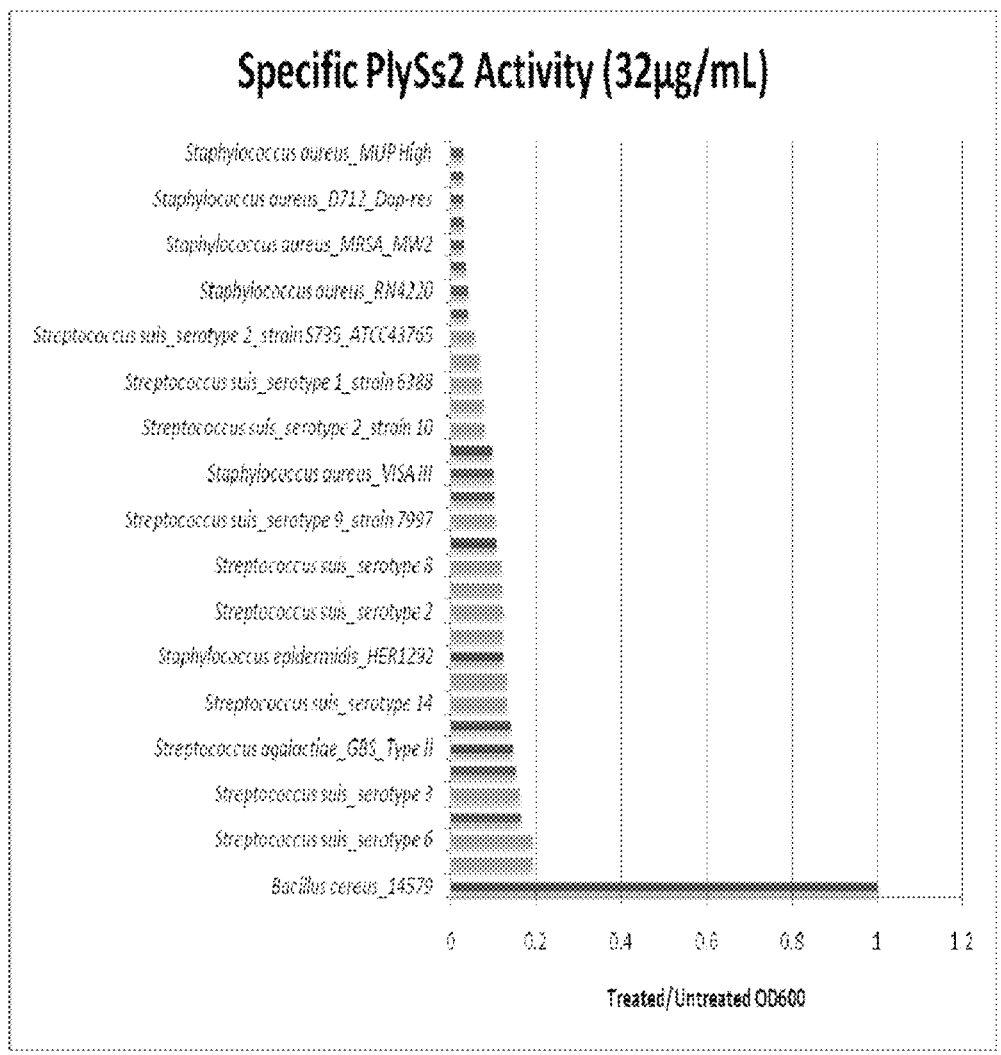
FIGS. 17A and 17B shows PlySs2 activity against multiple species, serotypes, and strains of bacteria. In each instance the Treated/Untreated $OD_{600}$ is depicted in a bar graph. The bars of S. aureus strains are colored red; bars corresponding to S. suis strains are orange. The bars of bacteria Listeria and other bacteria of interest are shown in purple.
Figure 17B:
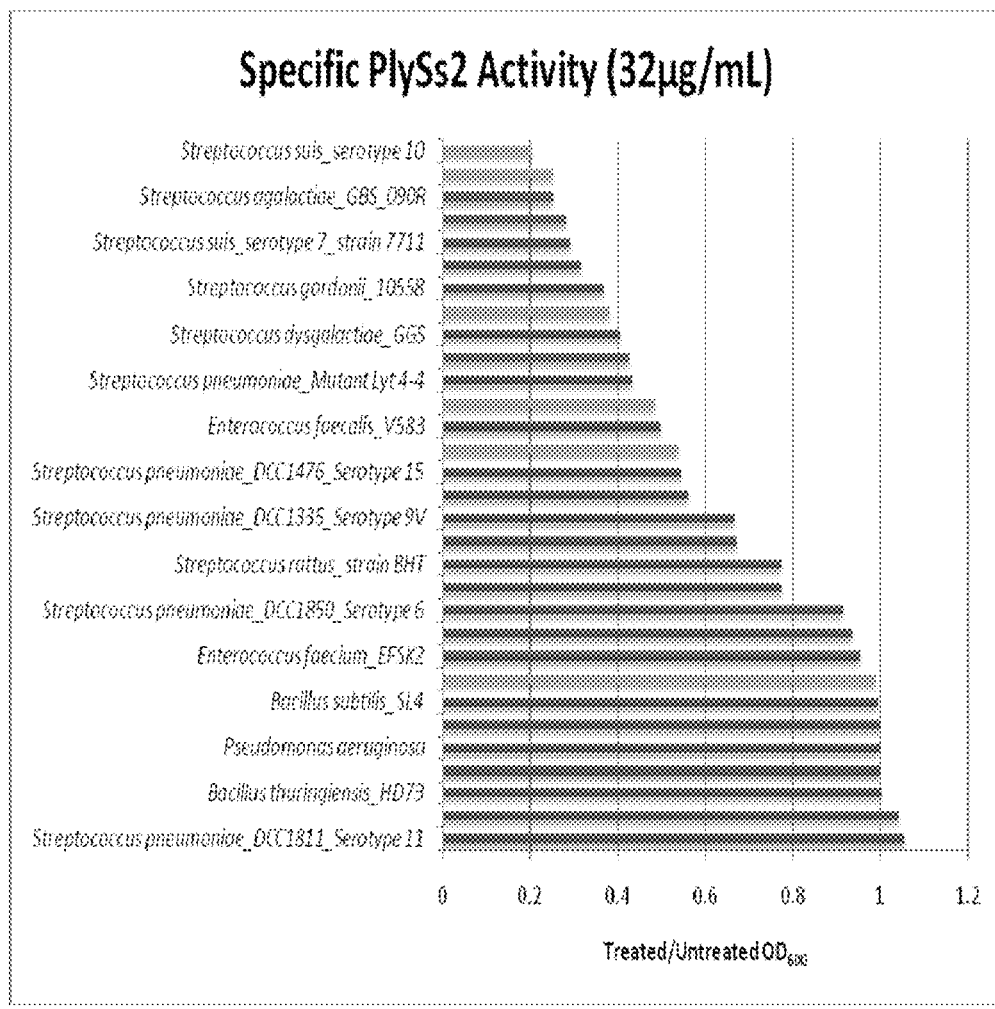

This activity test was first determined for the pathogenic S. suis strain 7997 with various concentrations of PlySs2 (FIG. 15A). Specific activity of purified PlySs2 lysin was also assessed in vitro against S. suis strain S735 (FIG. 15B). This test was then performed using 32 ug/mL PlySs2 to determine PlySs2 activity against other species of bacteria (it was found that based on lytic assay this was a good concentration for killing studies in vitro against other organisms) (FIG. 16A through 16D). Further strain killing results are shown in FIGS. 17A and 17B. Additional results are tabulated below in TABLE 1.

Figure 18:
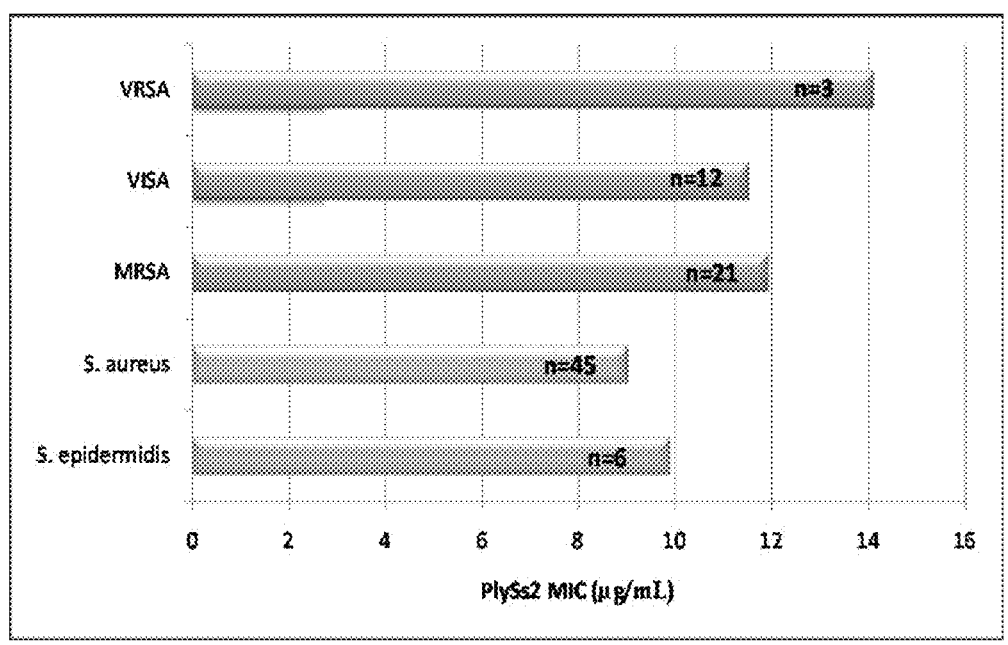
FIG. 18. PlySS2 was tested by standard MIC analysis for its ability to kill strains of staphylococci. Included in the testing were resistant staphylococci such as Vancomycin resistant (VRSA), Vancomycin intermediate (VISA) and methicillin resistant (MRSA) staphylococci. The three VRSA strains tested represent half of all known isolates.

As demonstrated and depicted in the above results, the PlySs2 lysin enzyme has broad activity killing not only against S. suis, but other pathogens particularly including S. aureus, S. pyogenes, Listeria and Group B streptococci. The results shown demonstrate reduction in growth and killing of methicillin resistant Staphylococcus aureus strains (MRSA). In comparable in vitro tests, PlySs2 is additionally and similarly effective against vancomycin intermediate sensitivity Staphylococcus aureus (VISA) and vancomycin resistant Staphylococcus aureus (VRSA) strains (FIG. 18).

Figure 19:
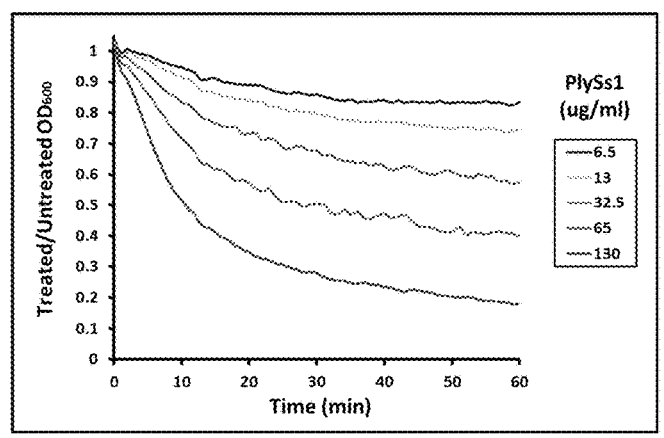
FIG. 19 provides ΔPlySs1 bacteriolytic activity. Depicted here are OD-drop curves for three strains of S. suis: 7711, the serotype 7 strain from which PlySs1 was originally cloned (i.e. the host strain); S735, a serotype 2 isolate that is the type-strain for the species; and 7997, a virulent serotype 9 strain. Bacteria were suspended in 20 mM phosphate buffer pH 7.8, 2 mM EDTA (defined as optimal conditions). ΔPlySs1 was added to the cells at a range of concentrations (indicated by the inset). For each sample, optical density at 600 nm (vertical axis) was measured over the course of an hour (horizontal axis) at 37□C. In this image, all curves represent running averages of 3 or 4 independent experiments.
Figure 19:
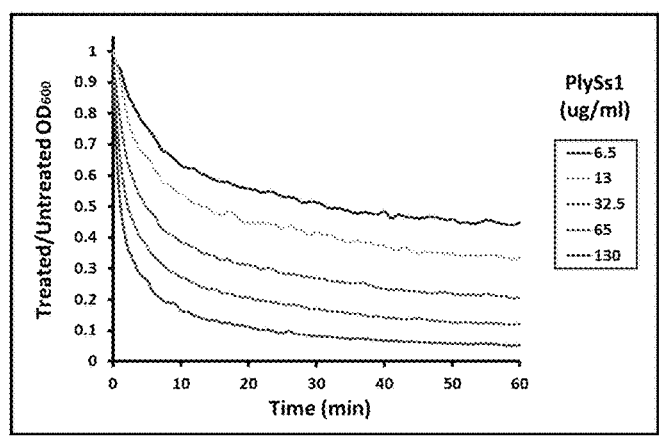
Figure 19:
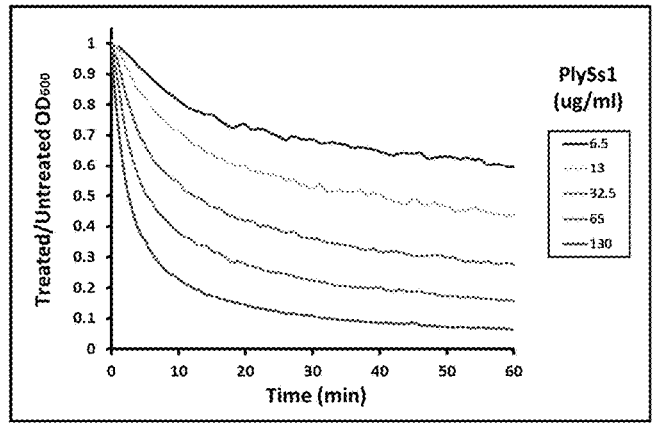
Figure 20:
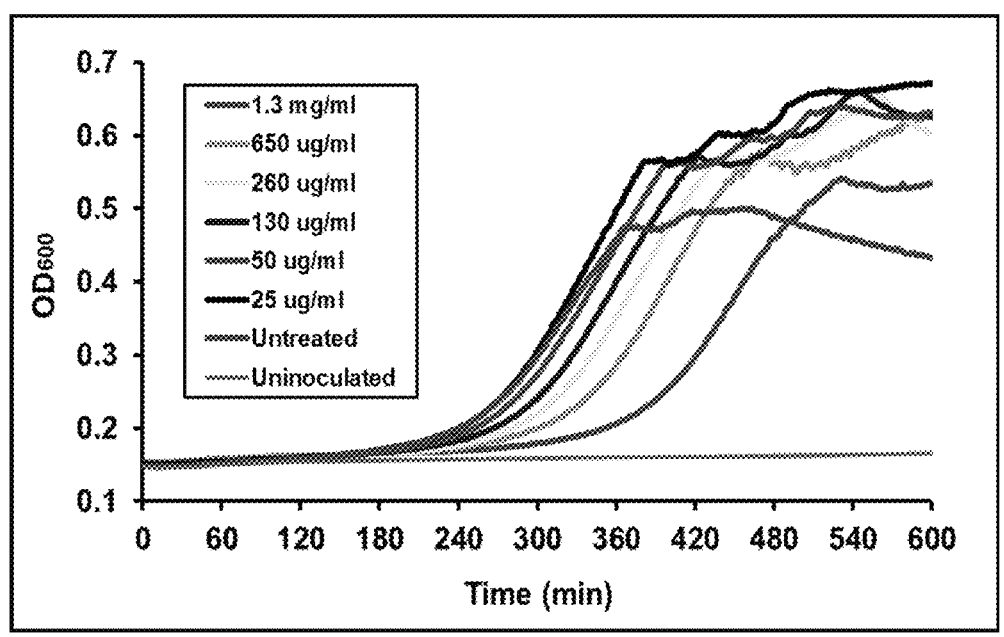
FIG. 20 shows ΔPlySs1 growth inhibition of S. suis 7711 ΔPlySs1 was added at the above final concentrations to a dilute suspension of S. suis strain 7711 in BHI broth. The optical density of each sample was measured continuously overnight in 96-well plate format. Overall, bacterial growth was delayed in a dose-dependent manner. However, for enzyme-concentrations that were sufficient to induce lysis in buffered solutions (130 and 50 ug/ml), the effect was quite minimal here. Moreover, none of the above ΔPlySs1 concentrations inhibited growth outright—hence, a MIC could not be assigned. For all of the treated samples, one will note that the final optical densities are actually higher than that of the untreated sample. This is an artifact of the accumulation of aggregated bacterial debris that occurred in the presence of lytic enzyme.

This S. suis lysin is similar to previously identified and characterized lysins in its ability to kill pathogenic bacteria PlySs1 Activity Truncated PlySs1(ΔPlySs1) lysin activity was determined against different cell types. Given the above experiments, the following optimal buffering conditions were employed for all further in vitro experiments with ΔPlySs1: 20 mM phosphate buffer, pH=7.8, 2 mM EDTA. A range of lysin concentrations, from 6.5-130 μg/ml, were introduced to live S. suis cells in this buffer. Three strains were considered particularly relevant: 7711, the serotype 7 strain that encodes PlySs1; S735, the serotype 2 reference strain; and 7997, a highly virulent serotype 9 strain. For each of these strains, the time-dependent OD600 response at various PlySs1 dosages is given in FIG. 19. In terms of bacterial viability, only the highest PlySs1-concentration (130 μg/ml) led to a >90% decrease in CFUs for 7711, S735, and 7997 after 1 hr treatment (TABLE 2). The lysin was also tested against actively-dividing cells in broth culture (strain 7711) (FIG. 20). Although it delayed bacterial proliferation in a dose-dependent manner, these effects were generally mild and ΔPlySs1 could not inhibit S. suis growth outright.

TABLE 2

| CFU Analysis of Strains 7711, S735 and 7997 | | |
|---|---|---|
| Strain | 13 μg/ml | 130 μg/ml |
| S735 (ST2) | 80.4%-92.6% | 95.4%-99.5% |
| 7997 (ST9) | 16.8%-30.3% | 89.9%-93.9% |
| 7711 (ST7) | 0%-35.6% | 95.3%-99.2% |

For two ΔPlySs1 concentrations (130 and 13 μg/ml), CFU analysis was conducted on S. suis strains S735, 7997, and 7711 after 1 hr treatment (optimal buffering conditions). In each experiment, the percentage-decrease in CFUs was determined for the treated sample versus the untreated. The range of the values observed (across 3 independent experiments) is reported here for each strain. The serotype of each strain is indicated m parentheses.

Figure 21:
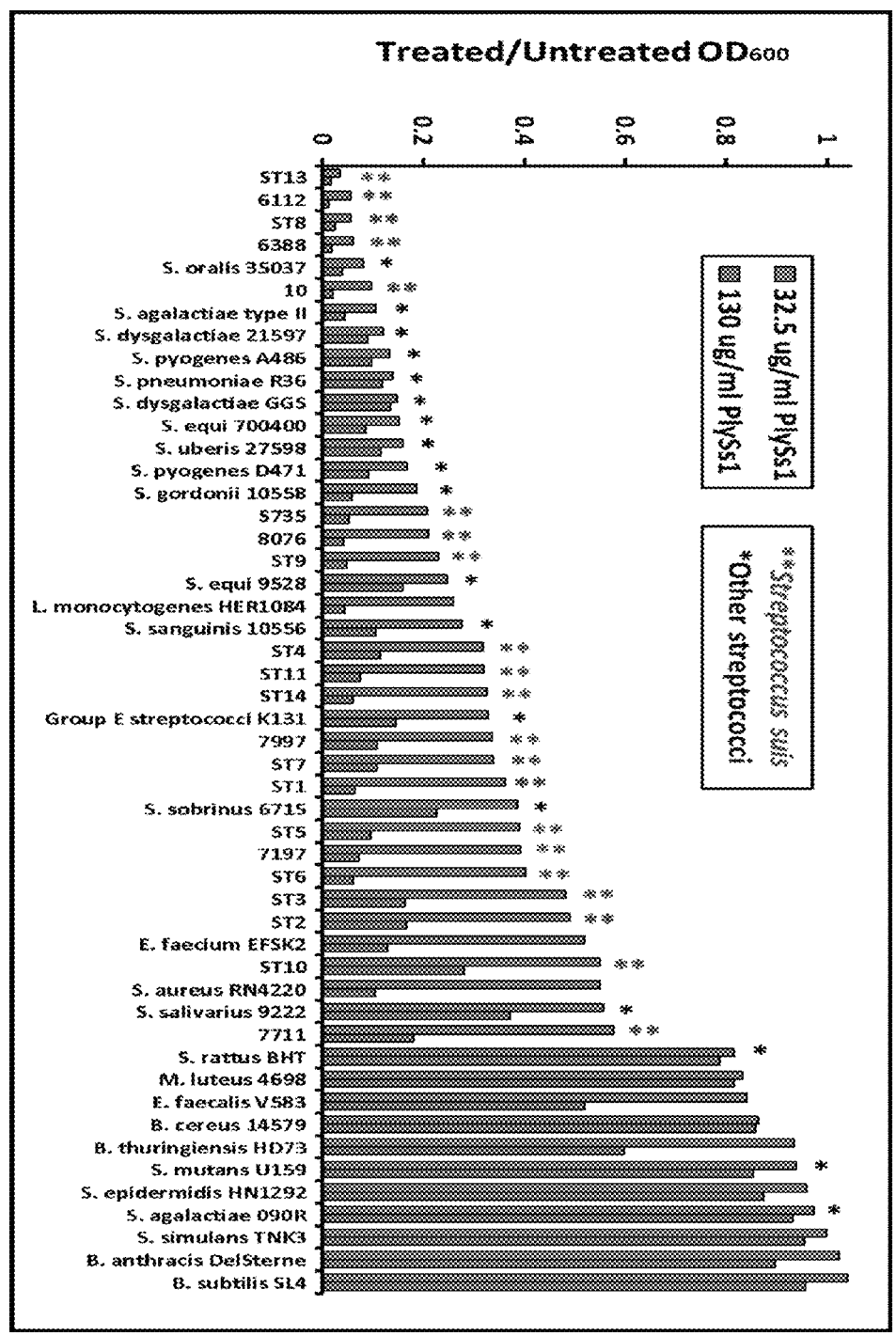
FIG. 21 provides a ΔPlySs1 bacterial strain panel. The information provided m FIG. 19 and Tables 3 and 4 is summarized graphically for two PlySs1 concentrations, 130 μg/ml and 32.5 μg/ml. In the image, strains of S. suis are denoted with double red asterisks and non-suis streptococci are denoted with single black asterisks. The optical density response (treated-versus-untreated $OD_{600}$ ratio) after 1 hr is shown. The reader is referred to Table 3 for the serotype definitions of the S. suis strains.

ΔPlySs1 was further tested against a panel of 19 other S. suis strains of diverse serotypes, as well as other species of Gram-positive bacteria. The same lysin concentrations were used as above. For each dosage, the observed lysis values after 1 hr are listed in TABLE 3 and TABLE 4, and the information is summarized graphically in FIG. 21.

TABLE 3

Analysis of Other S. Suis Strains

| Strain | 6.5 µg/ml | 13 µg/ml | 30 µg/ml | 65 µg/ml | 130 µg/ml |
|---|---|---|---|---|---|
| ST13 | 0.32 | 0.17 | 0.04 | 0.02 | 0.02 |
| 6112 (ST1) | 0.14 | 0.11 | 0.06 | 0.02 | 0.01 |
| ST8 | 0.25 | 0.12 | 0.06 | 0.03 | 0.03 |
| 6388 (ST1) | 0.15 | 0.13 | 0.06 | 0.03 | 0.02 |
| 10 (ST2) | 0.29 | 0.18 | 0.10 | 0.05 | 0.02 |
| 8076 (ST9) | 0.52 | 0.40 | 0.21 | 0.14 | 0.04 |
| ST9 | 0.50 | 0.30 | 0.23 | 0.13 | 0.05 |
| ST4 | 0.63 | 0.47 | 0.32 | 0.22 | 0.12 |
| ST11 | 0.64 | 0.47 | 0.32 | 0.19 | 0.07 |
| ST14 | 0.79 | 0.57 | 0.33 | 0.15 | 0.06 |
| ST7 | 0.65 | 0.47 | 0.34 | 0.22 | 0.11 |
| ST1 | 0.80 | 0.34 | 0.36 | 0.19 | 0.06 |
| ST5 | 0.78 | 0.59 | 0.39 | 0.22 | 0.10 |
| 7197 (ST7) | 0.64 | 0.49 | 0.39 | 0.16 | 0.07 |
| ST6 | 0.76 | 0.56 | 0.40 | 0.21 | 0.06 |
| ST3 | 0.81 | 0.71 | 0.48 | 0.32 | 0.16 |
| ST2 | 0.79 | 0.70 | 0.49 | 0.34 | 0.17 |
| ST10 | 0.85 | 0.72 | 0.55 | 0.44 | 0.28 |
| ST12 | See Caption Below** | | | | |

**Various isolates of S. suis were exposed (at optimal buffering conditions) to APlySs1 at the above concentrations. The majority of these bacteria are unnamed clinical isolates of the indicated serotype (e.g. ST1, ST2, etc . . . ). For the named strains, the serotype is given in parentheses. The 1-hour treated/untreated $OD_{600}$-ratio is given for each APlySs1 concentration (representing a single experiment), and the strains are listed in the order of decreasing sensitivity. For strain ST12, it was not possible to conduct OD analysis. Upon the addition of APlySs1 (all above concentrations), the cells would rapidly self-adhere and fall out of suspension. This phenomenon was not observed for untreated ST12-cells.

TABLE 4

Analysis of Other Gram Positive Bacteria

| Strain | 6.5 µg/ml | 13 µg/ml | 30 µg/ml | 65 µg/ml | 130 µg/ml |
|---|---|---|---|---|---|
| S. oralis 35037 | 0.30 | 0.13 | 0.08 | 0.07 | 0.04 |
| S. agalactiae type II | 0.61 | 0.21 | 0.11 | 0.08 | 0.04 |
| S. dysgalactiae 21597 | 0.26 | 0.18 | 0.12 | 0.10 | 0.09 |
| S. pyogenes A486 | 0.12 | 0.13 | 0.13 | 0.11 | 0.10 |
| S. pneumoniae R36 | 0.25 | 0.22 | 0.14 | 0.16 | 0.12 |
| S. dysgalactiae GGS | 0.30 | 0.27 | 0.15 | 0.11 | 0.14 |
| S. equi 700400 | 0.48 | 0.25 | 0.15 | 0.07 | 0.09 |
| S. uberis 27598 | 0.42 | 0.23 | 0.16 | 0.14 | 0.12 |
| S. pyogenes D471 | 0.39 | 0.27 | 0.17 | 0.13 | 0.09 |
| S. gordonii 10558 | 0.76 | 0.32 | 0.19 | 0.09 | 0.06 |
| S. equi 9528 | 0.66 | 0.45 | 0.25 | 0.19 | 0.16 |
| L. monocytogenes HER1084 | 0.63 | 0.52 | 0.26 | 0.14 | 0.04 |
| S. sanguinis 10556 | 0.48 | 0.44 | 0.28 | 0.21 | 0.11 |
| Group E streptococci K131 | 0.69 | 0.50 | 0.33 | 0.22 | 0.15 |
| S. sobrinus 6715 | 0.64 | 0.48 | 0.39 | 0.32 | 0.23 |
| E. faecium EFSK2 | 0.85 | 0.67 | 0.52 | 0.32 | 0.13 |
| S. aureus RN4220 | 0.89 | 0.78 | 0.55 | 0.31 | 0.10 |
| S. salivarius 9222 | 0.80 | 0.76 | 0.56 | 0.53 | 0.37 |
| S. rattus BHT | 0.82 | 0.84 | 0.82 | 0.83 | 0.79 |
| M. luteus 4698 | 0.84 | 0.90 | 0.83 | 0.87 | 0.82 |
| E. faecalis V583 | 0.98 | 0.93 | 0.84 | 0.71 | 0.52 |
| B. cereus 14579 | 0.93 | 0.92 | 0.86 | 0.90 | 0.86 |
| B. thuringiensis HD73 | 0.99 | 0.98 | 0.93 | 0.86 | 0.60 |
| S. mutans U159 | 0.95 | 0.99 | 0.94 | 0.76 | 0.85 |
| S. epidermidis HN1292 | 1.04 | 1.00 | 0.96 | 0.94 | 0.87 |
| S. agalactiae 090R | 0.97 | 0.99 | 0.97 | 0.98 | 0.93 |
| S. simulans TNK3 | 0.96 | 1.00 | 1.00 | 1.00 | 0.96 |
| B. anthracis ΔSterne | 1.02 | 1.03 | 1.02 | 0.98 | 0.90 |
| B. subtilis SL4 | 1.07 | 1.05 | 1.04 | 1.03 | 0.96 |

All S. suis strains demonstrated some degree of susceptibility. Interestingly, many of the non-suis streptococci (and even some nonstreptococci) also lysed at commensurate enzyme concentrations. As demonstrated and depicted in the above results, the PlySs1 lysin enzyme has broad and equivalent activity killing not only against S. suis, but against numerous Streptococcus strains, including Group B streptococci, and additionally against other pathogens, particularly including S. aureus, Enterococcus, Bacillus and Listeria. Classically, a phage lysin demonstrates a marked decrease in activity when going from within its host species to outside of it. Here, however, a broad range of susceptibility was seen among non-suis bacteria, with some demonstrating identical lysis to S. suis itself.

EXAMPLE 3

CFU Killing Assay

Figure 22:
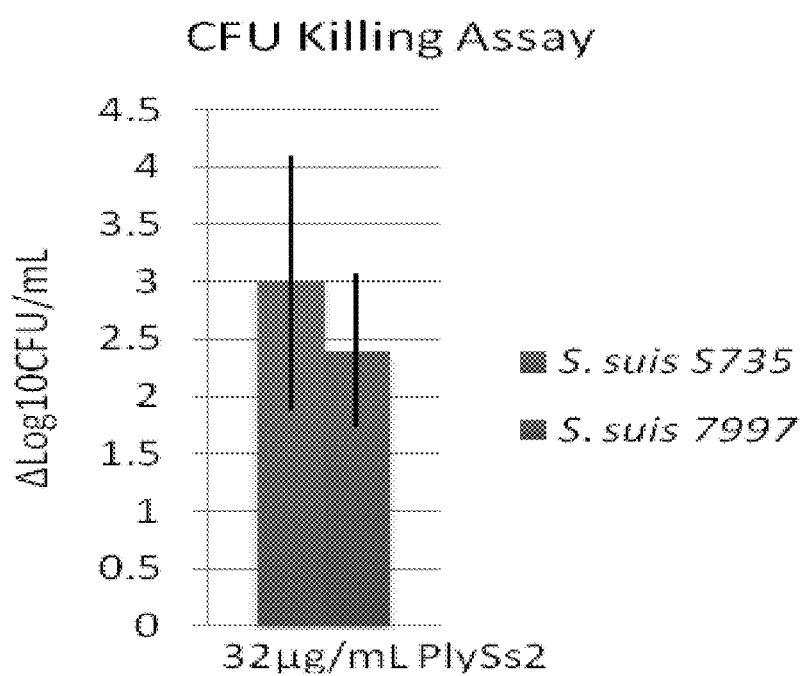
FIG. 22 provides CFU killing assay results of PlySs2 bacteriolytic activity against S. suis strain 7997 and S735.

The specific killing and drop in colony forming units (CFU's) of S. suis S735 and 7997 was determined when exposed to 32 ug/mL PlySs2 for 60 minutes in 15 mM PB, pH 8.0 (FIG. 22).

EXAMPLE 4

Assessment of Resistance

Figure 23:
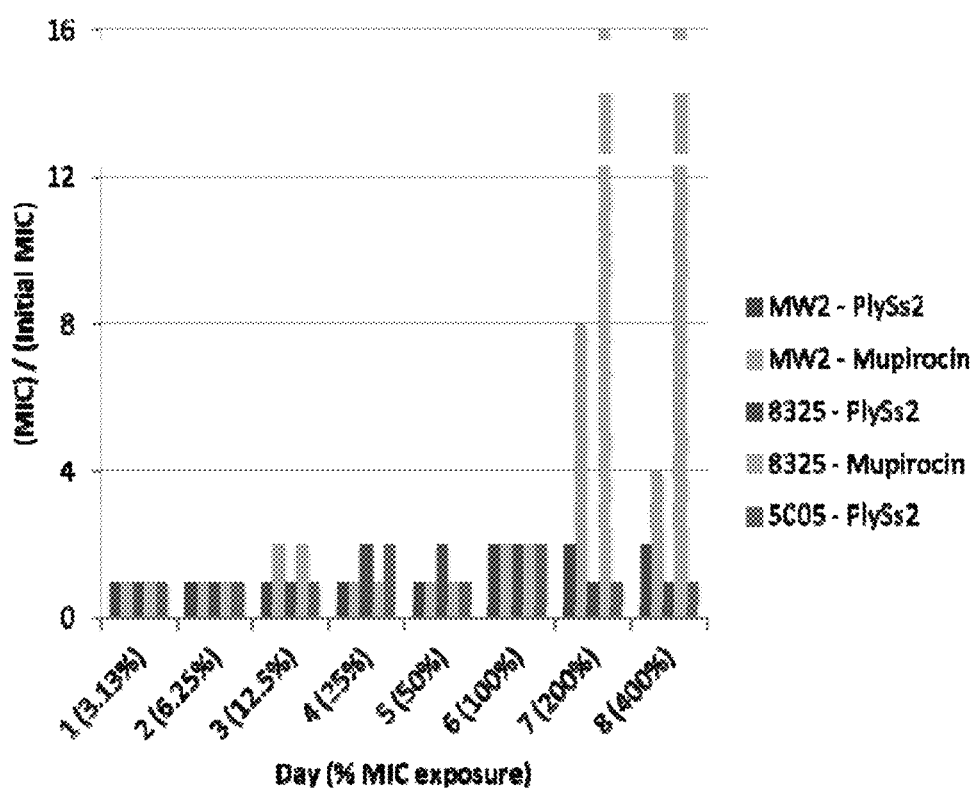
FIG. 23 depicts the results of an S. aureus and S. pyogenes resistance assay against PlySS2 compared to antibiotic mupirocin. None of MRSA strain MW2, MSSA strain 8325, nor S. pyogenes strain 5005 developed resistance against PlySs2 after each was exposed to incrementally increasing concentrations of PlySs2. Both MW2 and 8325 developed resistance to the positive control, mupirocin.
Figure 24:
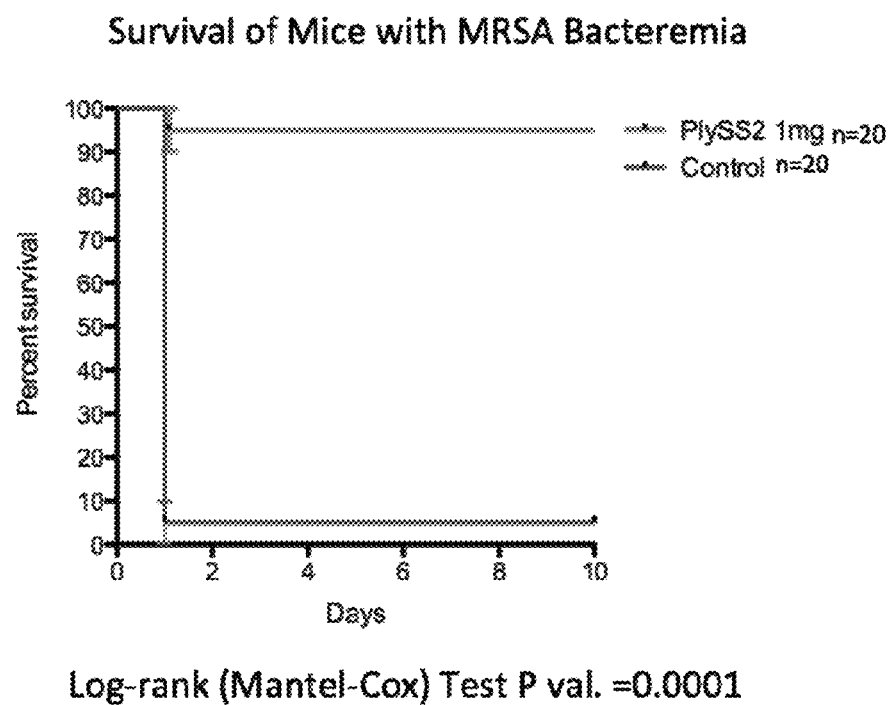
FIG. 24 depicts the survival of mice with MRSA bacteremia over 10 days. PlySs2 cleared bacteremia from 95% of mice tested. Of the controls, just 5% survived.

To test for the development of resistance to the S. suis lysin in susceptible bacteria, each of the Staphylococcal S. aureus strains MW2 and 8325 and Streptococcus pyogenes strain 5005 were exposed to incrementally increasing concentrations of PlySs2. Neither S. aureus strain developed resistance during the course of the study (FIG. 23). Following an established protocol (Rouse, M. S. et al (2005) Antimicrob Agents Chemother 49(8):3187-3191, Pastagia M et al (2011) Antimicrob Agents Chemother 55(2):738-44) for developing mupirocin-resistant strains, S. aureus strains MW2 and 8325 and S. pyogenes 5005 strain were grown in the presence of PlySs2. The concentration of PlySs2 doubled daily from $1/32^{nd}$ of PlySs2's minimally inhibitory concentration (MIC) against each strain to 4× its MIC over an 8-day period. Initially, bacterial cells at 5×10$^8$ CFU/ml were grown overnight in the presence of 1/32×MIC PlySs2 in MHB at 37° C. These cells were centrifuged for 10 min at 900 rcf and divided into two aliquots. One aliquot was diluted 10-fold into fresh MHB media with double the previous concentration of PlySs2; a portion of the other aliquot was spread onto the surface of a MHA plate containing the MIC of PlySs2 to screen for resistant clones. Separate cultures of each strain were grown in the presence of mupiricin in the same manner as a positive control.

In this experiment, the MICs were determined by detection of pellet formation in the bottom of rounded polysterene plate wells. Each day, 1.0 μL sample from each culture was spread on selective plates containing the MIC of the respective drug to which each culture was being exposed. The MIC of PlySs2 or mupirocin was tested for 4 colonies per culture every day by microdilution for each serial passage as described above (Wiegard, I et al (2008) Nat Protoc 3(2): 163-175) to determine if a resistant (defined as a 4-fold increase in MIC) clone had emerged. The procedure was repeated with mupirocin and each strain as a positive control.

EXAMPLE 6

Oral Cavity Microbiota Study

The effects of the *S. suis* lysins on natural bacterial flora were assessed using a rat oral cavity microbiota study. Blood agar plates were streaked with swabs from the oral cavities of two rats. Cultures were isolated from each plate through two cycles of passage and grown overnight in BHI broth. The next day, 1 mL of each culture was plated onto dry BHI agar plates resulting in a lawn of these cultures on agar. After they dried, 10 μL of PlySs2 was deposited on either side of a central 10 μL dd H$_2$O drop as a control. Of 6 cultures, a clearing zone around the PlySs2 drops only appeared on one culture (data not shown). This culture was sent out and confirmed as *S. aureus*. The oral cavities of each of 3 rats from Harlan, 4 Charles River, and 2 separate rats from Charles River were swabbed. Yellow colonies grew on each mannitol salt plate streaked with the swab from each rat indicating that they all orally contained *S. aureus* (data not shown).

EXAMPLE 7

MRSA Mouse Sepsis Model

Figure 25:
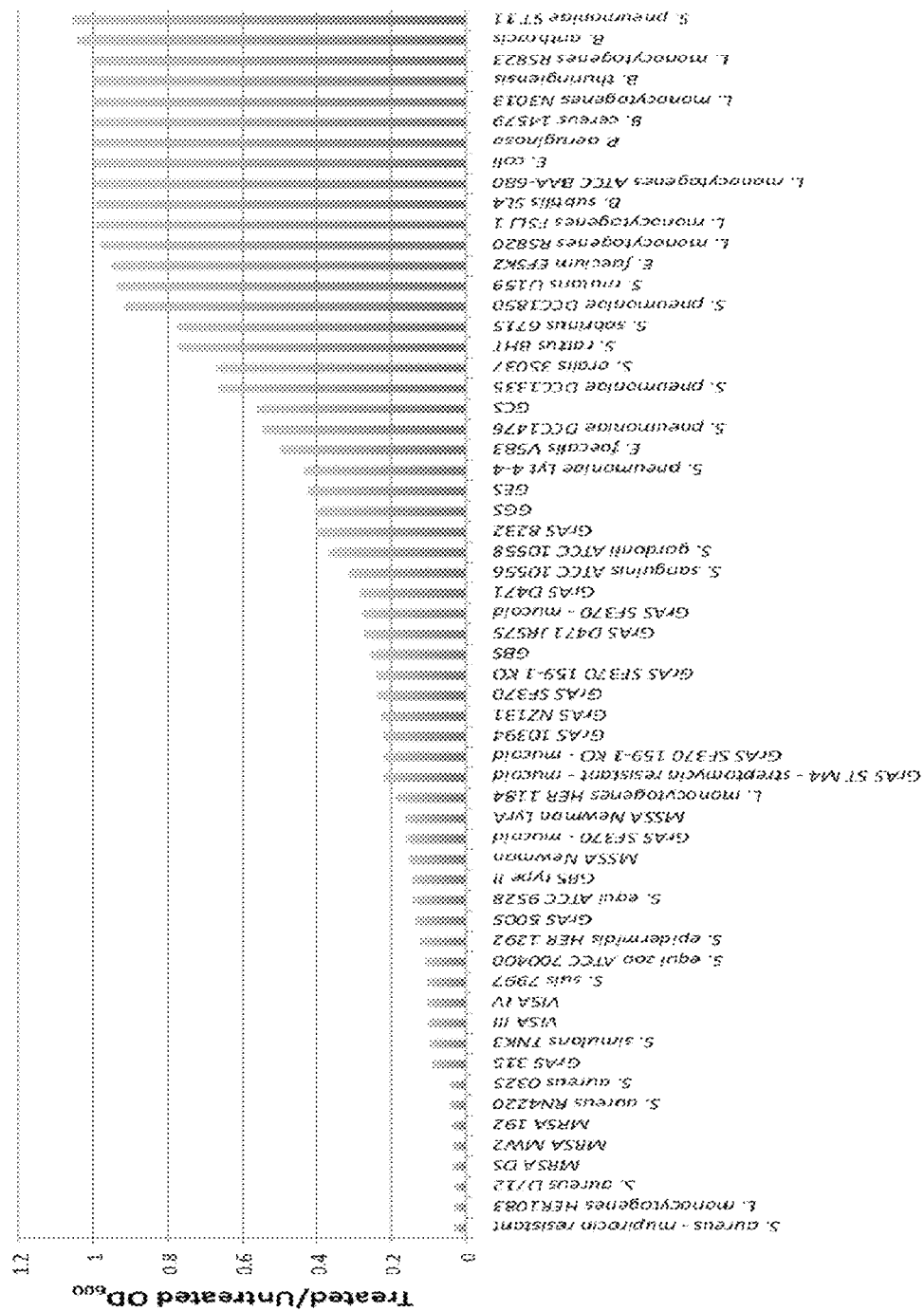
FIG. 25 provides PlySs2 activity against different species and strains. Log-phase cultures were exposed to 32 μg/ml PlySs2 for 60 minutes in phosphate buffer. The final $OD_{600}$ of the treated samples were divided by the final $OD_{600}$ of the untreated samples to generate the normalized values above. Multiple Staphylococci (including, but not limited to: MRSA, MSSA, and VISA), Streptococci, Listeria, Enterococci, and Bacilli were tested for susceptibility to PlySs2 activity. Escherichia and Pseudomonas were tested as Gram-negative controls.

PlySs2 lysin activity against *S. aureus* has been further evaluated in an MRSA mouse sepsis model. In the MRSA mouse sepsis model, susceptible mice (FVB/NJ mice, weight range 15-20 g) were injected with 500 μL of 5×10$^5$ (approx LD$_{100}$) MRSA cells/mL in 5% hog gastric mucin in PBS intraperitoneally (IP). After 3 hours, all of the mice are bacteremic with MRSA in their organs (including spleen, liver, kidney, and heart/blood). To determine PlySs2 activity in this model, 500 μL PlySs2 at 2 mg/mL was injected IP 3 hours after injecting MRSA. This results in ~1 mg/mL PlySs2 within each test mouse's blood stream. Control mice were injected with 500 μL PBS. Survival was evaluated over ten days. The control mice die within 18-20 hours. This study yielded promising results, showing remarkable survival of mice treated with PlySs2 (FIG. 25).

EXAMPLE 8

Wound Infection Model

The *S. suis* lysin was tested in an MRSA wound infection model in rats. In this model, a 3 centimeter incision is created along the dorsal side of the rat. Subsequently, a 1 cm long, 1 cm deep incision is cut into the spinotrapezius muscle. 50 μL of MRSA at 1×10$^8$ CFU's/mL (5×10$^6$ CFU's total) is then inoculated into the wound. After 3-5 minutes, the test rats are treated with 500 μL of PlySs2 at 10 mg/mL. After 3-5 more minutes, the wound is stapled shut and 100 μL of PlySs2 added at 10 mg/mL to the outside of the wound. Care is taken to ensure that none of the bacteria nor the lysin escape the wound as it is sealed off with staples. After 10 days, the CFUs of MRSA are examined within the infections site. In the first 2 rounds of tests PlySs2 was shown to have a deleterious effect on MRSA in the dorsal wounds, with the CFU's of MRSA dropping 3-4 logs in the PlySs2 treated rats compared with the control rats.

Animal Experiments

Animal experiments were initiated by determining the infectious dose of MRSA necessary to cause infection in the rat wound. We found that even at doses up to 10$^9$ CFUs no infection occurred. However, when we added a foreign body (sterile glass beads), infection occurred at <10$^8$ CFUs. Specifically, incisions were made in the backs of the rats (5-6 cm in length) and a 2-3 mm incision was made in the underlying tissue. To this was added 100 mg sterile sand and 50 μl of MRSA. The wounds were stapled closed and the animals followed for 10 days and the wounds opened and examined for gross changes and tissue samples taken for bacteriological examination.

Results

Control animals that received only sterile sand showed normal healing with no unusual characteristics and no bacterial contamination. Animals that received MRSA showed clear abscess formation, necrotic tissue and pus. Samples (weighed and homogenized tissue) taken from the opened wound yielded about 10$^7$ CFU MRSA/gram of tissue. This model was very reproducible yielding the same results in at least 10 animals.

Treatment

We used the model as described above to treat with PlySs2 lysin to determine the effects of the treatment. In this case, half of the animals receiving the MRSA and sand were treated with 10 mg PlySs2 in 50 ul of phosphate buffer (PB), control animals received PB instead 10 minutes after MRSA dosing. The animals were followed for 10 days. At this time the animals were analyzed for gross changes and microbiology. The wounds in control animals exhibit puss, necrosis, and poor healing. This is in sharp contrast to animals treated with a single dose of PlySS2. These wounds did not exhibit pus or necrosis and exhibited better healing.

Results

As can be seen in TABLE 5, the wounds of rats that were treated with buffer alone exhibited an average of 4.27×10$^6$ CFU/gram of tissue of MRSA while animals treated with PlySs2 had an average of 1.41×10$^2$ CFU/gram of tissue, a reduction of >4-logs of MRSA. This number is lower than 4-logs since most of the PlySs2-treated wounds were lower than our detectable limits.

TABLE 5

Rat MRSA Wound Infections After Treatment With PlySS2 or Buffer

| PLYSS2 | CFU/Gram | Buffer | CFU/Gram |
|---|---|---|---|
| P1 | <5.00E+01 | B1 | 1.80E+05 |
| P2 | <5.00E+01 | B2 | 1.18E+06 |
| P3 | 3.20E+02 | B3 | 2.05E+05 |
| P4 | 3.20E+02 | B4 | 7.25E+06 |
| P5 | <5.00E+01 | B5 | 3.20E+05 |
| P6 | <5.00E+01 | B6 | 1.40E+07 |
| P7 | 9.10E+01 | B7 | 5.80E+05 |
| P8 | <5.00E+01 | B8 | 3.00E+05 |
| P9 | 5.00E+01 | B9 | 9.60E+06 |
| P10 | <5.00E+01 | B10 | 4.40E+06 |
| P11 | <5.00E+01 | B11 | 2.94E+06 |
| P12 | 8.40E+02 | B12 | 4.81E+06 |
| P13 | <5.00E+01 | B13 | 5.83E+06 |
| P14 | <5.00E+01 | B14 | 2.82E+06 |
| P15 | <5.00E+01 | B15 | 9.63E+06 |
| AVG* | 1.41E+02 | AVG | 4.27E+06 |

CFU Reduction vs Control 3.02E+04
< = CFU below level of detection
No Growth on Plates
*Not true Avg since < actual #

EXAMPLE 19

In Vivo Nasal Decolonization of MRSA

Carriage of both MSSA and MRSA in the human anterior nares is the major reservoir for *S. aureus* infection. Studies have shown that roughly 80% of the population could be nasally colonized by *S. aureus*, and that colonization can be an increased risk factor for developing other more serious *S. aureus* infections (Kluytmans, J., A. van Belkum (1997) Clin Microbiol Rev 10(3):505-520). In fact, assessment of nasal colonization is being instituted on admission to critical care settings in hospitals in the U.S. Elimination of nasal carriage in the community or in the hospital setting thus could possibly reduce the risk of infection and slow the spread of drug resistant *S. aureus*. To study the ability of *S. suis* lysin to reduce MRSA colonization of the nasal mucosa, C57BL/6J mice are intranasally inoculated with ~2×10$^7$ of a spontaneously streptomycin resistant strain of MRSA (191-SMR). Twenty-four hours post-infection mice are administered three doses (1 mg) hourly of either phosphate buffered saline (control), or PlySs lysin into the nasal passages. One hour after the last treatment, mice are sacrificed and bacteria colonies enumerated on Spectra MRSA agar (a selective chromogenic medium developed to diagnostically detect MRSA nasal colonization) and Columbia blood agar. Three independent experiments are performed to evaluate at least 10 mice for each treatment group. Significantly reduction in the mean CFU on the nasal mucosa on treatment with *S. suis* lysin is determined.

REFERENCES

1. Beres, S. B., J. M. Musser. *Contribution of Exogenous Genetic Elements to the Group A Streptococcus Metagenome*. PLoS ONE, 2007. 2(8):1-14.
2. Cantin, M., J. Harel, R. Higgins, M. Gottschalk. *Antimicrobial resistance patterns and plasmid profiles of Streptococcus suis isolates*. Journal of Veterinary Diagnostic Investigation, 1992. 4:170-174.
3. Fischetti, V. A. *Bacteriophage lysins as effective antibacterials*. Current Opinion in Microbiology, 2008. 11:393-400.
4. Nelson, D., L. Loomis, V. A. Fischetti. *Prevention and elimination of upper respiratory colonization of mice by group A streptococci by using a bacteriophage lytic enzyme*. Proceedings of the National Academy of Sciences of the United States of America, 2001. 98:4107-4112.
5. Sriskandan, S., J. D. Slater, *Invasive Disease and Toxic Shock due to Zoonotic Streptococcus suis: An Emerging Infection in the East?* PLoS Medicine, 2006. 3(5):585-587.
6. Wang, I. N., D. L. Smith, R. Young, *Holins: the protein clocks of bacteriophage infections*. Annual Review of Microbiology, 2000. 54:799-825.

EXAMPLE 20

Bacteriophage Lysin PlySs2 with Broad Lytic Activity Protects Against Mixed Methicillin-Resistant *Staphyloccocus aureus* and *Streptococcus pyogenes* Infection Methicillin-resistant *Staphylococcus aureus* (MRSA) and *Streptococcus pyogenes* (group A streptococci—GrAS) cause several infectious human diseases. These bacterial pathogens are among the many Gram-positive pathogens that have established resistance to leading antibiotics. There is a need for alternative therapies to combat these infectious agents. We have developed a novel bacteriophage (phage) lysin with activity against MRSA, vancomycin-intermediate *S. aureus*, *Streptococcus suis*, *Listeria*, *Staphylococcus simulans*, *Staphylococcus epidermidis*, *Streptococcus equi*, *Streptococcus agalactiae*, *S. pyogenes*, *Streptococcus sanguinis*, group G streptococci, group E streptococci, and *S. pneumoniae*. This phage lysin from *S. suis* was termed PlySs2. Consistent with previous exogenous lysins, PlySs2 did not display activity against any Gram-negative bacteria (eg. *Escherichia*, *Bacillus*, or *Pseudomonas*). PlySs2 has an N-terminal cysteine histidine aminopeptidase (CHAP) domain, and a C-terminal SH3b binding domain. PlySs2 is stable at 50° C. for 30 min, 37° C. for 24 hours, 4° C. for 15 days, and −80° C. for >8 months. It maintains full activity after 10 freeze-thaws. At 128 µg/ml, PlySs2 was able to reduce colony forming units (CFUs) of MRSA and *S. pyogenes* by 5-logs and 3-logs, respectively. The minimum inhibitory concentration (MIC) of PlySs2 was 16 µg/ml for MRSA. A single 2 mg dose of PlySs2 protected 22 of 24 mice in a mouse septicemia model of a mixed MRSA and *S. pyogenes* infection. After serially increasing exposure to PlySs2, neither MRSA nor *S. pyogenes* established resistance to PlySs2 as MRSA did to mupirocin. No lysin has shown such effective broad lytic activity; stability; and efficacy against leading human bacterial pathogens. PlySs2 is a promising therapeutic for MRSA, *S. pyogenes*, and many other pathogens without incidence of resistance.

There are many Gram-positive pathogens causing disease and infection worldwide, including: *S. pyogenes*, *S. aureus*, *S. agalactiae*, *Listeria*, and others. They cause a variety of diseases, and there are limits to current treatments.

Over 30% of the human population may be colonized with *Streptococcus pyogenes* in the upper respiratory tract—the only known site of benign colonization [1]. Colonized individuals are much less likely than severely sick persons to transmit illness [1]. *S. pyogenes* (group A streptococci—GrAS), annually infects over 750 million people [2-4]. Each year, there is a 25% mortality rate among the 650,000 cases that progress to severe infection [2]. *S. pyogenes* causes pharyngitis in the upper respiratory tract, and impetigo within the skin of human hosts [5]. Scarlet fever, erysipelas, cellulitis, necrotizing fasciitis, and toxic-shock syndrome and other illnesses that emerge from *S. pyogenes* infection. The mortality rates can be very high for these infections, including 20% for necrotizing fasciitis, and 50% for toxic-shock syndrome [6]. Rheumatic fever, acute glomerulonephritis, and forms of obsessive-compulsive disorder are non-suppurative sequelae associated with a *S. pyogenes* [7]. Rheumatic fever outbreaks have seen a rise worldwide since the 1980's [8]. Though rare, rheumatic fever can progress to severe illness if it enters deep into soft tissue [4].

Of all the Gram-positive pathogens, *Staphylococcus aureus* has become the most difficult to treat. *S. aureus* is a Gram-positive facultative anaerobe that causes most *Staphylococcus* infections in man. Human anterior nares (nostrils) are typically the primary sites of *S. aureus* colonization, along with other moist openings on the body serving as additional sites for entry [9-12]. *S. aureus* often causes severe secondary infections in immunocompromised individuals, as well as causing disease in otherwise healthy individuals. In addition to skin and soft tissue infections (SSTIs), it can cause sepsis, toxic shock syndrome, and necrotizing pneumonia, necrotizing fasciitis, and pyomyositis, endocarditis, and impetigo. These infections are usually treated with methicillin, mupirocin, or vancomycin.

Many *S. aureus* strains, such as methicillin-resistant *S. aureus* (MRSA) and vancomycin-resistant *S. aureus* (VRSA), have evolved resistance to one or more antibiotics used as standard treatment [13], making them even more difficult to treat with available antimicrobials [13]. The causative pathogen for numerous nosocomial infections, MRSA accounts for more than 50% of *S. aureus* hospital isolates causing pneumonia and septicemia [14]. Further exacerbating the problem, MRSA is readily transmitted between patients in hospitals [15]. Nearly half of all bacteremia cases in intensive care units are caused by MRSA having a mortality rate of 30-40% [16, 17]. It is the primary cause of lower respiratory tract infections, surgical site infections, and 19,000 deaths/year in the US alone [14, 18].

While health-care-associated MRSA infects susceptible patients, community-associated MRSA (CA-MRSA) infections arise in healthy individuals [19, 20]. CA-MRSA strains seem to be more virulent and contagious than traditional MRSA strains m humans and animal models, causing more severe diseases [21-24]. Distinct strains of CA-MRSA are epidemic in Europe, North America, Oceania, and other regions [20, 25, 26]. The MW2 strain (pulsed-field type USA400) is the prototypical CA-MRSA, having contributed to the incipient outbreak of CA-MRSA in the USA, thus leading to an epidemic [19, 27].

A beta-hemolytic Gram-positive *streptococcus*, *Streptococcus agalactiae* (Group B streptococci—GBS) contains an antiphagocytic capsule as its primary virulence factor [28, 29]. *S. agalactiae* can exist in the human gastrointestinal system, occasionally colonizing secondary sites like the vagina in over 33% of women [30, 31]. The colonizing *S. agalactiae* can infect a neonate during birth resulting in bacterial septicemia, making early-onset *S. agalactiae* the primary cause of death in newborns for over 4 decades [32-34],[35]. The current standard of practice exposes the mother to antibiotics that further the likelihood of resistance.

A recent Gram-positive pathogen outbreak involves *Listeria*, and has killed 29 in the United States as from July to November 2011—the most deadly food-borne illness outbreak in the US since the 1970's [36]. Most individuals contract listeriosis after consumption of contaminated food, facing a mortality rate of 20-30%, even with antibiotic therapy [37, 38]. *Listeria* survives well in food processing systems and the human gastrointestinal tract, readily adjusting to swift changes in pH, salinity, and temperature [37, 39, 40].

There are many other Gram-positive human pathogens, including: *Streptococcus sanguinis* (dental plaque and caries); *S. sanguinis* (endocarditis); Group G *Streptococcus*; Group E *Streptococcus*; and *S. pneumococcus* (pneumonia, otitis media, meningitis, bacteremia, sepsis, endocarditis, peritonitis, and cellulitis).

Zoonotic Gram-positive pathogens include: *Streptococcus equi* (strangles—an upper respiratory tract infection—in equines, eg. horses); and *Streptococcus suis* (sepsis and meningitis in pigs and humans). The pathogenic *S. suis* serotype 9 strain 7997 has been associated with increasing reports of zoonotic transmission from pigs to humans [41]. Humans and pigs have been treated with penicillin or gentamicin, but *S. suis* isolates resistant to these antibiotics exist [42]. *S. suis* may develop a consistent presence in human populations in years to come.

There has been a sharp increase in antibiotic resistance among all of these Gram-positive microbes. Therefore, alternative therapies must be developed to treat bacterial pathogens. Novel antimicrobial sources include enzyme-based antibiotics ("enzybiotics") such as phage lytic enzymes (also known as endolysins or "lysins").

Lysins have garnered much attention recently as novel antibacterial agents (reviewed in [18, 43, 44]). After bacteriophage viruses replicate inside of a host, their progeny must escape. Phage encode both holins that open a pore in the bacterial membrane, and peptidoglycan hydrolases called lysins that break bonds in the bacterial wall [45]. Since Gram-positive bacteria are hypotonic to their surroundings, disruption of the cell wall leads to osmotic lysis of the bacteria and release of viral progeny [18]. These peptidoglycan hydrolases (catalyzing a variety of specific bonds) are encoded by virtually all double-stranded DNA phages.

Lysins can be cloned from viral prophage sequences within bacterial genomes, recombinantly expressed in *Escherichia coli*, purified, and used for treatment [46]. When applied exogenously, these proteins are able to access the bonds of a Gram-positive bacterium's cell wall, as the peptidoglycan of these species is continuous with the extracellular space [18]. Lysins kill bacteria quicker than any known non-chemical agent biological compounds [47-49].

Lysins have been shown to demonstrate a high lethal activity against numerous Gram-positive pathogens—generally, species that the encoding phage infects or closely-related organisms [18, 47]. Having been proposed as potential enzybiotic agents, lysins are notable for the potency and specificity they demonstrate toward particular bacteria [47, 48, 50, 51]. As such, they should have a less dramatic affect on the normal nonpathogenic flora in the host than broader-acting antibiotics [18]. To date, no lysin has shown broad in vivo activity against multiple species of bacterial pathogens.

Lysins have been developed against MRSA, including ClyS (a staphylococcal-specific chimeric lysin previously developed in our lab) [50]. Lysins have been evolved by viruses in an evolutionary struggle to infect bacteria for billions of years. Therefore, there is selective pressure for them to chose a feature that is essential to normal bacterial function—and thus, unlikely to be altered.

Two phages infecting *S. suis* have been previously isolated and studied. Harel et al. induced a siphoviral prophage from the genome of a serotype 2 strain 89-999, although the identity of its lysin remains undetermined [52]. More recently, Ma and Lu isolated a lytic phage from nasal swabs of healthy pigs, sequencing its 36 kb genome [53]. This phage, termed SMP, demonstrated a limited host range, infecting only 2/24 *S. suis* strains within serotype 2. The same group later PCR-cloned and recombinantly expressed the SMP lysin (LySMP); the enzyme demonstrated bacteriolytic activity in vitro against several *S. siuis* serotypes. LySMP, as a recombinant protein, did not fold properly by itself and was only active in the presence of reducing agents, which may limit its potential for in vivo trials [54].

There are over 11 completed *S. suis* genomes in the NCBI database. The sequences of *S. suis* strains were analyzed to identify candidate potential phage lysins within prophage regions and a new phage lysin from *S. suis* (termed PlySs2) was ultimately identified, isolated, cloned and characterized (see above Examples). Additional characterization is now provided including the acute activity of PlySs2 against MRSA and *S. pyogenes*.

Materials and Methods

Bacterial Strains.

All strains were stored at −80° C. (TABLE 6). *Staphylococcus, Streptococcus, Listeria, Enterococcus, Pseudomonas, Bacillus* spp. strains were cultivated m brain heart infusion (BHI) medium. *Escherichia coli* was grown in Luria Bertain (LB) medium. All media were acquired from Becton, Dickinson, and Company (Sparks, Md.), unless otherwise stated. Bacteria were maintained at 37° C. Overnight cultures were grown at 37° C., and shaken at 200 rpm, if necessary.

TABLE 6

Listing of Strains

| Organism | Serotype | Strain | ATCC | Source[a] | Notes |
|---|---|---|---|---|---|
| Group E Streptococcus | 2 | K131 | 123191 | 1 | |
| Streptococcus suis | 9 | 7997 | | 6 | |
| Streptococcus sobrinus | | 6715 | | 1 | |
| Streptococcus sanguinis | | | 10556 | 1 | |
| Streptococcus rattus | | BHT | | 1 | |
| Streptococcus pyogenes | M6 | D471 | | 1 | |
| Streptococcus pyogenes | MΔ | D471 | | 1 | mutant JRS75 |
| Streptococcus pyogenes | M6 | 10394 | | 1 | |
| Streptococcus pyogenes | M49 | NZ131 | | 1 | |
| Streptococcus pyogenes | M4 | | | 1 | streptomycin resistant - mucoid |
| Streptococcus pyogenes | M3 | 315 | | 1 | |
| Streptococcus pyogenes | M18 | 8232 | | 1 | |
| Streptococcus pyogenes | M1 | SF370 | | 1 | phage 159-1 KO - mucoid |
| Streptococcus pyogenes | M1 | SF370 | | 1 | phage 159-1 KO |
| Streptococcus pyogenes | M1 | SF370 | | 1 | mucoid |
| Streptococcus pyogenes | M1 | SF370 | | 1 | mucoid |
| Streptococcus pyogenes | M1 | SF370 | | 1 | |
| Streptococcus pyogenes | M1 | 5005 | | 1 | |
| Streptococcus pneumoniae | 9V | DCC1335 | | 1 | |
| Streptococcus pneumoniae | 6 | DCC1850 | | 1 | |
| Streptococcus pneumoniae | 15 | DCC1476 | | 1 | |
| Streptococcus pneumoniae | 11 | | | 1 | |
| Streptococcus pneumoniae | | | | 1 | mutant Lyt 4-4 |
| Streptococcus oralis | | 35037 | | 1 | |
| Streptococcus mutans | | U159 | | 1 | |
| Streptococcus gordonii | | | 10558 | 1 | |
| Streptococcus equi | | | 9528 | 1 | |
| Streptococcus equi zoo | | | 700400 | 1 | |
| Streptococcus dysgalactiae | | | | 1 | Group G Streptococcus |
| Streptococcus dysgalactiae equisimilis | | 26RP66 | | 1 | Group C Streptococcus |

TABLE 6-continued

Listing of Strains

| Organism | Serotype | Strain | ATCC | Source[a] | Notes |
|---|---|---|---|---|---|
| Streptococcus agalactiae | Type II | | | 1 | Group B Streptococcus |
| Streptococcus agalactiae | | 090R | | 1 | Group B Streptococcus |
| Staphylococcus simulans | | | | 2 | TNK3 |
| Staphylococcus epidermidis | | HER 1292 | | 3 | |
| Staphylococcus aureus | | | | 4 | vancomycin intermediate resistance IV |
| Staphylococcus aureus | | | | 4 | vancomycin intermediate resistance III |
| Staphylococcus aureus | | RN4220 | | 1 | |
| Staphylococcus aureus | | Newman | | 2 | methicillin sensitive - mutant LyrA |
| Staphylococcus aureus | | Newman | | 2 | methicillin sensitive |
| Staphylococcus aureus | | MW2 | | 5 | methicillin resistant - community acquired |
| Staphylococcus aureus | | 192 | | 1 | methicillin resistant |
| Staphylococcus aureus | | | | 1 | methicillin resistant from patient DS |
| Staphylococcus aureus | | | | 1 | highly mupirocin resistant |
| Staphylococcus aureus | | | | 1 | D712 - daptomycin resistant |
| Staphylococcus aureus | | | | 1 | 0325 - daptomycin resisitant |
| Pseudomonas aeruginosa | | RS1 | | 1 | |
| Listeria monocytogenes | | HER 1184 | | 1 | |
| Listeria monocytogenes | 4b | N3013 | | 1 | |
| Listeria monocytogenes | 3b | FSLJ 1 | | 1 | |
| Listeria monocytogenes | | | | 1 | RS823 |
| Listeria monocytogenes | | | | 1 | RS820 |
| Listeria monocytogenes | | HER1083 | | 1 | |
| Listeria monocytogenes | | | BAA-680 | 1 | |
| Escherichia coli | | Top 10 | | 1 | |
| Enterococcus faecium | | | | 1 | EFSK-2 |
| Enterococcus faecalis | | V583 | | 1 | |
| Bacillus thuringiensis | | HD-73 | | 1 | |
| Bacillus subtilis | | SL4 | | 1 | |
| Bacillus cereus | | 14579 | | 1 | |
| Bacillus anthracis | | Δ sterne | | 1 | |

[a]1, The Rockefeller University Collection; 2, Olaf Schneewind, University of Chicago, Chicago, IL; 3, Barry Kreiswirth, Public Health Research Institute, New Jersey; 4, Alexander Tomasz, The Rockefeller University; 5, ATCC; 6, Jaap A. Wagenaar, Utrecht University, Utrecht, Netherlands.

CFU Studies.

Log-phase bacteria were resuspended in buffer A to an $OD_{600}$ of 0.1 (=0.5 McFarland≈$10^8$ CFU/ml). PlySs2 was added at 128 μg/ml to polypropylene microtiter plates (Costar) in triplicate for each test organism. Plates were sealed and incubated at 37° C. with shaking every 5 minutes for 1 hour. After 1 hour of incubation, cells were serially diluted in 10-fold increments and plated on BHI. Triplicate controls for each strain were performed with buffer B replacing PlySs2.

MIC Studies.

The Wiegand, et al. protocol to determine minimum inhibitory concentrations was followed with adjustments detailed below [57]. A final suspension of ≈$5×10^5$ cells/ml in MHB (or BHI for S. pyogenes) resulted after Sterile-filtered lysin or vehicle was added at the appropriate concentration [57]. These tests were distributed within a 96-well microtiter plate. The MIC's were determined, in this experiment, by detection of pellet formation in the bottom of rounded polysterene plate wells. They were also corroborated colorimetrically with alamarBlue®.

In Vivo Murine Model.

The Rockefeller University's Institutional Animal Care and Use Committee approved all in vivo protocols. A systemic infection model described in Daniel, A. et al., was used to test for the in vivo efficacy of PlySs2 against multiple gram-positive bacteria [50]. Briefly, 4-5 week old female FVB/NJ mice (weight range 15 to 20 g) were obtained from The Jackson Laboratory (Bar Harbor, Me.). After a period of acclimation, mice were injected intraperitoneally (IP) with 0.5 ml of mid log-phase ($OD_{600}$ 0.5) bacteria diluted with 5% hog gastric mucin (Sigma) in saline. Bacterial suspensions contained ~$5 \times 10^5$ CFU/ml of MW2, a PVL toxin-encoding MRSA strain, ~$1 \times 10^7$ of MGAS5005, an M1 serotype of *Streptococcus pyogenes* that is virulent in humans and mice (Musser), or a combination of both bacteria simultaneously at the above concentrations for the mix infection experiments. Actual bacterial inoculation titers were calculated by serial dilution and plating to Columbia blood agar plates for each experiment. Mice became bacteremic within one to three hours and contained MRSA and/or *S. pyogenes* in their organs (including spleen, liver, kidney, and heart/blood) ([50], and unpublished observations). Three hours post-infection the animals were divided into 4 to 5 treatment groups and were intraperitoneally administered 0.5 ml of either 20 mM phosphate buffer, 2 mg/ml of the streptococcal lysin PlyC [59], 2 mg/ml of ClyS [50], 2-4 mg/ml PlySs2, or a combination of 2 mg/ml PlyC and 2 mg/ml of ClyS. The survival rate for each experimental group was monitored every 12 hours for the first 24 hours then every 24 hours up to 10 days post-infection. The data were statistically analyzed by Kaplan Meier Survival curves and a Logrank test performed for 95% confidence intervals using the Prism computer program (GraphPad Software; La Jolla, Calif.).

Results

Broad Lytic Activity of PlySs2.

All tested strains of *S. aureus* were highly susceptible to PlySs2 lysis (FIG. 25). This includes strains resistant to methicillin, vancomycin, daptomycin, mupirocin, and lysostaphin. PlySs2 activity against vancomycin-intermediate *S. aureus* (VISA) and Newman strains was less severe than against other strains, but nevertheless robust. In addition to *aureus*, other *Staphylococcus* species (*epidermidis* and *simulans*) were sensitive as well. PlySs2 exhibited conventional activity against its native species, *S. suis*. Two strains of *Listeria* exhibited significant lysis from PlySs2, but other *Listeria* strains were impervious to PlySs2 treatment. To a lesser extent, PlySs2 had activity against *S. equi zoo, S. equi, S. agalactiae* Type II (encapsulated), and *S. agalactiae* 090R. Of note, PlySs2 also had activity against all strains of *S. pyogenes*. This included serotypes M1, M3, M4, M6, M18, M49, and a variant without M protein. Unencapsulated, capsulated, and mucoid strains *S. pyogenes* all displayed comparable susceptibility to PlySs2.

There were a number of species that displayed less lysis than those above. They were *Streptococcus sanguinis*, group G *Streptococcus*, group E *Streptococcus, Enterococcus faecalis*, and one strain of *S. pneumococcus*. *S. gordonii* was the only commensal against which PlySs2 had substantial activity. The outer membrane surrounding the Gram-negative peptidoglycan prevented PlySs2 from displaying activity against *Escherichia, Bacillus*, or *Pseudomonas*, as expected.

The activity of PlySs2 was compared to that of ClyS in a simultaneous, side-by-side test using the same batch of cells (data not shown). The activity of each was comparable, but PlySs2 is far more tractable; we continued to pursue PlySs2 as a therapeutic against MRSA. Classically, a phage lysin demonstrates a marked decrease in activity against specimens outside of its host species. Here, however, a broad range of susceptibility was seen among non-*S. suis* bacteria, with some demonstrating more sensitivity than *S. suis*.

Efficacy of PlySs2 Against Gram-Positive Pathogens.

Figure 26:
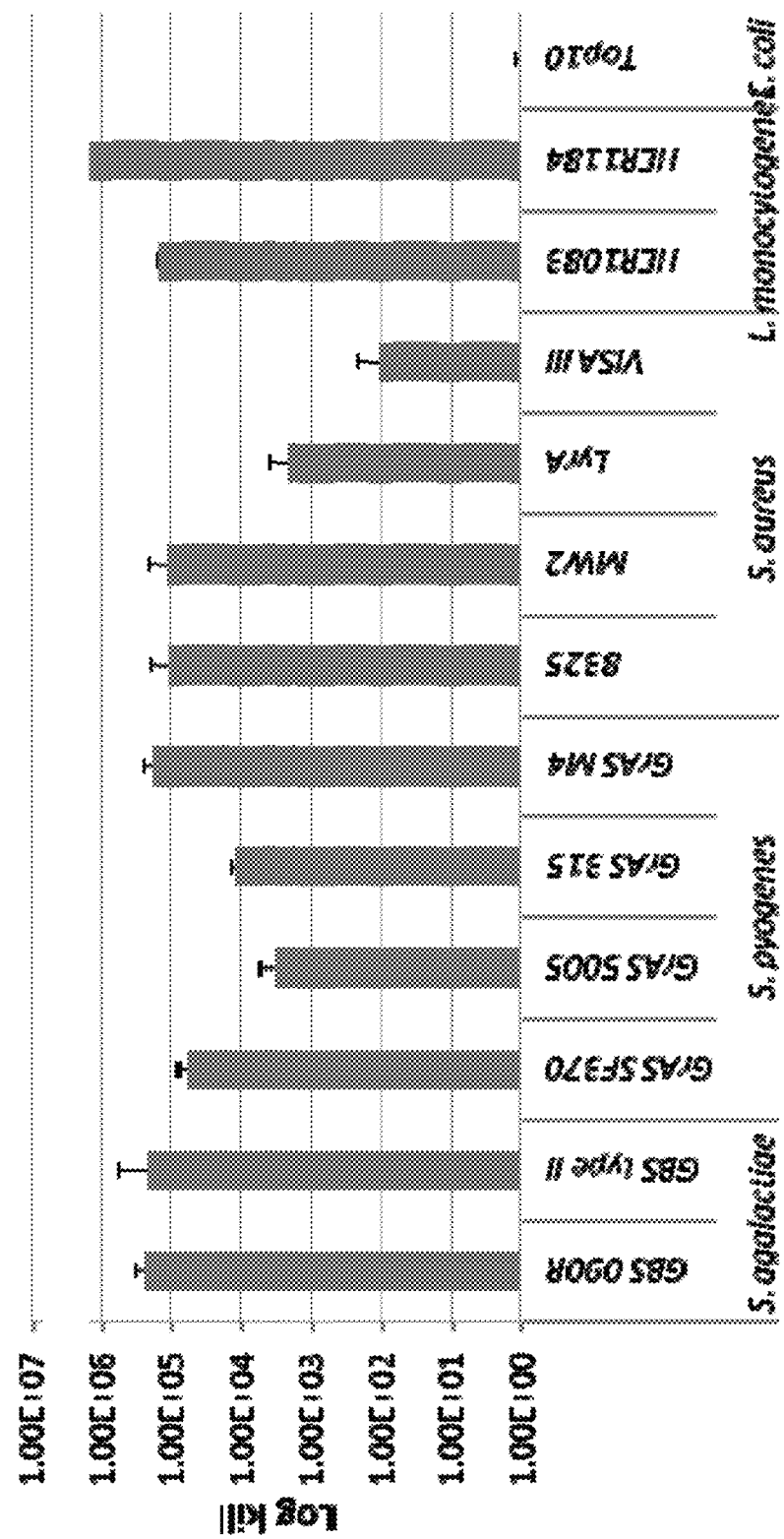
FIG. 26 depicts bactericidal effect of PlySs2 on various strains. Bactericidal effect of 128 μg/ml PlySs2 60 mins post-treatment. The reduction in CFU counts is presented along a logarithmic scale. Characteristically, PlySs2 had significant activity against MRSA MW2. Of note, PlySs2 dramatically reduced S. agalactiae and L. monocytogenes. There was no reduction in number of the negative control E. coli.

PlySs2 displayed significant activity reducing the number of *L. monocytogenes, S. agalactiae, S. aureus*, and *S. pyogenes* (FIG. 26). It reduced all tested strains of *S. agalactiae* and *L. monocytogenes* more than *S. pyogenes* 5005. The negative control *E. coli* was not reduced in number after PlySs2 treatment.

MIC of PlySs2 for Pathogens.

The MIC of PlySs2 was relatively low for *L. monocytogenes* and *S. aureus* (FIG. 27). *S. pyogenes* and *S. agalactiae* registered similar MICs of PlySs2. The MIC for the negative control *E. coli* was too high to calculate.

Murine Mixed MRSA and *S. pyogenes* Septicemia Model.

To determine if the broad lytic activity of PlySs2 could provide in vivo protection from infection with gram-positive pathogens, either alone or as a mixed infection, FVB/NJ mice were intraperitoneally injected with ~$5 \times 10^5$ CFU of MRSA strain MW2, ~$1 \times 10^7$ of *S. pyogenes* strain MGAS5005 and/or both bacteria simultaneously at the concentrations above. Three hours later mice were divided into 5 treatment groups and injected IP with either 20 mM phosphate buffer, 1 mg of the control staphylococcal lysin; ClyS, 1 mg of control streptococcal lysin; PlyC, 1 mg of ClyS+1 mg of PlyC, or PlySs2 (1 mg for MRSA infections or 2 mg for streptococcal and mixed infections, respectively). Mice were then monitored for survival over ten days. The results from 4 independent experiments were combined and mouse survival data plotted with a Kaplan Meier Survival curve (FIG. 28).

Figure 28A:
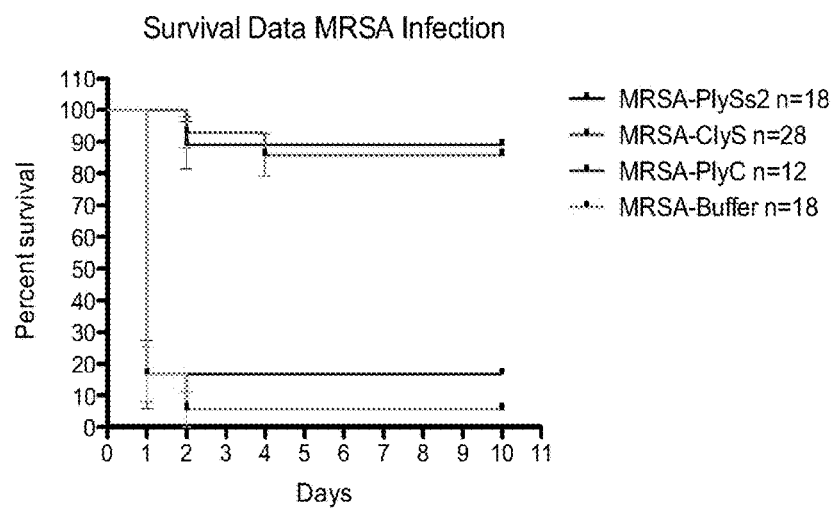
FIG. 28 shows PlySs2 protected mice from death caused by mixed MRSA and *S. pyogenes* infection. FVB/NJ mice were intraperitoneally injected with 5% mucin containing ~5×10$^5$ CFU of MRSA strain MW2, ~1×10$^7$ *S. pyogenes* strain 5005, or combination of both bacteria (mixed infection) from the above inoculums at the same concentrations. Three hours post-infection, mice in all infection groups (A-C), received one intraperitoneal injection of 20 mM phosphate buffer control, 1 mg of ClyS, 1 mg of PlyC, or a combination of 1 mg of ClyS plus 1 mg of PlyC for the mixed infection. PlySs2 treatments consisted of 1 mg for MRSA infections (A), or 2 mg for *S. pyogenes* and mixed infections (B-C). Mice were monitored for survival over ten days. The results from four independent experiments were combined and the mice survival data plotted with a Kaplan Meier Survival curve.

Within twenty-four hours of MRSA infection alone 17/18 buffer control mice and 10/12 PlyC streptococcal lysin treated mice died of bacterial sepsis throughout their organs (including spleen, liver, kidney, and heart/blood). Only 2/18 of PlySs2 treated mice died at forty-eight hours, the remaining PlySs2 treated mice survived over the 10-day course of the experiments with mice results comparable to the staphylococcal specific lysin: ClyS (24/28, 86%) versus PlySs2 (16/18, 88%) (FIG. 28A).

Figure 28B:
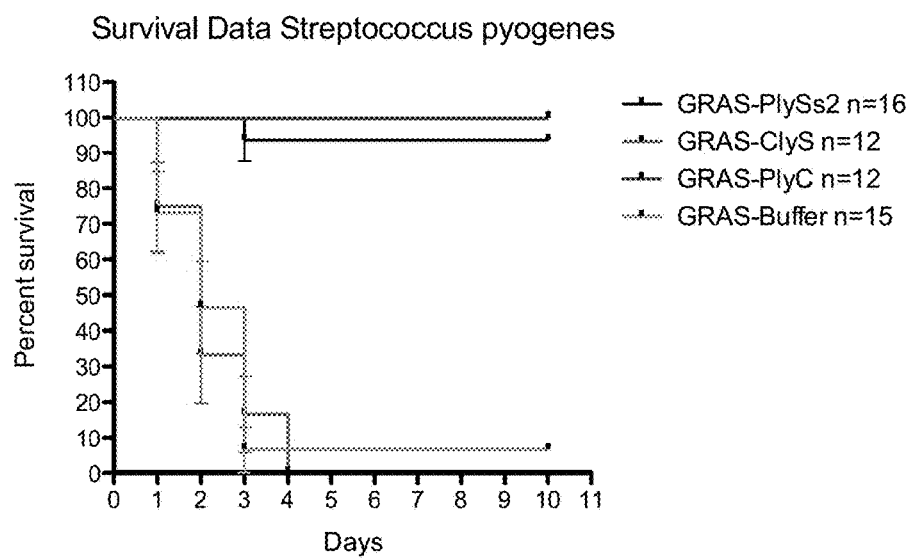
Figure 28C:
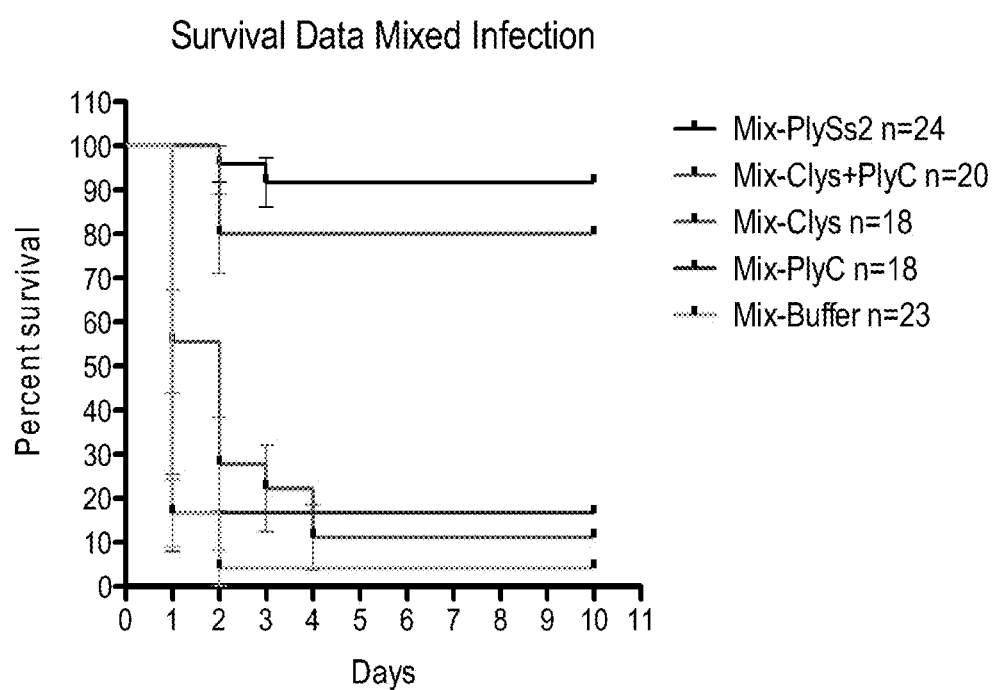

Mice infected with *S. pyogenes* alone tended to succumb at a slower rate, 14/15 buffer treated mice and 12/12 Clys staphylococcal specific lysin treated mice were dead by day three and four, respectively. On the contrary, only 1/16 PlySs2 mice died at day three, the rest survived (15/16, 94%) to give results comparable to the streptococcal specific lysin PlyC (12/12, 100%) (FIG. 28B). To simulate a mixed bacterial infection, mice were injected IP with a mixture of both MRSA and *S. pyogenes* from the bacterial inoculums' above. Treatment with buffer or the single specific lysin controls did not significantly prolong mouse survival. A majority of the PlyC (15/18) and buffer (21/23) treated mice died within 24 and 48 hours, respectively (FIG. 28C). While the mix infection animals treated with ClyS succumbed slower, with 14/16 dead by day 4, similar to mice infected with only *S. pyogenes*. In contrast to the controls most of the PlySs2 treated mice survive the mixed infection (22/24, 92%) and was comparable if not better to the mice treated with both Clys+PlyC at the same time (16/20, 80%) (FIG. 28C).

PlySs2 Demonstrates Rapid Kill Versus Antibiotics in MRSA Strains

Figure 29:
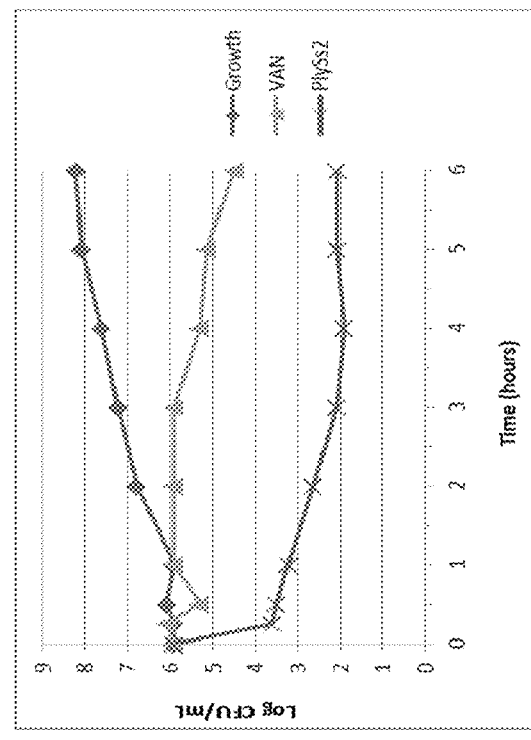
FIG. 29 depicts activity of PlySs2 and vancomycin against MRSA isolates.
Figure 29:
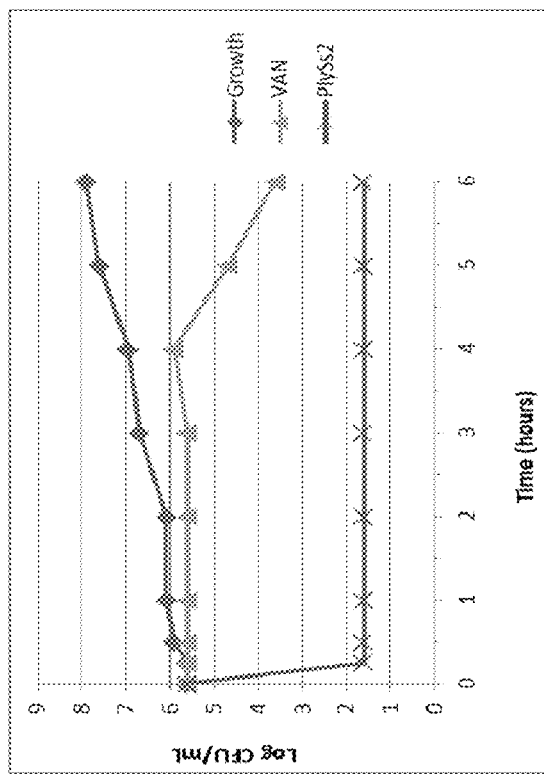
Figure 29:
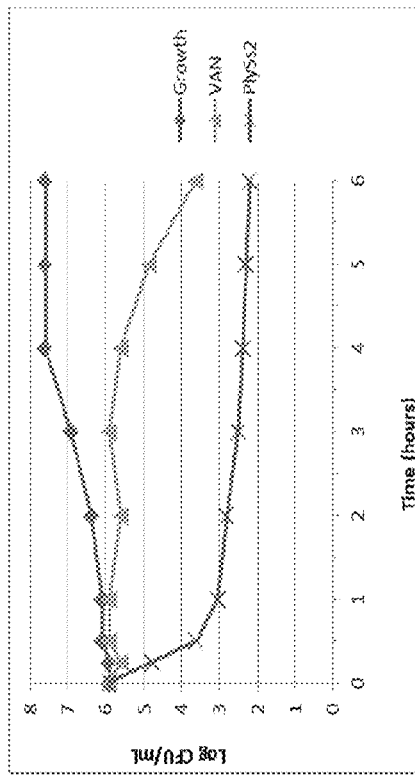
Figure 29:
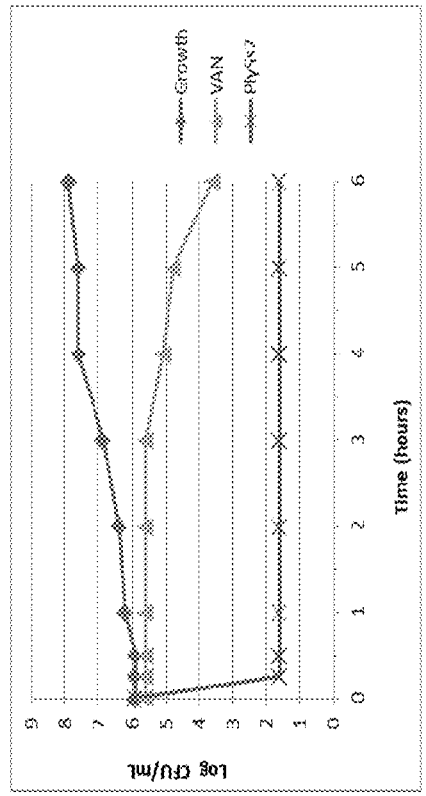

Several MRSA strains (Strain 245, 223, 926 and 932), which all demonstrate similar MIC. values (approx 32 µg/ml) for PlySs2, were tested for log kill by direct comparison between PlySs2 and vancomycin antibiotic (1 µg/ml). Cultures of about $5 \times 10^5$ bacteria are grown in MHB media in 50 ml conical tubes at 37° C. shaking 225 rpms for up to 6 hours in combination with PlySs2 alone, vanvomycin alone, or no additive. At various time points (15 min, 30 min, 1 hr, 2 hrs, 3 hrs, 4 hrs, 5 hrs and 6 hrs) aliquot samples (approx 300 μl) are removed. The lytic enzyme or antibiotic are inactivated by addition of a charcoal solution to all aliquot samples. Samples are diluted and plated on agar plates to determine viable bacterial cell counts. The Log reduction in CFU is depicted in FIG. 29. PlySs2 provides rapid and effective kill with enhanced activiity versus standard-of-care antibiotic vancomycin on all MRSA strains tested and depicted.

DISCUSSION

The novel, native *S. suis* lysin, PlySs2, is demonstrated herein to display broad lytic activity against multiple Gram-positive pathogens including *S. pyogenes* and *S. aureus* in vivo. This lysin is the first to display such promiscuous activity; all previously characterized lysins display activity against a narrow spectrum of species [48, 50, 61-64]. ClyS, has been shown to clear septicemic MRSA infections [50], however, to date, no lysin has been shown to clear more than one septicemic infection, and none has cleared a mixed infection of any kind. The ability of PlySs2 to clear a mixed infection of staphylococci and streptococci comes from its broad lytic activity. Although the in vitro activity of PlySs2 is more robust against MRSA than *S. pyogenes*, the in vivo data provided herein demonstrates its efficacy as an effective therapeutic against both bacteria. This may be due to differences in the structure or composition of the *S. aureus* cell wall compared to that of *S. pyogenes* affecting substrate accessibility. All of the Gram-positive pathogens against which PlySs2 has activity have developed resistance against conventional antibiotics. Neither *S. pyogenes* nor MRSA were able to establish resistance to PlySs2.

A strength of many lysins (including PlySs2) is their specificity. Antibiotics act nonspecifically, killing commensal microbes along with the target pathogen. This results in many negative side effects (eg. diarrhea) and antibiotics can enable opportunistic pathogens (eg. *Clostridium difficile*) to cause entirely new infections. Lysins can be used to treat a single pathogen without disrupting the entire bacterial flora [18]. The specificity of many previously described lysins can also be a limitation in that multiple lysins would be needed to treat multiple pathogens. Our findings provide a single lysin that can be used to treat many pathogens while retaining a degree of specificity. PlySs2 is active against various Gram-positive pathogens leaving the Gram-negatives unaffected.

PlySs2 can serve as a viable treatment for infections caused by *S. aureus* and/or *S. pyogenes* such as: scarlet fever; erysipelas; cellulitis; necrotizing fasciitis; endocarditis; bacteremia/sepsis; a variety of abscess and non-abscess forming SSTIs; and impetigo. Treatment against neonatal septicemia and food-borne illness is also applicable, because it displays more in vitro activity against *S. agalactiae* and *L. monocytogenes* than it does against *S. pyogenes* 5005 (FIG. 25-27).

As a lysin, PlySs2 rapidly kills its target, far quicker than antibiotics (FIG. 29). PlySs2 only has to contact the bonds of the external cell wall to mediate its effect; conventional antibiotics must remain at high concentrations for an extended period, resulting in a multitude of side effects. This feature has enabled phage lysins to treat systemic infections in the past [48, 61]. As demonstrated herein, PlySs2 was able to clear septicemic MRSA and *S. pyogenes* infections from a high percentage of mice using a single dose of PlySs2. In addition, mixed septicemic MRSA and *S. pyogenes* infections were cleared from ~92% of mice with a single dose of PlySs2 compared to ~4% clearance for controls. Further enhanced kill or clearance may arise from increased or repeated dosage.

PlySs2 is more tractable and stable than previously developed lysins. PlySs2 preparation is straightforward, yielding large quantities in few steps. In addition, a highly soluble lysin is essential, because it allows for ready use at high concentrations. Remarkably, PlySs2 remains soluble in concentrations exceeding 20 mg/ml (data not shown) which is orders of magnitude more concentrated than needed to produce log-fold killing of target organisms in a matter of minutes. PlySs2 also behaves well in a variety of in vitro assays developed to evaluate lysins. It can be subjected to high or low temperatures for prolonged periods with little affect on its activity even when repeatedly freeze-thawed. PlySs2's stability is highly suitable for production and distribution as a therapeutic.

The lack of DTT having an effect on PlySs2 activity indicates both that [1] the lysin does not rely on disulfide bridges, and [2] it was properly folded following recombinant expression and purification. The latter point is significant given that LySMP had to be treated with reducing agents prior to use [54]. The reason for this discrepancy between two homologous lysins is unclear, although it may involve the numerous variable cysteine residues between the proteins. The EDTA-induced inhibition of PlySs2 suggests that it may rely upon a divalent cation as a cofactor.

Two lysins have been previously shown to have lytic activity against a number of species, but neither lysin was tested against more than one species in vivo [65, 66] and each lysin retained more activity against the species (*Enterococcus* or *B. anthracis*) from which it was cloned, whereas PlySs2 has more activity against *S. aureus* than *S. suis*.

Consistent with its novel broad lytic activity, PlySs2 represents a divergent class of prophage lytic enzyme structure. CHAP domains are included in several previously characterized streptococcal [59, 67] and staphylococcal [50, 68] phage lysins. On a primary sequence level, however, the CHAP domain of PlySs2 is rather divergent from other database CHAP domains (all pairwise E-values $>10^{15}$). In FIG. 30, the CHAP domain of PlySs2 is aligned with that of the well-characterized streptococcal PlyC lysin, demonstrating conserved catalytic residues, but only a modest level of identity overall (28% sequence identity, E-value=$10^{-8}$) [59].

CHAP domains are catalytically diverse and can possess either alanine-amidase [47] or cross-bridge endopeptidase activity [50], depending on the particular lysin. Further, the molecular nature of the peptidoglycan cross-bridge in *S. suis* can vary between strains [69]. The CHAP domain mediates the catalytic activity of PlySs2, but may not fully confer specificity. It has been thought that the phage lysin binding domains determine lysin specificity [70, 71]. Lysostaphin contains an SH3-like binding domain that presumably binds the cross-bridges in the bacterial cell wall peptidoglycan [71]. SH3 domains are commonly seen in viral and bacterial cell wall-binding proteins, although the exact molecular target remains unknown [72]. SH3b (bacterial homologues of SH3 domains) have been shown to bind metals and polypeptides [73, 74]. An SH3b domain of a *B. cereus* endopeptidase has been shown to bind the free amine group of the N-terminal alanine in the peptidoglycan stem [75] and this amine group is possible substrate for the PlySs2 SH3b domain. The cross-bridge varies greatly across all PlySs2-susceptible specimens, so it is an unlikely target for the PlySs2 SH3 binding domain. These cross-bridges can acquire variations leading to lysostaphin resistance, however PlySs2 notably displayed activity against both lysostaphin-sensitive and lysostaphin-resistant (LyrA) S. aureus strains.

PlySs2 has activity against two, distinct phylogenetic orders: Bacillales (*Staphylococcus, Listeria*, et al.) and Lactobacillales (*Streptococcus, Enterococcus*, et al.). The peptidoglycan stems are similar between these two orders, but their cross-bridges vary widely in composition and length [76, 77]. Phage lysins have not previously displayed activity on different families or genera (and rarely on different species) [50]. Native phage lysins usually show species specificity toward the species the native phage infects [48, 61]. All *S. aureus* strains tested, including strains resistant to methicillin (MRSA), vancomycin (VISA), mupirocin, daptomycin, and lysostaphin were susceptible to PlySs2-induced lysis. PlySs2 lysed the pathogenic *S. suis* 7997 with similar efficacy. Lysing only 2 of 6 strains tested, PlySs2 activity against *Listeria* was less determinate. The activity of PlySs2 against *Staphylococcus simulans, Streptococcus equi zooepidemicus*, and *Staphylococcus equi* provides further evidence that the substrate for the binding domain exists outside of the cross-bridge. The polysaccharide capsule around *S. agalactiae* enhances its virulence. Type II *S. agalactiae* has a thicker capsule than most, and has a correspondingly higher level of virulence [28]. *S. agalactiae* strains with a thinner capsule are less virulent [29, 78]. PlySs2 has comparable activity against those with and without a capsule: *S. agalactiae*_Type II, *S. agalactiae* 090R. There are greater than 200 M types for *S. pyogenes* [4]. Remarkably, PlySs2 has activity against all of the M-types we tested it against. PlySs2 activity against *S. sanguinis* indicates its potential to treat dental plaque. Although PlySs2 displays activity against *S. gordonii*, it displays less activity against the commensals *S. oralis*, and *S. mutans*. There is a moderate amount of activity against group G *Streptococcus*, group E *Streptococcus*, *E. facaelis*, *S. pneumoniae*, *S. rattus*, and *S. sobrinus*. Other strains of *S. pneumoniae* were less susceptible. The activity of PlySs2 against an array of multidrug-resistant MRSA, heavily capsulated *S. pyogenes*, and numerous other virulent pathogens make it a critical therapeutic candidate. Remarkably, PlySs2 was able to reduce the CFU's of various strains that varied in drug resistance, capsulation, and biofilm creation. PlySs2's activity against the mucoid *S. pyogenes* M4 was stronger than was observed for any other *S. pyogenes* tested. Further, PlySs2 had a greater activity against *S. agalactiae* and *L. monocytogenes* than *S. pyogenes* (from which it was able to protect septicemic mice). Given the efficacy of PlySs2 against *S. pyogenes*, PlySs2 can serve as a therapeutic agent against any of these other pathogens. The MIC results confirmed the CFU findings.

In murine studies, singly infected animals demonstrate that PlySs2 can independently protect against multiple species of bacterial infection. In the mixed infection, specific lysin controls (PlyC and ClyS) show PlySs2 is protecting the mice from both organisms in the mixed or duel infection. Using either PlyC or ClyS to treat only one of the infectious pathogens in the mixed model still resulted in the death of the animals. Further, the animals die in the same time frame as the singly infected non-treated controls. *S. aureus* and *S. pyogenes* cause diseases with similar pathologies and sites of infection in man. Healthcare providers are sometimes not sure at first which organism is causing disease which could be a mixed infection in severe trauma cases. Severe invasive *S. pyogenes* infections are not easily treated with antibiotics [82]. In some cases, they require surgical procedures [82]. The M1 serotype used in our septicemic model is one of the leading clinical isolates found causing streptococcal pharyngitis and invasive disease worldwide [83, 84]. *S. pyogenes* is able to traverse epithelial surfaces producing invasive bacteremia [83]. This and other severe internal infections result in death in less than a week in 19% of the cases [85]. In many cases, one does not know whether *S. aureus* or *S. pyogenes* is the causative pathogen behind SSTIs or impetigo.

The inability of pathogenic targets (MRSA and *S. pyogenes*) to establish resistance to PlySs2 is consistent with findings for other lysins including PlyG [61]. To date, a molecule that can break down lysins exogenously has not been identified. It is unlikely that a pathogen would be able to readily alter the target site given the nature of peptidoglycan. The extremely low probability of resistance makes PlySs2 a compelling therapeutic. Mupirocin and polysporin are typically given to treat *S. aureus*, but it can develop resistance to each. They are the only anti-infectives given to reduce colonizing pathogenic bacteria on mucous membranes [86]. PlySs2 can be used to prophylactically clear human mucous membrane reservoirs of pathogenic bacteria resistant to antibiotics. Penicillin can be used to treat *S. pyogenes*, which remains acutely sensitive; but if the impetigo is caused by MRSA, penicillin may be ineffective.

Recent studies have indicated that secondary infections caused by *S. pneumococcus*, *S. pyogenes*, and MRSA account for >90% of deaths from influenza pandemics [92, 93]. The same pathogens caused complications in nearly 30% of the 2010 H1N1 pandemic cases [94]. Prophylactic usage could decrease the rate of these fatalities. PlySs2 may treat primary infections and prophylactically decrease the likelihood of secondary infections.

Before identification of the pathogen, standard of care is to treat the most likely candidates given the nature and environment of the infection [95, 96]. Many of these pathogens, especially MRSA, readily develop resistance to traditional and novel antibiotics, especially beta-lactams. MRSA is also resistant to newer agents, glycopeptides, oxazolidinones [97, 98]. PlySs2 has specificity to Gram-positives, but could broadly treat *S. pyogenes*, MRSA, and other prominent pathogens.

As a treatment, PlySs2 would target the pathogens, without harming Gram-negatives. This novel capability lies in the divergent CHAP domain, and unique SH3 binding domain. Antibiotics kill many species in addition to the target pathogen. Previously, lysins could only be used against one pathogenic species. PlySs2 occupies a vital space in the spectrum between the rigid lysin specificity, and unselective antibiotic activity. Ideally, a therapeutic has activity against all the major pathogens without affecting the commensals; PlySs2 is the first to indicate that a lysin could serve that function. PlySs2 is a lysin with broad lytic activity against MRSA, VISA, *S. suis, Listeria, S. simulans, S. equi zoo, S. equi, S. agalactiae, S. pyogenes, S. sanguinis, S. gordonii*, group G *Streptococcus*, group E *Streptococcus*, *E. faecalis*, and *S. pneumoniae*. PlySs2 is easy to produce, tractable, and very stable. PlySs2 protects septicemic mice from a mixed infection of MRSA and *S. pyogenes* and neither of these pathogens were able to establish resistance to PlySs2.

REFERENCES

1. Mandell, G. L., et al. *Mandell, Douglas, and Bennett's principles and practice of infectious diseases*. [Book review (E-STREAMS)] 2005; 6th: [Available from: e-streams.com/es0806_7/es0867_4196. html.

2. Carapetis, J. R., et al., *The global burden of group A streptococcal diseases*. The Lancet infectious diseases, 2005. 5(11): p. 685-694.
3. Cunningham, M. W., *Pathogenesis of group A streptococcal infections*. Clin Microbiol Rev, 2000. 13(3): p. 470-511.
4. Bessen, D. E., et al., *Whole Genome Association Study on Tissue Tropism Phenotypes in Group A Streptococcus*. Journal of Bacteriology, 2011: p. JB. 05263-11v1.
5. Parker, M. T., A. J. Tomlinson, and R. E. Williams, *Impetigo contagiosa; the association of certain types of Staphylococcus aureus and of Streptococcus pyogenes with superficial skin infections*. J Hyg (Lond), 1955. 53(4): p. 458-73.
6. Bisno, A. L., M. O. Brito, and C. M. Collins, *Molecular basis of group A streptococcal virulence*. Lancet Infect Dis, 2003.3(4): p. 191-200.
7. Swedo, S. E., et al., *Identification of children with pediatric autoimmune neuropsychiatric disorders associated with streptococcal infections by a marker associated with rheumatic fever*. Am J Psychiatry, 1997. 154(1): p. 110-2.
8. Kavey, R. and E. L. Kaplan, *Resurgence of acute rheumatic fever*. Pediatrics, 1989. 84(3): p. 585.
9. White, A. and J. Smith, *Nasal Reservoir as the Source of Extranasal Staphylococci*. Antimicrob Agents Chemother (Bethesda), 1963. 161: p. 679-83.
10. Kluytmans, J., A. van Belkum, and H. Verbrugh, *Nasal carriage of Staphylococcus aureus: epidemiology, underlying mechanisms, and associated risks*. Clin Microbiol Rev, 1997. 10(3): p. 505-20.
11. von Eiff, C., et al., *Nasal carriage as a source of Staphylococcus aureus bacteremia*. New England Journal of Medicine, 2001. 344(1): p. 11-16.
12. Wertheim, H. F. L., et al., *The role of nasal carriage in Staphylococcus aureus infections*. Lancet Infectious Diseases, 2005. 5(12): p. 751-762.
13. Howden, B. P., et al., *Reduced vancomycin susceptibility in Staphylococcus aureus, including vancomycin-intermediate and heterogeneous vancomycin-intermediate strains: resistance mechanisms, laboratory detection, and clinical implications*. Clin Microbiol Rev, 2010. 23(1): p. 99-139.
14. Klein, E., D. L. Smith, and R. Laxminarayan, *Hospitalizations and deaths caused by methicillin-resistant Staphylococcus aureus, United States, 1999-2005*. Emerg Infect Dis, 2007. 13(12): p. 1840-6.
15. Coates, T., R. Bax, and A. Coates, *Nasal decolonization of Staphylococcus aureus with mupirocin: strengths, weaknesses and future prospects*. J Antimicrob Chemother, 2009. 64(1): p. 9-15.
16. Tiemersma, E. W., et al., *Methicillin-resistant Staphylococcus aureus in Europe, 1999ñ2002*. Emerg Infect Dis, 2004. 10(9): p. 1627-34.
17. Laupland, K. B., T. Ross, and D. B. Gregson, *Staphylococcus aureus bloodstream infections. risk factors, outcomes, and the influence of methicillin resistance in Calgary, Canada, 2000ñ2006*. Journal of Infectious Diseases, 2008. 198(3): p. 336.
18. Fischetti, V. A., *Bacteriophage lysins as effective antibacterials*. Curr Opin Microbiol, 2008. 11(5): p. 393-400.
19. *From the Centers for Disease Control and Prevention. Four pediatric deaths from community-acquired methicillin-resistant Staphylococcus aureus—Minnesota and North Dakota, 1997-1999*. JAMA, 1999. 282(12): p. 1123-5.
20. Herold, B. C., et al., *Community-acquired methicillin-resistant Staphylococcus aureus in children with no identified predisposing risk*. JAMA: the journal of the American Medical Association, 1998. 279(8): p. 593-598.
21. Adem, P. V., et al., *Staphylococcus aureus sepsis and the Waterhouse-Friderichsen syndrome in children*. N Engl J Med, 2005. 353(12): p. 1245-51.
22. Miller, L. G., et al., *Necrotizing fasciitis caused by community-associated methicillin-resistant Staphylococcus aureus in Los Angeles*. N Engl J Med, 2005. 352(14): p. 1445-53.
23. Li, M., et al., *Evolution of virulence in epidemic community-associated methicillin-resistant Staphylococcus aureus*. Proc Natl Acad Sci USA, 2009. 106(14): p. 5883-8.
24. Voyich, J. M., et al., *Insights into mechanisms used by Staphylococcus aureus to avoid destruction by human neutrophils*. J Immunol, 2005. 175(6): p. 3907-19.
25. Vandenesch, F., et al., *Community-acquired methicillin-resistant Staphylococcus aureus carrying Panton-Valentine leukocidin genes: worldwide emergence*. Emerg Infect Dis, 2003. 9(8): p. 978-84.
26. Tristan, A, et al., *Global distribution of Panton-Valentine leukocidin—positive methicillin-resistant Staphylococcus aureus*, 2006. Emerg Infect Dis, 2007. 13(4): p. 594-600.
27. Deleo, F. R., et al., *Community-associated meticillin-resistant Staphylococcus aureus*. Lancet, 2010. 375 (9725): p. 1557-68.
28. Yeung, M. and S. Mattingly, *Biosynthetic capacity for type-specific antigen synthesis determines the virulence of serotype III strains of group B streptococci*. Infection and immunity, 1984. 44(2): p. 217.
29. Rubens, C., et al., *Transposon mutagenesis of type III group B Streptococcus: correlation of capsule expression with virulence*. Proceedings of the National Academy of Sciences, 1987. 84(20): p. 7208.
30. Boyer, K. M., et al., *Selective intrapartum chemoprophylaxis of neonatal group B streptococcal early-onset disease. II. Predictive value of prenatal cultures*. Journal of Infectious Diseases, 1983. 148(5): p. 802.
31. Meyn, L. A., M. A. Krohn, and S. L. Hillier, *Rectal colonization by group B Streptococcus as a predictor of vaginal colonization*. American journal of obstetrics and gynecology, 2009. 201(1): p. 76. el-76. e7.
32. Lancefield, R. C. and R. Hare, *The serological differentiation of pathogenic and non-pathogenic strains of hemolytic streptococci from parturient women*. The Journal of experimental medicine, 1935. 61(3): p. 335.
33. Fry, R. M., *Prevention and Control of Puerperal Sepsis: Bacteriological Aspects*. Br Med J, 1938. 2(4049): p. 340-2.
34. Hare, R. and L. Colebrook, *The biochemical reactions of hÊmolytic streptococci from the vagina of febeile and afebeile parturient women*. The Journal of Pathology and Bacteriology, 1934. 39(2): p. 429-442.
35. Zangwill, K., A. Schuchat, and J. Wenger, *Group B streptococcal disease in the United States, 1990: report from a multistate active surveillance system*. MMWR. CDC surveillance summaries: Morbidity and mortality weekly report. CDC surveillance summaries/Centers for Disease Control, 1992. 41(6): p. 25.
36. Baertlein, L., *Death toll from listeria outbreak rises to 29*, C. Johnston, Editor 2011, Reuters.
37. Schuppler, M. and M. J. Loessner, *The Opportunistic Pathogen Listeria monocytogenes: Pathogenicity and Interaction with the Mucosal Immune System*. hit J Inflam, 2010. 2010: p. 704321.

38. Hof, H., K. Szabo, and B. Becker, *Epidemiology of listeriosis in Germany: a changing but ignored pattern*]. Deutsche medizinische Wochenschrift (1946), 2007. 132 (24): p. 1343.
39. Ramaswamy, V., et al., *Listeria—review of epidemiology and pathogenesis*. J Microbiol Immunol Infect, 2007. 40(1): p. 4-13.
40. Dieterich, G., et al., *LEGER: knowledge database and visualization tool for comparative genomics of pathogenic and non-pathogenic Listeria species*. Nucleic Acids Research, 2006. 34(suppl 1): p. D402.
41. Sriskandan, S. and J. D. Slater, *Invasive disease and toxic shock due to zoonotic Streptococcus suis: an emerging infection in the East?* PLoS Med, 2006. 3(5): p. e187.
42. Cantin, M., et al., *Antimicrobial resistance patterns and plasmid profiles of Streptococcus suis isolates*. J Vet Diagn Invest, 1992. 4(2): p. 170-4.
43. O'Flaherty, S., R. P. Ross, and A. Coffey, *Bacteriophage and their lysins for elimination of infectious bacteria*. FEMS Microbiol Rev, 2009. 33(4): p. 801-19.
44. González Villa, T. and P. Veiga-Crespo, *Enzybiotics: antibiotic enzymes as drugs and therapeutics* 2010, Hoboken, N.J.: John Wiley & Sons. x, 284 p.
45. Wang, I. N., D. L. Smith, and R. Young, *Holins: the protein clocks of bacteriophage infections*. Annu Rev Microbiol, 2000. 54: p. 799-825.
46. Beres, S. B. and J. M. Musser, *Contribution of exogenous genetic elements to the group A Streptococcus metagenome*. PLoS One, 2007. 2(8): p. e800.
47. Nelson, D., L. Loomis, and V. A. Fischetti, *Prevention and elimination of upper respiratory colonization of mice by group A streptococci by using a bacteriophage lytic enzyme*. Proc Natl Acad Sci USA, 2001. 98(7): p. 4107-12.
48. Loeffler, J. M., D. Nelson, and V. A. Fischetti, *Rapid killing of Streptococcus pneumoniae with a bacteriophage cell wall hydrolase*. Science, 2001. 294(5549): p. 2170-2.
49. Fischetti, V. A., *Bacteriophage lytic enzymes: novel anti-infectives*. Trends Microbiol, 2005. 13(10): p. 491-6.
50. Daniel, A, et al., *Synergism between a novel chimeric lysin and oxacillin protects against infection by methicillin-resistant Staphylococcus aureus*. Antimicrob Agents Chemother, 2010. 54(4): p. 1603-12.
51. Cheng, Q., et al., *Removal of group B streptococci colonizing the vagina and oropharynx of mice with a bacteriophage lytic enzyme*. Antimicrob Agents Chemother, 2005. 49(1): p. 111-7.
52. Harel, J., et al., *Identification of an inducible bacteriophage in a virulent strain of Streptococcus suis serotype 2*. Infect Immun, 2003. 71(10): p. 6104-8.
53. Ma, Y. L. and C. P. Lu, *Isolation and identification of a bacteriophage capable of infecting Streptococcus suis type 2 strains*. Vet Microbiol, 2008. 132(3-4): p. 340-7.
54. Wang, Y., J. H. Sun, and C. P. Lu, *Purified recombinant phage lysin LySMP: an extensive spectrum of lytic activity for swine streptococci*. Curr Microbiol, 2009. 58(6): p. 609-15.
55. Holden, M. T., et al., *Rapid evolution of virulence and drug resistance in the emerging zoonotic pathogen Streptococcus suis*. PLoS One, 2009. 4(7): p. e6072.
56. Chen, C., et al., *A glimpse of streptococcal toxic shock syndrome from comparative genomics of S. suis 2 Chinese isolates*. PLoS One, 2007. 2(3): p. e315.
57. Wiegand, I., K. Hilpert, and R. E. Hancock, *Agar and broth dilution methods to determine the minimal inhibitory concentration (MIC) of antimicrobial substances*. Nat Protoc, 2008. 3(2): p. 163-75.
58. Rouse, M. S., et al., *In vitro and in vivo evaluations of the activities of lauric acid monoester formulations against Staphylococcus aureus*. Antimicrob Agents Chemother, 2005. 49(8): p. 3187-91.
59. Nelson, D., et al., *PlyC: a multimeric bacteriophage lysin*. Proc Natl Acad Sci USA, 2006. 103(28): p. 10765-70.
60. Lucas, S., A Copeland, A. Lapidus, et al., *Sequencing of the draft genome and assembly of Streptococcus suis 89/1591*, in *Unpublished* 2004.
61. Schuch, R., D. Nelson, and V. A. Fischetti, *A bacteriolytic agent that detects and kills Bacillus anthracis*. Nature, 2002. 418(6900): p. 884-9.
62. O'Flaherty, S., et al., *The recombinant phage lysin LysK has a broad spectrum of lytic activity against clinically relevant staphylococci, including methicillin-resistant Staphylococcus aureus*. Journal of Bacteriology, 2005. 187(20): p. 7161-4.
63. Zimmer, M., et al., *The murein hydrolase of the bacteriophage phi3626 dual lysis system is active against all tested Clostridium perfringens strains*. Appl Environ Microbiol, 2002. 68(11): p. 5311-7.
64. Loessner, M. J., et al., *Three Bacillus cereus bacteriophage endolysins are unrelated but reveal high homology to cell wall hydrolases from different bacilli*. J Bacteriol, 1997. 179(9): p. 2845-51.
65. Yoong, P., et al., *Identification of a broadly active phage lytic enzyme with lethal activity against antibiotic-resistant Enterococcus faecalis and Enterococcus faecium*. J Bacteriol, 2004. 186(14): p. 4808-12.
66. Yoong, P., et al., *PlyPH, a bacteriolytic enzyme with a broad pH range of activity and lytic action against Bacillus anthracis*. J Bacteriol, 2006. 188(7): p. 2711-4.
67. Baker, J. R., et al., *Endopeptidase and glycosidase activities of the bacteriophage B30 lysin*. Appl Environ Microbiol, 2006. 72(10): p. 6825-8.
68. Becker, S. C., et al., *LysK CHAP endopeptidase domain is required for lysis of live staphylococcal cells*. FEMS Microbiol Left, 2009. 294(1): p. 52-60.
69. Kilpperbalz, R. and K. H. Schleifer, *Streptococcus-Suis Sp-Nov, Nom-Rev*. International Journal of Systematic Bacteriology, 1987. 37(2): p. 160-162.
70. Hermoso, J. A., et al., *Structural basis for selective recognition of pneumococcal cell wall by modular endolysin from phage Cp-1*. Structure, 2003. 11(10): p. 1239-49.
71. Grundling, A and O. Schneewind, *Cross-linked peptidoglycan mediates lysostaphin binding to the cell wall envelope of Staphylococcus aureus*. Journal of Bacteriology, 2006. 188(7): p. 2463-72.
72. Xu, Q., et al., *Structural basis of murein peptide specificity of a gamma-D-glutamyl-l-diamino acid endopeptidase*. Structure, 2009. 17(2): p. 303-13.
73. Pohl, E., R. K. Holmes, and W. G. Hol, *Crystal structure of a cobalt-activated diphtheria toxin repressor-DNA complex reveals a metal-binding SH3-like domain*. J Mol Biol, 1999. 292(3): p. 653-67.
74. Wylie, G. P., et al., *Prolylpeptide binding by the prokaryotic SH3-like domain of the diphtheria toxin repressor: a regulatory switch*. Biochemistry, 2005. 44(1): p. 40-51.
75. Xu, Q., et al., *Structure of the gamma-D-glutamyl-L-diamino acid endopeptidase YkfC from Bacillus cereus in complex with L-Ala-gamma-D-Glu: insights into substrate recognition by NlpC/P60 cysteine peptidases*. Acta Crystallogr Sect F Struct Biol Cryst Commun, 2010. 66(Pt 10): p. 1354-64.

76. Vollmer, W., D. Blanot, and M. A. de Pedro, *Peptidoglycan structure and architecture*. FEMS Microbiol Rev, 2008. 32(2): p. 149-67.
77. Schleifer, K. H. and O. Kandler, *Peptidoglycan types of bacterial cell walls and their taxonomic implications*. Bacteriol Rev, 1972. 36(4): p. 407-77.
78. Wessels, M. R., et al., *Definition of a bacterial virulence factor: sialylation of the group B streptococcal capsule*. Proc Natl Acad Sci USA, 1989. 86(22): p. 8983-7.
79. Robinson, J. M., J. K. Hardman, and G. L. Sloan, *Relationship between lysostaphin endopeptidase production and cell wall composition in Staphylococcus staphylolyticus*. J Bacteriol, 1979. 137(3): p. 1158-64.
80. Gargis, S. R., et al., *Inhibition of the activity of both domains of lysostaphin through peptidoglycan modification by the lysostaphin immunity protein*. Appl Environ Microbiol, 2010. 76(20): p. 6944-6.
81. Rashel, M., et al., *Efficient elimination of multidrug-resistant Staphylococcus aureus by cloned lysin derived from bacteriophage phi MR11*. J Infect Dis, 2007. 196(8): p. 1237-47.
82. Young, M. H., D. M. Aronoff, and N. C. Engleberg, *Necrotizing fasciitis: pathogenesis and treatment*. Expert Rev Anti Infect Ther, 2005. 3(2): p. 279-94.
83. Cole, J. N., et al., *Molecular insight into invasive group A streptococcal disease*. Nat Rev Microbiol, 2011. 9(10): p. 724-36.
84. Steer, A C., et al., *Global emm type distribution of group A streptococci: systematic review and implications for vaccine development*. Lancet Infect Dis, 2009. 9(10): p. 611-6.
85. Lamagni, T. L., et al., *Epidemiology of severe Streptococcus pyogenes disease in Europe*. J Clin Microbiol, 2008. 46(7): p. 2359-67.
86. Hudson, I. R., *The efficacy of intranasal mupirocin in the prevention of staphylococcal infections: a review of recent experience*. J Hosp Infect, 1994. 27(2): p. 81-98.
87. Loeffler, J. M., S. Djurkovic, and V. A. Fischetti, *Phage lytic enzyme Cpl-1 as a novel antimicrobial for pneumococcal bacteremia*. Infect Immun, 2003. 71(11): p. 6199-204.
88. Loessner, M. J., et al., *C-terminal domains of Listeria monocytogenes bacteriophage murein hydrolases determine specific recognition and high-affinity binding to bacterial cell wall carbohydrates*. Mol Microbiol, 2002. 44(2): p. 335-49.
89. Jado, I., et al., *Phage lytic enzymes as therapy for antibiotic-resistant Streptococcus pneumoniae infection in a murine sepsis model*. J Antimicrob Chemother, 2003. 52(6): p. 967-73.
90. Grandgirard, D., et al., *Phage lytic enzyme Cpl-1 for antibacterial therapy in experimental pneumococcal meningitis*. J Infect Dis, 2008. 197(11): p. 1519-22.
91. Witzenrath, M., et al., *Systemic use of the endolysin Cpl-1 rescues mice with fatal pneumococcal pneumonia*. Crit Care Med, 2009. 37(2): p. 642-9.
92. Morens, D. M., J. K. Taubenberger, and A. S. Fauci, *The persistent legacy of the 1918 influenza virus*. N Engl J Med, 2009. 361(3): p. 225-9.
93. Brundage, J. F. and G. D. Shanks, *What really happened during the 1918 influenza pandemic? The importance of bacterial secondary infections*. J Infect Dis, 2007. 196(11): p. 1717-8; author reply 1718-9.
94. *Bacterial coinfections in lung tissue specimens from fatal cases of 2009 pandemic influenza A (H1N1)—United States, May-August 2009*. MMWR Morb Mortal Wkly Rep, 2009. 58(38): p. 1071-4.
95. Cunha, B. A., *Sepsis and septic shock: selection of empiric antimicrobial therapy*. Crit Care Clin, 2008. 24(2): p. 313-34, ix.
96. Dellinger, R. P., et al., *Surviving Sepsis Campaign guidelines for management of severe sepsis and septic shock*. Crit Care Med, 2004. 32(3): p. 858-73.
97. Wilson, P., et al., *Linezolid resistance in clinical isolates of Staphylococcus aureus*. J Antimicrob Chemother, 2003. 51(1): p. 186-8.
98. Huang, Y. T., et al., *Bacteremia and infective endocarditis caused by a non-daptomycin-susceptible, vancomycin-intermediate, and methicillin-resistant Staphylococcus aureus strain in Taiwan*. J Clin Microbiol, 2008. 46(3): p. 1132-6.
99. Zhang, A., Yang, M., Hu, P., Wu, J., Chen, B., Hua, Y., Yu, J., Chen, H., Xiao, J. and Jin, M. Comparative genomic analysis of *Streptococcus suis* reveals significant genomic diversity among different serotype BMC Genomics 12, 523 (2011).

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

What is claimed is:

1. A method of killing *Staphylococcus* and *Streptococcus* bacteria comprising the step of contacting the bacteria with a pharmaceutical composition comprising the isolated lysin polypeptide comprising the amino acid sequence of SEQ ID NO:3 or variants thereof having at least 80% identity to the polypeptide of SEQ ID NO:3 and effective to kill *Staphylococcus* and *Streptococcus* bacteria comprising an amount of the isolated lysin polypeptide effective to kill the *Staphylococcus* and *Streptococcus* bacteria.

2. The method of claim 1 wherein the composition further comprises an effective amount of the isolated lysin polypeptide comprising the amino acid sequence of SEQ ID NO:1, the isolated lysin polypeptide comprising the amino acid sequence of SEQ ID NO:2, or variants thereof having at least 80% identity to the polypeptide of SEQ ID NO:1 or of SEQ ID NO:2 and effective to kill the *Staphylococcus* and *Streptococcus* bacteria.

3. The method of claim 1 wherein the bacteria is an antibiotic resistant bacteria.

4. The method of claim 1 wherein the bacteria is methicillin-resistant *Staphylococcus aureus* (MRSA), vancomycin intermediate-sensitivity *Staphylococcus aureus* (VISA), or vancomycin resistant *Staphylococcus aureus* (VRSA).

5. A method for reducing a population of *Staphylococcus* and *Streptococcus* bacteria comprising the step of contacting the bacteria with a pharmaceutical composition comprising the isolated lysin polypeptide comprising the amino acid sequence of SEQ ID NO:3 or variants thereof having at least 80% identity to the polypeptide of SEQ ID NO:3 and effective to kill *Staphylococcus* and *Streptococcus* bacteria comprising an amount of the isolated polypeptide effective to kill at least a portion of the *Staphylococcus* and *Streptococcus* bacteria.

6. The method of claim 5 wherein the composition further comprises an effective amount of the isolated lysin polypeptide comprising the amino acid sequence of SEQ ID NO:1, the isolated lysin polypeptide comprising the amino acid sequence of SEQ ID NO:2, or variants thereof having at least 80% identity to the polypeptide of SEQ ID NO:1 or of SEQ ID NO:2 and effective to kill the *Staphylococcus* and *Streptococcus* bacteria.

7. The method of claim 5 wherein the bacteria is an antibiotic resistant bacteria.

8. The method of claim 5 wherein the bacteria is methicillin-resistant *Staphylococcus aureus* (MRSA), vancomycin intermediate-sensitivity *Staphylococcus aureus* (VISA), or vancomycin resistant *Staphylococcus aureus* (VRSA).

9. A method for treating gram-positive bacterial infection caused by *Staphylococcus* strains, *Streptococcus* strains, *Listeria monocytogenes* or *Enterococcus faecalis* bacteria in a human comprising the step of administering to a human having a bacterial infection, an effective amount a pharmaceutical composition comprising the isolated polypeptide comprising the amino acid sequence of SEQ ID NO:3 or variants thereof having at least 80% identity to the polypeptide of SEQ ID NO:3 and effective to kill the *Staphylococcus, Streptococcus, Listeria* or *Enterococcus* bacteria, whereby the number of *Staphylococcus, Streptococcus, Listeria* or *Enterococcus* bacteria in the human is reduced and the infection is controlled.

10. The method of claim 9 wherein the composition further comprises an effective amount of the isolated lysin polypeptide comprising the amino acid sequence of SEQ ID NO:1, the isolated lysin polypeptide comprising the amino acid sequence of SEQ ID NO:2, or variants thereof having at least 80% identity to the polypeptide of SEQ ID NO:1 or of SEQ ID NO:2 and effective to kill the gram-positive bacteria.

11. The method of claim 9 wherein the bacteria is selected from *Staphylococcus aureus, Staphylococcus simulans, Streptococcus suis, Staphylococcus epidermidis, Streptococcus equi, Streptococcus agalactiae* (GBS), *Streptococcus pyogenes* (GAS), *Streptococcus sanguinis, Streptococcus gordonii, Streptococcus dysgalactiae, Streptococcus* GES and *Streptococcus pneumonia*.

12. A method for treating a human subject exposed to or at risk for exposure to a pathogenic *Staphylococcus* strain, *Streptococcus* strain, *Listeria monocytogenes* or *Enterococcus faecalis* bacteria comprising the step of administering to the human subject a pharmaceutical composition comprising the isolated polypeptide comprising the amino acid sequence of SEQ ID NO:3 or variants thereof having at least 80% identity to the polypeptide of SEQ ID NO:3 and effective to kill the *Staphylococcus, Streptococcus, Listeria* or *Enterococcus* bacteria comprising an amount of the isolated lysin polypeptide effective to kill the *Staphylococcus, Streptococcus, Listeria* or *Enterococcus* bacteria.

13. The method of claim 12 wherein the subject is exposed to or at risk of *Staphylococcus aureus*, Group B *Streptococcus* bacteria (GBS), *Streptococcus pyogenes* (GAS) or *Streptococcus pneumonia*.

14. A method for reducing or controlling gram-positive bacterial infection or contamination caused by *Staphylococcus* strains, *Streptococcus* strains, *Listeria monocytogenes* or *Enterococcus faecalis* bacteria in a human comprising the step of contacting the human, including an external surface or skin of said human, with an effective amount of a pharmaceutical composition comprising the isolated polypeptide comprising the amino acid sequence of SEQ ID NO:3 or variants thereof having at least 80% identity to the polypeptide of SEQ ID NO:3 and effective to kill the *Staphylococcus, Streptococcus, Listeria* or *Enterococcus* bacteria, whereby the number of *Staphylococcus, Streptococcus, Listeria* or *Enterococcus* bacteria is reduced and the infection or contamination is controlled.

15. The method of claim 14 wherein the composition administered is a composition suitable for topical or dermatological application or for administration to the skin or external surface of a human.

16. The method of claim 11, 13 or 14 wherein the bacteria is an antibiotic-resistant *Staphylococcus aureus* bacteria.

* * * * *

SEQUENCE LISTING

```
<160> NUMBER OF SEQ ID NOS: 14

<210> SEQ ID NO 1
<211> LENGTH: 452
<212> TYPE: PRT
<213> ORGANISM: Streptococcus suis

<400> SEQUENCE: 1

Met Thr Ile Asn Leu Glu Thr Ser Ile Arg Trp Met Ser Asp Arg Val
1               5                   10                  15

Gly Lys Val Ser Tyr Ser Met Asp Tyr Arg Asn Gly Pro Asn Ser Tyr
            20                  25                  30

Asp Cys Ser Ser Ala Val Tyr Tyr Ala Leu Met Ala Gly Gly Ala Ile
```

```
                35                  40                  45
Ser Ala Gly Trp Ala Val Asn Thr Glu Tyr Met His Asp Trp Leu Ile
 50                  55                  60

Arg Asn Gly Tyr Val Leu Val Ala Glu Asn Lys Pro Phe Asn Ala Gln
 65                  70                  75                  80

Arg His Asp Val Cys Ile Leu Gly Lys Arg Gly Tyr Ser Ser Gly Ala
                 85                  90                  95

Gly Gly His Val Val Ile Phe Val Asp Asn Val Asn Val Ile His Cys
                100                 105                 110

Asn Tyr Ala Arg Asn Gly Ile Ser Ile Asp Asn Tyr Asn Gln Val His
                115                 120                 125

Arg Gly Met Tyr Tyr Leu Tyr Arg Pro Ala Asn Gln Pro Ser Ile
        130                 135                 140

Ser Asn Lys Ser Leu Asp Gln Leu Val Lys Glu Thr Leu Ala Gly Val
145                 150                 155                 160

His Gly Asn Gly Asp Thr Arg Lys Ala Ser Leu Gly Ser Gln Tyr Glu
                165                 170                 175

Ala Val Met Ala Val Ile Asn Gly Lys Ala Ser Ala Ser Glu Lys Ser
                180                 185                 190

Asp Glu Glu Leu Ala Arg Glu Val Leu Ala Gly Lys His Gly Ala Gly
                195                 200                 205

Glu Asp Arg Lys Arg Ser Leu Gly Pro Arg Tyr Glu Pro Val Gln Ala
        210                 215                 220

Lys Val Asn Glu Leu Leu Lys Ala Lys Glu Lys Pro Ser Glu Thr Ala
225                 230                 235                 240

Lys Asn Glu Pro Gln Thr Val Gln Phe Lys Glu Asp Gly Asp Leu Ser
                245                 250                 255

Phe Asn Gly Ala Ile Leu Lys Lys Ser Val Leu Glu Ile Ile Leu Lys
                260                 265                 270

Lys Cys Lys Glu His Asp Ile Leu Pro Ser Tyr Ala Leu Thr Ile Leu
        275                 280                 285

His Tyr Glu Gly Leu Trp Gly Thr Ser Ala Val Gly Lys Ala Asp Asn
        290                 295                 300

Asn Trp Gly Gly Met Thr Trp Thr Gly Gln Gly Asn Arg Pro Ser Gly
305                 310                 315                 320

Val Ile Val Thr Gln Gly Leu Ala Arg Pro Ser Asn Glu Gly Gly His
                325                 330                 335

Tyr Met His Tyr Ala Thr Val Asp Asp Phe Leu Thr Asp Trp Phe Tyr
                340                 345                 350

Leu Leu Arg Lys Asp Gly Ser Tyr Lys Val Ser Gly Ala Leu Thr Phe
        355                 360                 365

Ser Glu Ser Ile Lys Gly Met Phe Gln Val Gly Gly Ala Lys Tyr Asp
        370                 375                 380

Tyr Ala Ala Gly Tyr Asp Ser Tyr Leu Val Gly Ala Thr Ser Arg
385                 390                 395                 400

Leu Lys Ala Ile Glu Ser Glu Asn Gly Ser Leu Thr Arg Phe Asp Ala
                405                 410                 415

Thr Ser Asn Asn Val His Ser Val Asp Pro Lys Ile Ser Val Asp
                420                 425                 430

Ile Asp Gly Ile Glu Val Thr Ile Asn Gly Val Val Tyr Lys Leu Glu
        435                 440                 445

Lys Lys Pro Val
        450
```

```
<210> SEQ ID NO 2
<211> LENGTH: 255
<212> TYPE: PRT
<213> ORGANISM: Streptococcus suis

<400> SEQUENCE: 2

Met Thr Ile Asn Leu Glu Thr Ser Ile Arg Trp Met Ser Asp Arg Val
1               5                   10                  15

Gly Lys Val Ser Tyr Ser Met Asp Tyr Arg Asn Gly Pro Asn Ser Tyr
            20                  25                  30

Asp Cys Ser Ser Ala Val Tyr Tyr Ala Leu Met Ala Gly Gly Ala Ile
        35                  40                  45

Ser Ala Gly Trp Ala Val Asn Thr Glu Tyr Met His Asp Trp Leu Ile
    50                  55                  60

Arg Asn Gly Tyr Val Leu Val Ala Glu Asn Lys Pro Phe Asn Ala Gln
65                  70                  75                  80

Arg His Asp Val Cys Ile Leu Gly Lys Arg Gly Tyr Ser Ser Gly Ala
                85                  90                  95

Gly Gly His Val Val Ile Phe Val Asp Asn Val Asn Val Ile His Cys
            100                 105                 110

Asn Tyr Ala Arg Asn Gly Ile Ser Ile Asp Asn Tyr Asn Gln Val His
        115                 120                 125

Arg Gly Met Tyr Tyr Tyr Leu Tyr Arg Pro Ala Asn Gln Pro Ser Ile
    130                 135                 140

Ser Asn Lys Ser Leu Asp Gln Leu Val Lys Glu Thr Leu Ala Gly Val
145                 150                 155                 160

His Gly Asn Gly Asp Thr Arg Lys Ala Ser Leu Gly Ser Gln Tyr Glu
                165                 170                 175

Ala Val Met Ala Val Ile Asn Gly Lys Ala Ser Ala Ser Glu Lys Ser
            180                 185                 190

Asp Glu Glu Leu Ala Arg Glu Val Leu Ala Gly Lys His Gly Ala Gly
        195                 200                 205

Glu Asp Arg Lys Arg Ser Leu Gly Pro Arg Tyr Glu Pro Val Gln Ala
    210                 215                 220

Lys Val Asn Glu Leu Leu Lys Ala Lys Glu Lys Pro Ser Glu Thr Ala
225                 230                 235                 240

Lys Asn Glu Pro Gln Thr Val Gln Phe Lys Glu Asp Gly Asp Leu
                245                 250                 255

<210> SEQ ID NO 3
<211> LENGTH: 245
<212> TYPE: PRT
<213> ORGANISM: Streptococcus suis

<400> SEQUENCE: 3

Met Thr Thr Val Asn Glu Ala Leu Asn Val Arg Ala Gln Val Gly
1               5                   10                  15

Ser Gly Val Ser Val Gly Asn Gly Glu Cys Tyr Ala Leu Ala Ser Trp
            20                  25                  30

Tyr Glu Arg Met Ile Ser Pro Asp Ala Thr Val Gly Leu Gly Ala Gly
        35                  40                  45

Val Gly Trp Val Ser Gly Ala Ile Gly Asp Thr Ile Ser Ala Lys Asn
    50                  55                  60

Ile Gly Ser Ser Tyr Asn Trp Gln Ala Asn Gly Trp Thr Val Ser Thr
65                  70                  75                  80
```

-continued

```
Ser Gly Pro Phe Lys Ala Gly Gln Ile Val Thr Leu Gly Ala Thr Pro
                85                  90                  95

Gly Asn Pro Tyr Gly His Val Val Ile Val Glu Ala Val Asp Gly Asp
            100                 105                 110

Arg Leu Thr Ile Leu Glu Gln Asn Tyr Gly Gly Lys Arg Tyr Pro Val
        115                 120                 125

Arg Asn Tyr Tyr Ser Ala Ala Ser Tyr Arg Gln Gln Val Val His Tyr
    130                 135                 140

Ile Thr Pro Pro Gly Thr Val Ala Gln Ser Ala Pro Asn Leu Ala Gly
145                 150                 155                 160

Ser Arg Ser Tyr Arg Glu Thr Gly Thr Met Thr Val Thr Val Asp Ala
                165                 170                 175

Leu Asn Val Arg Arg Ala Pro Asn Thr Ser Gly Glu Ile Val Ala Val
            180                 185                 190

Tyr Lys Arg Gly Glu Ser Phe Asp Tyr Asp Thr Val Ile Ile Asp Val
        195                 200                 205

Asn Gly Tyr Val Trp Val Ser Tyr Ile Gly Gly Ser Gly Lys Arg Asn
    210                 215                 220

Tyr Val Ala Thr Gly Ala Thr Lys Asp Gly Lys Arg Phe Gly Asn Ala
225                 230                 235                 240

Trp Gly Thr Phe Lys
                245

<210> SEQ ID NO 4
<211> LENGTH: 139
<212> TYPE: PRT
<213> ORGANISM: Streptococcus suis
<220> FEATURE:
<221> NAME/KEY: DOMAIN
<222> LOCATION: (1)..(139)
<223> OTHER INFORMATION: CHAP DOMAIN

<400> SEQUENCE: 4

Leu Asn Asn Val Arg Ala Gln Val Gly Ser Gly Val Ser Val Gly Asn
1               5                   10                  15

Gly Glu Cys Tyr Ala Leu Ala Ser Trp Tyr Arg Met Ile Ser Pro
                20                  25                  30

Asp Ala Thr Val Gly Leu Gly Ala Gly Val Trp Val Ser Gly Ala
            35                  40                  45

Ile Gly Asp Thr Ile Ser Ala Lys Asn Ile Gly Ser Ser Tyr Asn Trp
    50                  55                  60

Gln Ala Asn Gly Trp Thr Val Ser Thr Ser Gly Pro Phe Lys Ala Gly
65                  70                  75                  80

Gln Ile Val Thr Leu Gly Ala Thr Pro Gly Asn Pro Tyr Gly His Val
                85                  90                  95

Val Ile Val Glu Ala Val Asp Gly Asp Arg Leu Thr Ile Leu Glu Gln
            100                 105                 110

Asn Tyr Gly Gly Lys Arg Tyr Pro Val Arg Asn Tyr Tyr Ser Ala Ala
        115                 120                 125

Ser Tyr Arg Gln Gln Val Val His Tyr Ile Thr
    130                 135

<210> SEQ ID NO 5
<211> LENGTH: 67
<212> TYPE: PRT
<213> ORGANISM: Streptococcus suis
<220> FEATURE:
```

```
<221> NAME/KEY: DOMAIN
<222> LOCATION: (1)..(67)
<223> OTHER INFORMATION: SH3 DOMAIN

<400> SEQUENCE: 5
```

| Arg | Ser | Tyr | Arg | Glu | Thr | Gly | Thr | Met | Thr | Val | Thr | Val | Asp | Ala | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Asn Val Arg Arg Ala Pro Asn Thr Ser Gly Glu Ile Val Ala Val Tyr
            20                  25                  30

Lys Arg Gly Glu Ser Phe Asp Tyr Asp Thr Val Ile Ile Asp Val Asn
            35                  40                  45

Gly Tyr Val Trp Val Ser Tyr Ile Gly Gly Ser Gly Lys Arg Asn Tyr
    50                  55                  60

Val Ala Thr
65

```
<210> SEQ ID NO 6
<211> LENGTH: 137
<212> TYPE: PRT
<213> ORGANISM: Streptococcus suis
<220> FEATURE:
<221> NAME/KEY: DOMAIN
<222> LOCATION: (1)..(137)
<223> OTHER INFORMATION: ENDOPEPTIDASE DOMAIN

<400> SEQUENCE: 6
```

Leu Glu Thr Ser Ile Arg Trp Met Ser Asp Arg Val Gly Lys Val Ser
1               5                   10                  15

Tyr Ser Met Asp Tyr Arg Asn Gly Pro Asn Ser Tyr Asp Cys Ser Ser
            20                  25                  30

Ala Val Tyr Tyr Ala Leu Met Ala Gly Gly Ala Ile Ser Ala Gly Trp
        35                  40                  45

Ala Val Asn Thr Glu Tyr Met His Asp Trp Leu Ile Arg Asn Gly Tyr
    50                  55                  60

Val Leu Val Ala Glu Asn Lys Pro Phe Asn Ala Gln Arg His Asp Val
65                  70                  75                  80

Cys Ile Leu Gly Lys Arg Gly Tyr Ser Ser Gly Ala Gly His Val
                85                  90                  95

Val Ile Phe Val Asp Asn Val Asn Val Ile His Cys Asn Tyr Ala Arg
            100                 105                 110

Asn Gly Ile Ser Ile Asp Asn Tyr Asn Gln Val His Arg Gly Met Tyr
        115                 120                 125

Tyr Tyr Leu Tyr Arg Pro Ala Asn Gln
    130                 135

```
<210> SEQ ID NO 7
<211> LENGTH: 82
<212> TYPE: PRT
<213> ORGANISM: Streptococcus suis
<220> FEATURE:
<221> NAME/KEY: DOMAIN
<222> LOCATION: (1)..(82)
<223> OTHER INFORMATION: DUAL CPL-7 DOMAIN

<400> SEQUENCE: 7
```

Asp Gln Leu Val Lys Glu Thr Leu Ala Gly Val His Gly Asn Gly Asp
1               5                   10                  15

Thr Arg Lys Ala Ser Leu Gly Ser Gln Tyr Glu Ala Val Met Ala Val
            20                  25                  30

Ile Asn Gly Lys Ala Ser Ala Ser Glu Lys Ser Asp Glu Glu Leu Ala
        35                  40                  45

Arg Glu Val Leu Ala Gly Lys His Gly Ala Gly Glu Asp Arg Lys Arg
 50                  55                  60

Ser Leu Gly Pro Arg Tyr Glu Pro Val Gln Ala Lys Val Asn Glu Leu
 65                  70                  75                  80

Leu Lys

<210> SEQ ID NO 8
<211> LENGTH: 125
<212> TYPE: PRT
<213> ORGANISM: Streptococcus suis
<220> FEATURE:
<221> NAME/KEY: DOMAIN
<222> LOCATION: (1)..(125)
<223> OTHER INFORMATION: GLUCOSAMINIDASE DOMAIN

<400> SEQUENCE: 8

Ile Leu Lys Lys Cys Lys Glu His Asp Ile Leu Pro Ser Tyr Ala Leu
 1               5                  10                  15

Thr Ile Leu His Tyr Glu Gly Leu Trp Gly Thr Ser Ala Val Gly Lys
                20                  25                  30

Ala Asp Asn Asn Trp Gly Gly Met Thr Trp Thr Gly Gln Gly Asn Arg
            35                  40                  45

Pro Ser Gly Val Ile Val Thr Gln Gly Leu Ala Arg Pro Ser Asn Glu
 50                  55                  60

Gly Gly His Tyr Met His Tyr Ala Thr Val Asp Asp Phe Leu Thr Asp
 65                  70                  75                  80

Trp Phe Tyr Leu Leu Arg Lys Asp Gly Ser Tyr Lys Val Ser Gly Ala
                85                  90                  95

Leu Thr Phe Ser Glu Ser Ile Lys Gly Met Phe Gln Val Gly Gly Ala
            100                 105                 110

Lys Tyr Asp Tyr Ala Ala Ala Gly Tyr Asp Ser Tyr Leu
        115                 120                 125

<210> SEQ ID NO 9
<211> LENGTH: 29
<212> TYPE: DNA
<213> ORGANISM: Artificial Sequence
<220> FEATURE:
<223> OTHER INFORMATION: forward primer

<400> SEQUENCE: 9
aatgctagcc tgatacacag ttagagacc                                       29

<210> SEQ ID NO 10
<211> LENGTH: 33
<212> TYPE: DNA
<213> ORGANISM: Artificial Sequence
<220> FEATURE:
<223> OTHER INFORMATION: reverse primer

<400> SEQUENCE: 10
cctaagcttc ttttcacaaa tcataatccc cag                                  33

<210> SEQ ID NO 11
<211> LENGTH: 1359
<212> TYPE: DNA
<213> ORGANISM: Streptococcus suis

<400> SEQUENCE: 11
atgacaatca atcttgaaac atccattcgt tggatgagcg accgtgtcgg caaagtctct     60
tactcaatgg actatcgtaa cggtccgaat agttatgact gctctagtgc tgtatattat    120

```
gcgctaatgg cgggtggtgc aatttctgca ggttgggcgg ttaacactga gtatatgcat      180
gactggttga tacgtaacgg atatgttttg gtagctgaaa ataaaccatt taacgctcaa      240
agacatgacg tttgtatttt gggtaaacgt ggctattcga gcggagcagg tggtcacgtc      300
gttatctttg tggataatgt taatgtgata cattgtaact atgcacgtaa cggaatttcc      360
attgataatt ataatcaagt gcatcgtggt atgtattact atctatatcg cccagcaaat      420
caacccagca tcagcaacaa atcactggat cagcttgtta aggagacttt ggctggggta      480
catggcaacg gggacacccg taaggcaagt cttggcagtc aatacgaggc tgtcatggcg      540
gttatcaatg gcaaagcttc ggcaagcgag aaatctgatg aggaacttgc tagggaagtc      600
ttagcaggta agcacggggc tggagaggac cgaaaacggt cattaggacc acgctatgag      660
cctgttcaag ccaaggtcaa cgaattgctc aaggctaagg aaaaaccgtc tgagacggcc      720
aaaaatgaac cacagacggt gcaattcaag gaggacgggg acttgtcttt caatggtgcc      780
attcttaaga gtctgtcct cgaaattatc ctgaaaaagt gtaaagaaca tgacatctta      840
ccaagctatg ccctaactat cctacactat gaagggcttt ggggcacttc tgctgtcggt      900
aaggccgaca caactggggg cggtatgacc tggactggcc aaggcaaccg tccgagcgga      960
gtaattgtga ctcaaggttt ggctcggcca tcgaacgagg gaggccacta catgcactat     1020
gccaccgtgg atgatttcct gacggactgg ttctacctgc ttcgcaagga cgggtcttac     1080
aaggtatctg gtgcattgac cttcagcgag tccattaagg gcatgttcca ggttggcgga     1140
gctaaatacg actatgcagc cgccggctac gatagttacc tggtcggcgc cactagcagg     1200
ctaaaagcta tcgagtccga aaatggcagt ctgacacggt ttgatgccac atcaaataat     1260
gtccattcgg ttgaccctga taaaatctct gttgatattg acggcattga agttacgatc     1320
aatggtgttg tctacaagct ggaaaagaaa ccagtctaa                            1359
```

<210> SEQ ID NO 12
<211> LENGTH: 738
<212> TYPE: DNA
<213> ORGANISM: Streptococcus suis

<400> SEQUENCE: 12

```
atgacaacag taaatgaagc attaaataat gtaagagctc aggttgggtc cggtgtgtct       60
gttggcaacg gcgaatgcta cgctttggct agttggtacg agcgcatgat tagtccggat      120
gcaactgtcg gacttggcgc tggtgtgggc tgggtcagcg gtgcaatcgg cgatacaatc      180
tctgccaaaa acatcggctc atcatacaac tggcaagcta acggctggac agtttccaca      240
tctggtccat ttaaagcagg tcagattgtg acgcttgggg caacaccagg aaacccttac      300
ggacatgtgt aatcgtcga agcagtggac ggcgatagat tgactatttt ggagcaaaac      360
tacggcggga aacgttatcc cgtccgtaat tattacagcg ctgcaagcta tcgtcaacag      420
gtcgtgcatt acatcacacc gcctggcacg gtcgcacagt cagcacccaa ccttgcaggc      480
tctcgttcct atcgcgagac gggcactatg actgtcacgg tcgatgctct caatgttcgc      540
agggcgccaa atacttcagg cgagattgta gcagtataca agcgtggtga atcatttgac      600
tatgatactg tcatcatcga tgtcaatggc tatgtctggg tgtcttacat aggcggcagc      660
ggcaaacgta actacgttgc gacgggcgct accaaagacg gtaagcgttt cggcaatgct      720
tggggtacat ttaaataa                                                     738
```

<210> SEQ ID NO 13

```
<211> LENGTH: 143
<212> TYPE: PRT
<213> ORGANISM: Streptococcus suis
<220> FEATURE:
<221> NAME/KEY: DOMAIN
<222> LOCATION: (1)..(143)
<223> OTHER INFORMATION: ENZYMATIC DOMAIN

<400> SEQUENCE: 13
```

Thr Val Asn Glu Ala Leu Asn Asn Val Arg Ala Gln Val Gly Ser Gly
1               5                   10                  15

Val Ser Val Gly Asn Gly Glu Cys Tyr Ala Leu Ala Ser Trp Tyr Glu
            20                  25                  30

Arg Met Ile Ser Pro Asp Ala Thr Val Gly Leu Gly Ala Gly Val Gly
        35                  40                  45

Trp Val Ser Gly Ala Ile Gly Asp Thr Ile Ser Ala Lys Asn Ile Gly
    50                  55                  60

Ser Ser Tyr Asn Trp Gln Ala Asn Gly Trp Thr Val Ser Thr Ser Gly
65              70                  75                  80

Pro Phe Lys Ala Gly Gln Ile Val Thr Leu Gly Ala Thr Pro Gly Asn
                85                  90                  95

Pro Tyr Gly His Val Val Ile Val Glu Ala Val Asp Gly Asp Arg Leu
            100                 105                 110

Thr Ile Leu Glu Gln Asn Tyr Gly Gly Lys Arg Tyr Pro Val Arg Asn
        115                 120                 125

Tyr Tyr Ser Ala Ala Ser Tyr Arg Gln Gln Val Val His Tyr Ile
    130                 135                 140

```
<210> SEQ ID NO 14
<211> LENGTH: 150
<212> TYPE: PRT
<213> ORGANISM: Streptococcus suis
<220> FEATURE:
<221> NAME/KEY: DOMAIN
<222> LOCATION: (1)..(150)
<223> OTHER INFORMATION: C1 ENZYMATIC DOMAIN

<400> SEQUENCE: 14
```

Asn Leu Ala Asn Ala Gln Ala Gln Val Gly Lys Tyr Ile Gly Asp Gly
1               5                   10                  15

Gln Cys Tyr Ala Trp Val Gly Trp Ser Ala Arg Val Cys Gly Tyr
            20                  25                  30

Ser Ile Ser Tyr Ser Thr Gly Asp Pro Met Leu Pro Leu Ile Gly Asp
            35                  40                  45

Gly Met Asn Ala His Ser Ile His Leu Gly Trp Asp Trp Ser Ile Ala
    50                  55                  60

Asn Thr Gly Ile Val Asn Tyr Pro Val Gly Thr Val Gly Arg Lys Glu
65              70                  75                  80

Asp Leu Arg Val Gly Ala Ile Trp Cys Ala Thr Ala Phe Ser Gly Ala
                85                  90                  95

Pro Phe Tyr Thr Gly Gln Tyr Gly His Thr Gly Ile Ile Glu Ser Trp
            100                 105                 110

Ser Asp Thr Thr Val Thr Val Leu Glu Gln Asn Ile Leu Gly Ser Pro
        115                 120                 125

Val Ile Arg Ser Thr Tyr Asp Leu Asn Thr Phe Leu Ser Thr Leu Thr
    130                 135                 140

Gly Leu Ile Thr Phe Lys
145                 150

UNITED STATES PATENT AND TRADEMARK OFFICE
CERTIFICATE OF CORRECTION

PATENT NO. : 9,914,915 B2  
APPLICATION NO. : 14/685696  
DATED : March 13, 2018  
INVENTOR(S) : Vincent A. Fischetti et al.

Page 1 of 1

It is certified that error appears in the above-identified patent and that said Letters Patent is hereby corrected as shown below:

In the Specification

Column 1, Lines 21-25, replace:
"STATEMENT OF GOVERNMENT SUPPORT
This invention was made with government support under AI11822 awarded by the NIH. The government has certain rights in the invention."

With:
-- STATEMENT OF GOVERNMENT SUPPORT
This invention was made with government support under grant number AI011822 awarded by the National Institutes of Health. The government has certain rights in the invention. --

Signed and Sealed this  
Eleventh Day of February, 2020

Andrei Iancu  
*Director of the United States Patent and Trademark Office*